(12) United States Patent
Hellendoorn et al.

(10) Patent No.: US 7,754,853 B2
(45) Date of Patent: Jul. 13, 2010

(54) TNF ALPHA-BINDING POLYPEPTIDE COMPOSITIONS AND METHODS

(75) Inventors: Koen Hellendoorn, Newmarket (GB);
Matthew Baker, Littleport Ely (GB);
Francis J. Carr, Balmedie (GB)

(73) Assignee: Merck Patent GmbH, Darmstadt (DE)

( * ) Notice: Subject to any disclaimer, the term of this patent is extended or adjusted under 35 U.S.C. 154(b) by 758 days.

(21) Appl. No.: 11/005,726

(22) Filed: Dec. 7, 2004

(65) Prior Publication Data

US 2006/0018903 A1    Jan. 26, 2006

Related U.S. Application Data

(63) Continuation-in-part of application No. 10/495,146, filed as application No. PCT/EP02/12566 on Nov. 11, 2002.

(30) Foreign Application Priority Data

Nov. 12, 2001    (EP) .................................. 01126858

(51) Int. Cl.
*A61K 38/00* (2006.01)
(52) U.S. Cl. ...................................... 530/326; 530/327
(58) Field of Classification Search ........................ None
See application file for complete search history.

(56) References Cited

U.S. PATENT DOCUMENTS 5,519,000 A * 5/1996 Heavner et al. ............... 514/12

FOREIGN PATENT DOCUMENTS

WO    WO 9007861 A1 *  7/1990
WO    WO 0132712 A2 *  5/2001

OTHER PUBLICATIONS

Sant'Angelo et al., Eur J Immunol. Sep. 2002;32(9):2510-20.*
Robertson et al., J Immunol. May 1, 2000;164(9):4706-12.*

* cited by examiner

*Primary Examiner*—Zachary Skelding
(74) *Attorney, Agent, or Firm*—Olson & Cepuritis, Ltd.

(57) ABSTRACT

This invention pertains to a TNF alpha-binding polypeptide composition comprising at least one of a modified heavy chain variable region polypeptide or a modified light chain variable region polypeptide that is capable of specifically binding to human TNF alpha. The modified heavy and light chain variable region polypeptides of the TNF alpha binding polypeptide are modified by at least one amino acid residue substitution, deletion or addition and are homologous to the heavy and light chain variable regions, respectively, of a non-human monoclonal antibody that specifically binds human TNF alpha. The polypeptide compositions of the invention comprising modified heavy and light chain variable region polypeptides are less immunogenic in a human than are the homologous heavy and light chain variable region polypeptides from a non-human animal.

3 Claims, 27 Drawing Sheets

VH Forward strand oligonucleotides (SEQ ID NO in parentheses below the sequence):

Figure 1B

VH Reverse strand oligonucleotides (SEQ ID NO in parentheses below the sequence):

```
3' CTTCACTTCGACCTCCTCAG         3' ACCTCCGCCGAACCACGTTGACCTCCGAGGTACTTTGAG
   ◄------------- OL-391           ◄------------------------- OL-390
   (SEQ ID NO: 41)                    (SEQ ID NO: 40)

3' AGGACACAACGGAGACCTAAGTAAAAGTCATTGGTGACCT   3' ACTTGACCCAGGCGGTCAGAGGTCTCTTCCCGAACTCAC
   ◄------------------------------- OL-389      ◄-------------------------------- OL-388
   (SEQ ID NO: 39)                                 (SEQ ID NO: 38)

3' CCAACGACTTTAATCTAGTTTTAGCTAATTAAGACGTTGT   3' GTAATACGCCTCAGACACTTTCCCTCCAAGTGGTAGAGTT
   ◄------------------------------- OL-387      ◄-------------------------------- OL-386
   (SEQ ID NO: 37)                                 (SEQ ID NO: 36)

3' CTTCTACTAAGGTTTTCACGACACATGGACGTTTACTGGCT  3' GGACTCTTGACTTCTGTGACCGCAAATAATGACAAGGTCC
   ◄-------------------------------- OL-385     ◄-------------------------------- OL-384
   (SEQ ID NO: 35)                                 (SEQ ID NO: 34)

3' TTAATGATGCCATCATGGATGCTGATGACCCCGGTTCCGT   3' GGTGAGAGTGTCACAGGAGTCC
   ◄-------------------------------- OL-383     ◄--------------- OL-382
   (SEQ ID NO: 33)                                 (SEQ ID NO: 32)
```

5' GAAGTGAAGCTGGAGGAGTCTGGAGGCGGCTTGGTGCAGCCTCCATGAAACTCTCCTGTGCCTCTGGATTCATTTTCAGTAACCACTGGATGAACTGGGTCCGC
3' CTTCACTTCGACCTCCTCAGACCTCCGCCGAACCACGTTGGAGGTACTTGAGACCTAAGTAAAAGTCATTGGTGACCTACTTGACCCAGGCG

5' CAGTCTCCAGAGAAGGGGCTTGAGTGGGTTGCTGAAATCAGATAATTCTGCAACACATTATGCGAAGGAGTTCACCATCTCAAGAGATGAT
3' GTCAGAGGTCTCTTCCCCGAACTCACCCAACTCACTTTAAGTTTTAGCTAATTAAGACGTTGTGAATACGCTTCCCTGAAGTGGTAGAGTTCTCTACTA

5' TCCAAAAGTGCTGTGTACCTGCAAATGACCGACCTGGCGTTTATTACTGCGTTTACTGTTCCAGAACTACGGTAGTAGTACTACGGGCCAAGGCACC
3' AGGTTTTCACGACACATGGACGTTTACTGGCTGGACCGCAAATAATGACGCAAATAATGACAAGGTCCTTAATGATGCCATCATGATGCTGATGACCCCGGTTCCGTGG

5' ACTCTCACAGTGTCCTCAGG (SEQ ID NO: 156)
3' TGAGAGTGTCACAGGAGTCC-5' (SEQ ID NO: 157)
         OL-382

⇒

5' GAAGTGAAGCTGGAGGAGTCTGGAGGCGGCTTGGTGCAACCTGGAGGCTCCATGAAACTCTCCTGTGCCTCTGTGTTGCCCCTCTGTTGCCGATTCATTTTCAGTAACCACTGGATGAACTGGGTCCGC
   E  V  K  L  E  E  S  G  G  G  L  V  Q  P  G  G  S  M  K  L  S  C  V  A  S  G  F  I  F  S  N  H  W  M  N  W  V  R

5' CAGTCTCCAGAGAAGGGGCTTGAGTGGGTTGCTGAAATCAGATAATTCTGCAACACATTATGCGAAGGAGTTCACCATCTCAAGAGATGAT
   Q  S  P  E  K  G  L  E  W  V  A  E  I  R  S  K  S  I  N  S  A  T  H  Y  A  E  S  V  K  G  R  F  T  I  S  R  D  D

5' TCCAAAAGTGCTGTGTACCTGCAAATGACCGACCTGCGTTTATTACTGTTCCAGGAATTACTACGGTAGTACTGACTACTGGGGCCAAGGCACC
   S  K  S  A  V  Y  L  Q  M  T  D  L  R  T  E  D  T  G  V  Y  Y  C  S  R  N  Y  Y  G  S  T  Y  D  Y  W  G  Q  G  T

5' ACTCTCACAGTGTCCTCAGG (SEQ ID NO: 156)
   T  L  T  V  S  S    (SEQ ID NO: 9)

Figure 1E

VH Sequence (WT)
(SEQ ID NO: 9)

EVKLEESGGGLVQPGGSMKLSCVASGFIFSNHWMNWVRQSPEKGLE
WVAEIRSKSINSATHYAESVKGRFTISRDDSKSAVYLQMTDLRTED
TGVYYCSRNYYGSTYDYWGQGTTLTVSS

VL Forward strand oligonucleotides (SEQ ID NO in parentheses below the sequence):

VL Reverse strand oligonucleotides (SEQ ID NO in parentheses below the sequence):

Figure 1J

VL Sequence (WT)

(SEQ ID NO: 10)

DILLTQSPAILSVSPGERVSFSCRASQFVGSSIHWYQQRTNGSPRL
LIKYASESMSGIPSRFSGSGSGTDFTLSINTVESEDIADYYCQQSH
SWPFTFGSGTNLEVKRE

Neutralisation of the TNFα induced killing of WEHI164 cells

Neutralisation of the TNFα stimulated production of ICAM-1 in HUVE cells

Competition with TNF-receptor for binding TNFα

FIGURE 6
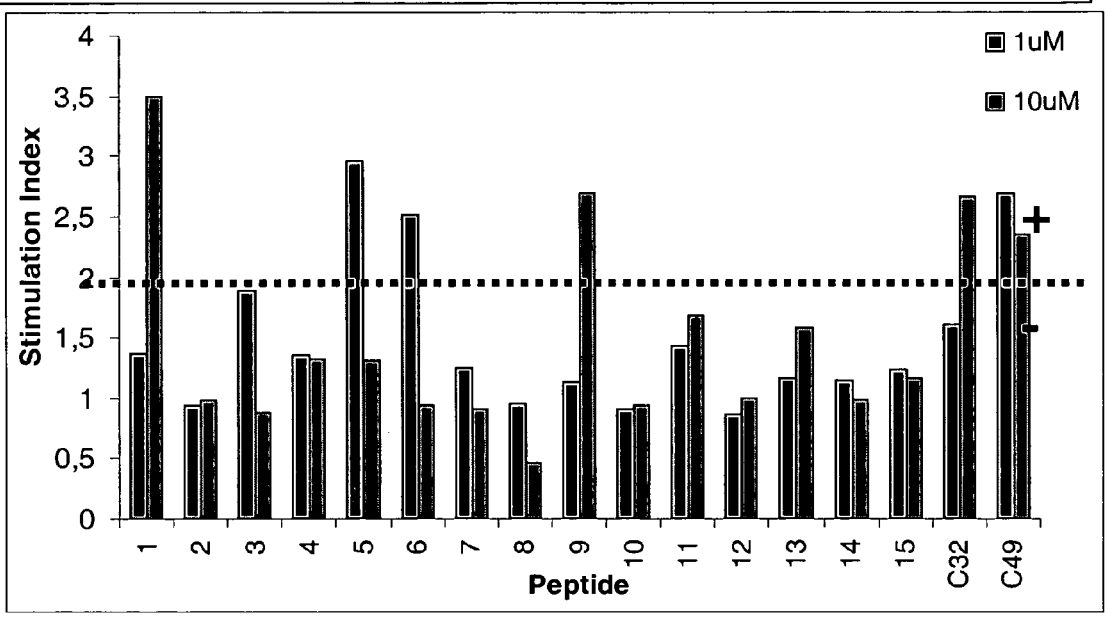
A) Donor #2 response to stimulation with peptides P1-P15
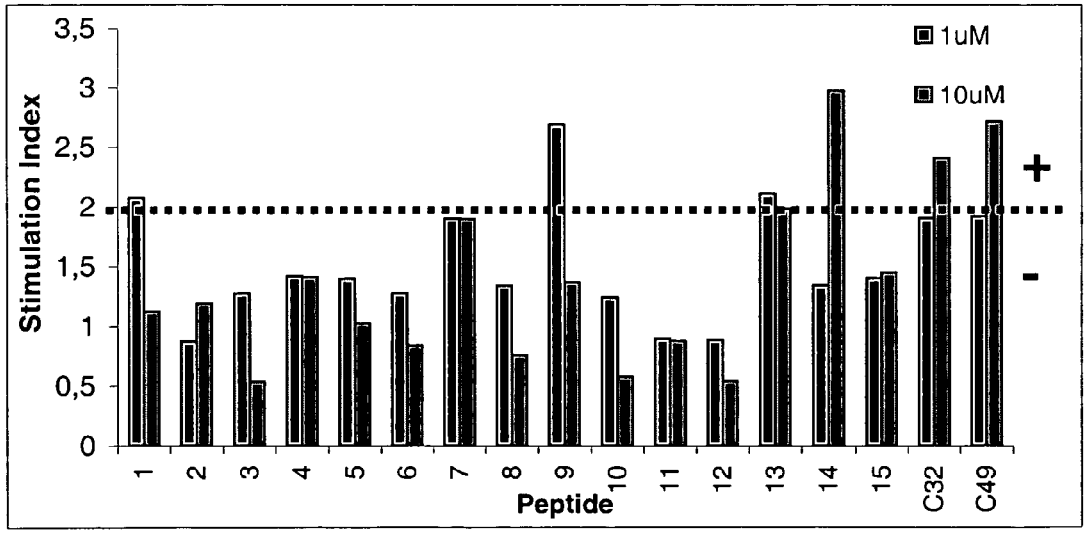
B) Donor #4 response to stimulation with peptides P1-P15

FIGURE 8

VH1 (SEQ ID NO: 1)
EVQLVESGGGLVQPGGSLRLSCAASGFTFSNHWMNWVRQSPEKGLEWVAEIRSK
SINSATHYAESVKGRFTISRDDSKNSLYLQMNSLKTEDTAVYYCSRNYYGSTYD
YWGQGTTLTVSS

VH3 (SEQ ID NO: 2)
EVKLEESGGGLVQPGGSLRLSCAASGFTFSNHWMNWVRQSPEKGLEWVAEIRSK
SINSATHYAESVKGRFTISRDDSKNSLYLQMNSLKTEDTGVYYCSRNYYGSTYD
YWGQGTTVTVSS

VH5 (SEQ ID NO: 3)
EVKLEESGGGLVQPGGSLRLSCAASGFTFSNHWMNWVRQSPEKGLEWVAETRSK
STNSATHYAESVKGRFTISRDDSKNSLYLQMNSLKTEDTGVYYCSRNYYGSTYD
YWGQGTTVTVSS

VH8 (SEQ ID NO: 4)
EVQLVESGGGLVQPGGSLRLSCAASGFTFSNHWMNWVRQSPEKGLEWVAETRSK
STNSATHYADSVKGRFTISRDDSKNSLYLQMNSLKTEDTAVYYCSRNYYGSTYD
YWGQGTLVTVSS

VL1 (SEQ ID NO: 5)
DIQLTQSPDTSSASPGERVSFSCRASQFVGSSIHWYQQRTNGSPRLLIKYASES
MSGVPSRFSGSGSGTDFTLTINSLEAEDAATYYCQQSHSWPFTFGSGTNVEVKR

VL12 (SEQ ID NO: 6)
DIQLTQSPDTSSASPGERASFSCRASQFVGSSIHWYQHTTNGSPRLLIKYASES
MSGVPSRFSGSGSGTDFTLTINSLEAEDAATYYCQQSHSWPFTFGSGTNLEVKR

VL5 (SEQ ID NO: 7)
DIQLTQSPDTSSASPGERVSFSCRASQFVGSSIHWYQQRTNGSPRLLIKYASES
MSGVPSRFSGSGSGTDFTLTINSLEAEDAATYYCQQSHSWPFTFGGGTKVEIKR

VL8 (SEQ ID NO: 8)
DIQLTQSPDTSSASPGERASFSCRASQFVGSSIHWYQHTTNGSPRLLIKYASES
MSGVPSRFSGSGSGTDFTLTINSLEAEDAATYYCQQSHSWPFTFGGGTKVEIKR (Vh5/Vk12 = CP-1)

Figure 11

PEPTIDE FRAGMENTS OF SEQ ID NO: 11 (amino acid residues of SEQ ID NO: 11 in parentheses)

```
CA1   EVKLEESGGGLVQPG     (AA 1-15 of SEQ ID NO: 11)
CA2    LEESGGGLVQPGGGSM   (4-18)
CA3       SGGGLVQPGGSMKLS (7-21)
CA4          GLVQPGGSMKLSCVA (10-24)
CA5             QPGGSMKLSCVASGF (13-27)
CA6                GGSMKLSCVASGFIFS (16-30)
CA7                   KLSCVASGFIFSNHW (19-33)
CA8                      CVASGFIFSNHWMNW (22-36)
CA9                         SGFIFSNHWMNWVRQ (25-39)
CA10                           IFSNHWMNWVRQSPE (28-42)
CA11                              NHWMNWVRQSPEKGL (31-45)
CA12                                 MNWVRQSPEKGLEWV (34-48)
CA13                                    VRQSPEKGLEWVAEI (37-51)
CA14                                       SPEKGLEWVAEIRSK (40-54)
CA15                                          KGLEWVAEIRSKSIN (43-57)
CA16                                             EWVAEIRSKSINSAT (46-60)
CA17                                                AEIRSKSINSATHYA (49-63)
CA18                                                   RSKSINSATHYAESV (52-65)
CA19                                                      SINSATHYAESVKGR (55-68)
CA20                                                         SATHYAESVKGRFTI (58-72)
CA21                                                            HYAESVKGRFTISRD (61-75)
CA22                                                               ESVKGRFTISRDDSK (64-78)
CA23                                                                  KGRFTISRDDSKSAV (67-81)
CA24                                                                     FTISRDDSKSAVYLQ (70-84)
CA25                                                                        SRDDSKSAVYLQMTD (73-87)
CA26                                                                           DSKSAVYLQMTDLRT (75-90)
CA27                                                                              SAVYLQMTDLRTEDT (78-93)
CA28                                                                                 YLQMTDLRTEDTGVY (81-96)
CA29                                                                                    MTDLRTEDTGVYYCS (84-99)
CA30                                                                                       LRTEDTGVYYCSRNY (87-102)
CA31                                                                                          EDTGVYYCSRNYYGS (90-105)
CA32                                                                                             GVYYCSRNYYGSTYD (93-108)
CA33                                                                                                YCSRNYYGSTYDYWG (96-111)
CA34                                                                                                   RNYYGSTYDYWGQGT (99-114)
CA35                                                                                                      YGSTYDYWGQGTTLT (102-117)
CA36                                                                                                         TYDYWGQGTTLTVSS (105-120)
CA37                                                                                                            YWGQGTTLTVSSAST (108-123)
CA38                                                                                                               QGTTLTVSSASTKGP (111-126)
CA39                                                                                                                  TLTVSSASTKGPSVF (114-129)
CA40                                                                                                                     VSSASTKGPSVFPLA (117-132)
```

SEQ ID NO: 11
EVKLEESGGGLVQPGGGSMKLSCVASGFIFSNHWMNWVRQSPEKGLEWVAEIRSKSINSATHYAESVKGRFTISRDDSKSAVYLQMTDLRTEDTGVYYCSRNYYGSTYDYWGQGTTLTVSSASTKGPSVFPLA

PEPTIDE FRAGMENTS OF SEQ ID NO: 12 (amino acid residues of SEQ ID NO: 12 in parentheses)

CA41 DILLTQSPAILSVSP (AA 1-15 of SEQ ID NO: 12)
CA42 LTQSPAILSVSPGER (4-18)
CA43 SPAILSVSPGERVSF (7-21)
CA44 ILSVSPGERVSFSCR (10-24)
CA45 VSPGERVSFSCRASQ (13-27)
CA46 GERVSFSCRASQFVG (16-30)
CA47 VSFSCRASQFVGSSI (19-33)
CA48 SCRASQFVGSSIHWY (22-36)
CA49 ASQFVGSSIHWYQQR (25-39)
CA50 FVGSSIHWYQQRTNG (28-42)
CA51 SSIHWYQQRTNGSPR (31-45)
CA52 HWYQQRTNGSPRLLI (34-48)
CA53 QQRTNGSPRLLIKYA (37-51)
CA54 TNGSPRLLIKYASES (40-54)
CA55 SPRLLIKYASESMSG (43-57)
CA56 LLIKYASESMSGIPS (46-60)
CA57 KYASESMSGIPSRFS (49-63)
CA58 SESMSGIPSRFSGSG (52-66)
CA57 MSGIPSRFSGSGSGT (55-69)
CA60 IPSRFSGSGSGTDFT (58-72)
CA61 RFSGSGSGTDFTLSI (61-75)
CA62 GSGSGTDFTLSINTV (64-78)
CA63 SGTDFTLSINTVESE (67-81)
CA64 DFTLSINTVESEDIA (70-84)
CA65 LSINTVESEDIADYY (73-87)
CA66 NTVESEDIADYYCQQ (75-90)
CA67 ESEDIADYYCQQSHS (78-93)
CA68 DIADYYCQQSHSWPF (81-96)
CA69 DYCQQSHSWPFTFG (84-99)
CA70 CQQSHSWPFTFGSGT (87-102)
CA71 SHSWPFTFGSGTNLE (90-105)
CA72 WPFTFGSGTNLEVKR (93-108)
CA73 TFGSGTNLEVKRTVA (96-111)
CA74 SGTNLEVKRTVAAPS (99-114)
CA75 NLEVKRTVAAPSVFI (102-117)

(SEQ ID NO: 12)
DILLTQSPAILSVSPGERVSFSCRASQFVGSSIHWYQQRTNGSPRLLIKYASESMSGIPSRFSGSGSGTDFTLSINTVESEDIADYYCQQSHSWPFTFGSGTNLEVKRTVAAPSVFI

SEQ ID NO is listed in parenthesis after sequence:

```
VKLEESGGGLVQP  ( 94),   GGLVQPGGSMKLS  ( 95),   GLVQPGGSMKLSC  ( 96),
GSMKLSCVASGFI  ( 97),   MKLSCVASGFIFS  ( 98),   SCVASGFIFSNHW  ( 99),
SGFIFSNHWMNWV  (100),   GFIFSNHWMNWVR  (101),   FIFSNHWMNWVRQ  (102),
NHWMNWVRQSPEK  (103),   HWMNWVRQSPEKG  (104),   MNWVRQSPEKGLE  (105),
NWVRQSPEKGLEW  (106),   KGLEWVAEIRSKS  (107),   LEWVAEIRSKSIN  (108),
EWVAEIRSKSINS  (109),   AEIRSKSINSATH  (110),   KSINSATHYAESV  (111),
THYAESVKGRFTI  (112),   ESVKGRFTISRDD  (113),   GRFTISRDDSKSA  (114),
FTISRDDSKSAVY  (115),   SAVYLQMTDLRTE  (116),   AVYLQMTDLRTED  (117),
VYLQMTDLRTEDT  (118),   LQMTDLRTEDTGV  (119),   TDLRTEDTGVYYC  (120),
TGVYYCSRNYYGS  (121),   GVYYCSRNYYGST  (122),   VYYCSRNYYGSTY  (123),
RNYYGSTYDYWGQ  (124),   NYYGSTYDYWGQG  (125),   STYDYWGQGTTLT  (126),
YDYWGQGTTLTVS  (127)
```

FIGURE 14

SEQ ID NO is listed in parenthesis after sequence:

```
DILLTQSPAILSV  (128),   ILLTQSPAILSVS  (129),   PAILSVSPGERVS  (130),
AILSVSPGERVSF  (131),   LSVSPGERVSFSC  (132),   ERVSFSCRASQFV  (133),
VSFSCRASQFVGS  (134),   SQFVGSSIHWYQQ  (135),   QFVGSSIHWYQQR  (136),
SSIHWYQQRTNGS  (137),   IHWYQQRTNGSPR  (138),   HWYQQRTNGSPRL  (139),
PRLLIKYASESMS  (140),   RLLIKYASESMSG  (141),   LLIKYASESMSGI  (142),
IKYASESMSGIPS  (143),   ESMSGIPSRFSGS  (144),   SGIPSRFSGSGSG  (145),
SRFSGSGSGTDFT  (146),   TDFTLSINTVESE  (147),   FTLSINTVESEDI  (148),
LSINTVESEDIAD  (149),   NTVESEDIADYYC  (150),   EDIADYYCQQSHS  (151),
ADYYCQQSHSWPF  (152),   DYYCQQSHSWPFT  (153),   HSWPFTFGSGTNL  (154),
WPFTFGSGTNLEV  (155)
```

FIGURE 15

(SEQ ID NO: 160) WT H-chain (truncated at the IgG1 stop codon)

```
GAATTCTAAATACATTTTAGAAGTCGATAAACTTAAGTTTGGGGAAACTAGAACTACTCA
AGCTAAAATTAAAAGGTTGAACTCAATAAGTTAAAAGAGGACCTCTCCAGTTTCGGCTGA
ATCCTCAACTTATTTTAGAAATGCAAATTACCCAGGTGGTGTTTTGCTCAGCCTGGACTT
TCGGTTTGGTGGGGCTGGACAGAGTGTTTCAAAACCACTTCTTCAAACCACAGCTACAAG
TTTACCTAGTGGTTTTATTTTCCCTTCCCCAAATAGCCTTGCCACATGACCTGCTTCCTG
CCAGCTGCTGCAGGTGTTCCGGTTCTGATCGGCCATCTTGACTCAACTCAACATTGCTCA
ATTCATTTAAAAATATTTTAAACTTAATTTATTATTGTTAAAAGTCAGTTCTGAATAGGG
TATGAGAGAGCCTCACTCCCATTCCTCGGTTAAACTTTAAGTAATGTCAGTTCTACACAA
ACAAGACCTCAAATTGATTGMCAAAAATTTTGGACATTTAAAAAAATGAGKACTTGAAAA
CCCTCTCACATTTTAAAGTCMCAGTATTTAACTATTTTTCCTAGGAACCAACTTAAGAGT
AAAGCAACATCTTCTAATATTCCATACACATACTTCTGTGTTCCTTTGAAAGCTGGACTT
TTGCAGGCTCCACCAGACCTCTCTAGGGAATTCTCATGTTTGACAGCTTATCATCGATAA
GCTTATGAATATGCAAATCCTCTGAATCTACATGGTAAATATAGGTTTGTCTATACCACA
AACAGAAAAACATGAGATCACAGTTCTCTACAGTTACTGAGCACACAGGACCTCACCA
TGGGATGGAGCTGTATCATCCTCTTCTTGGTAGCAACAGCTACAGGTAAGGGGCTCACAG
TAGCAGGCTTGAGGTCTGGACATATATATGGGTGACAATGACATCCACTTTGCCTTTCTC
TCCACAGGTGTCCACTCCGAAGTGAAGCTGGAGGAGTCTGGAGGCGGCTTGGTGCAACCT
GGAGGCTCCATGAAACTCTCCTGTGTTGCCTCTGGATTCATTTTCAGTAACCACTGGATG
AACTGGGTCCGCCAGTCTCCAGAGAAGGGGCTTGAGTGGGTTGCTGAAATTAGATCAAAA
TCGATTAATTCTGCAACACATTATGCGGAGTCTGTGAAAGGGAGGTTCACCATCTCAAGA
GATGATTCCAAAAGTGCTGTGTACCTGCAAATGACCGACCTGAGAACTGAAGACACTGGC
GTTTATTACTGTTCCAGGAATTACTACGGTAGTACCTACGACTACTGGGGCCAAGGCACC
ACTCTCACAGTGTCCTCAGGTGAGTCCTTACAACCTCTCTCTTCTATTCAGCTTAAATAG
ATTTTACTGCATTTGTTGGGGGGGAAATGTGTGTATCTGAATTTCAGGTCATGAAGGACT
AGGGACACCTTGGGAGTCAGAAAGGGTCATTGGGAGCCCGGGCTGATGCAGACAGACATC
CTCAGCTCCCAGACTTCATGGCCAGAGATTTATAGGATCCCAAGCTAGCTTTCTGGGGCA
GGCCAGGCCTGACCTTGGCTTTGGGGCAGGGAGGGGGCTAAGGTGAGGCAGGTGGCGCCA
GCCAGGTGCACACCCAATGCCCATGAGCCCAGACACTGGACGCTGAACCTCGCGGACAGT
TAAGAACCCAGGGGCCTCTGCGCCCTGGGCCCAGCTCTGTCCCACACCGCGGTCACATGG
CACCACCTCTCTTGCAGCCTCCACCAAGGGCCCATCGGTCTTCCCCCTGGCACCCTCCTC
CAAGAGCACCTCTGGGGGCACAGCGGCCCTGGGCTGCCTGGTCAAGGACTACTTCCCCGA
ACCGGTGACGGTGTCGTGGAACTCAGGCGCCCTGACCAGCGGCGTGCACACCTTCCCGGC
TGTCCTACAGTCCTCAGGACTCTACTCCCTCAGCAGCGTGGTGACCGTGCCCTCCAGCAG
CTTGGGCACCCAGACCTACATCTGCAACGTGAATCACAAGCCCAGCAACACCAAGGTGGA
CAAGAAAGTTGGTGAGAGGCCAGCACAGGGAGGGAGGGTGTCTGCTGGAAGCCAGGCTCA
GCGCTCCTGCCTGGACGCATCCCGGCTATGCAGCCCCAGTCCAGGGCAGCAAGGCAGGCC
CCGTCTGCCTCTTCACCCGGAGGCCTCTGCCCGCCCCACTCATGCTCAGGGAGAGGGTCT
TCTGGCTTTTTCCCCAGGCTCTGGGCAGGCACAGGCTAGGTGCCCCTAACCCAGGCCCTG
CACACAAAGGGGCAGGTGCTGGGCTCAGACCTGCCAAGAGCCATATCCGGGAGGACCCTG
CCCCTGACCTAAGCCCACCCCAAAGGCCAAACTCTCCACTCCCTCAGCTCGGACACCTTC
TCTCCTCCCAGATTCCAGTAACTCCCAATCTTCTCTCTGCAGAGCCCAAATCTTGTGACA
AAACTCACACATGCCCACCGTGCCCAGGTAAGCCAGCCCAGGCCTCGCCTCCAGCTCAAG
GCGGGACAGGTGCCCTAGAGTAGCCTGCATCCAGGGACAGGCCCCAGCCGGGTGCTGACA
CGTCCACCTCCATCTCTTCCTCAGCACCTGAACTCCTGGGGGGACCGTCAGTCTTCCTCT
```

FIGURE 15 (cont.)

```
TCCCCCCAAAACCCAAGGACACCCTCATGATCTCCCGGACCCCTGAGGTCACATGCGTGG
TGGTGGACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTACCGTGTGG
TCAGCGTCCTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAAGGTGGGA
CCCGTGGGGTGCGAGGGCCACATGGACAGAGGCCGGCTCGGCCCACCCTCTGCCCTGAGA
GTGACCGCTGTACCAACCTCTGTCCCTACAGGGCAGCCCCGAGAACCACAGGTGTACACC
CTGCCCCCATCCCGGGATGAGCTGACCAAGAACCAGGTCAGCCTGACCTGCCTGGTCAAA
GGCTTCTATCCCAGCGACATCGCCGTGGAGTGGGAGAGCAATGGGCAGCCGGAGAACAAC
TACAAGACCACGCCTCCCGTGCTGGACTCCGACGGCTCCTTCTTCCTCTACAGCAAGCTC
ACCGTGGACAAGAGCAGGTGGCAGCAGGGGAACGTCTTCTCATGCTCCGTGATGCATGAG
GCTCTGCACAACCACTACACGCAGAAGAGCCTCTCCCTGTCTCCGGGTAAATGA
```

FIGURE 16

(SEQ ID NO: 161), WT heavy chain, variable region underlined

<u>EVKLEESGGGLVQPGGSMKLSCVASGFIFSNHWMNWVRQSPEKGLEWVAEIRSKSINSAT
HYAESVKGRFTISRDDSKSAVYLQMTDLRTEDTGVYYCSRNYYGSTYDYWGQGTTLTVSS</u>
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFFLYSKLTVDKSRW
QQGNVFSCSVMHEALHNHYTQKSLSLSPGK

FIGURE 17

(SEQ ID NO: 162), WT L-chain (sequence truncated at Ck gene stop codon)
GAATTCTAAATACATTTTAGAAGTCGATAAACTTAAGTTTGGGGAAACTAGAACTACTCA
AGCTAAAATTAAAAGGTTGAACTCAATAAGTTAAAAGAGGACCTCTCCAGTTTCGGCTGA
ATCCTCAACTTATTTTAGAAATGCAAATTACCCAGGTGGTGTTTTGCTCAGCCTGGACTT
TCGGTTTGGTGGGGCTGGACAGAGTGTTTCAAAACCACTTCTTCAAACCACAGCTACAAG
TTTACCTAGTGGTTTTATTTTCCCTTCCCCAAATAGCCTTGCCACATGACCTGCTTCCTG
CCAGCTGCTGCAGGTGTTCCGGTTCTGATCGGCCATCTTGACTCAACTCAACATTGCTCA
ATTCATTTAAAAATATTTTAAACTTAATTTATTATTGTTAAAAGTCAGTTCTGAATAGGG
TATGAGAGAGCCTCACTCCCATTCCTCGGTTAAACTTTAAGTAATGTCAGTTCTACACAA
ACAAGACCTCAAATTGATTGACAAAATTTTGGACATTTAAAAAAATGAGTACTTGAAAA
CCCTCTCACATTTTAAAGTCACAGTATTTAACTATTTTTCCTAGGAACCAACTTAAGAGT
AAAAGCAACATCTTCTAATATTCCATACACATACTTCTGTGTTCCTTTGAAAGCTGGACT
TTTGCAGGCTCCACCAGACCTCTCTAGAGTCGACCTGCAGCCCAAGCTTATGAATATGCA
AATCCTCTGAATCTACATGGTAAATATAGGTTTGTCTATACCACAAACAGAAAACATGA
GATCACAGTTCTCTCTACAGTTACTGAGCACACAGGACCTCACCATGGATGGAGCTGTA
TCATCCTCTTCTTGGTAGCAACAGCTACAGGTAAGGGGCTCACAGTAGCAGGCTTGAGGT
CTGGACATATATATGGGTGACAATGACATCCACTTTGCCTTTCTCTCCACAGGTGTCCAC
TCCGACATCTTGCTGACTCAGTCTCCAGCCATCCTGTCTGTGAGTCCAGGAGAAAGAGTC
AGTTTCTCCTGCAGGGCCAGTCAGTTCGTTGGCTCAAGCATCCACTGGTATCAGCAAAGA
ACAAATGGTTCTCCAAGGCTTCTCATAAAGTATGCTTCTGAGTCTATGTCTGGCATCCCT
TCTAGATTTAGTGGCAGTGGATCAGGGACAGATTTTACTCTTAGCATCAACACTGTGGAG
TCTGAAGATATTGCAGATTATTACTGTCAACAAAGTCATAGCTGGCCATTCACGTTCGGC
TCGGGGACAAATTTGGAAGTAAAACGTGAGTAGAATTTAAACTTTGCTTCCTCAGTTGGA
TCCTGGCAGAGTCTCACAGATGCTTCTGAGACAACATTTGCTTTCAAAAAATGAACCACA
CACATCCTAAAGATCTCAGCCACTTCCCATGTTTCATTTTATGTTACAGCAAACATCACA
ACAATCATTCCTACAGATCACCACTGCATGTGATCAATAAAATAGTTTTTGCAACAATGG
TACTTATGATAATCATCTTTTATTGTTTACAAATACTGCTTTACAATAGTTATTCGGTTG
CACTGTTCATATTAGATTTCCAATTAGCTCACTTAGGAACATAAGTCCCTCGAACAGCTC
AGTCATCTTTTTCATTCCTGTTTCTATCCCCTACATCTCTTTCCTTTGCAGACGACTATC
TCCTACACTGAAACAGGAAAGCTAGCTTTTTTTTTTCAGTGCTATTTAATTATTTCAATA
TCCTCTCATCAAATGTATTTAAATAACAAAAGCTCAACCAAAAGAAAGAAATATGTAAT
TCTTTCAGAGTAAAAATCACACCCATGACCTGGCCACTGAGGGCTTGATCAATTCACTTT
GAATTGGCATTAAATACCATTAAGGTATATTAACTGATTTAAAATAAGATATATTCGT
GACCATGTTTTAACTTTCAAAATGTAGCTGCCAGTGTGTGATTTTATTTCAGTTGTAC
AAAATATCTAAACCTATAGCAATGTGATTAATAAAAACTTAAACATATTTTCCAGTACCT
TAATTCTGTGATAGGAAAATTTTAATCTGAGTATTTAATTTCATAATCTCTAAAATAGT
TTAATGATTTGTCATTGTGTTGCTGTCGTTTACCCCAGCTGATCTCAAAGTGATATTTA
AGGAGATTATTTTGGTCTGCAACAACTTGATAGGACTATTTAGGGCCTTTTAAAGCTC
TATTAAAACTAACTTACAACGATTCAAAACTGTTTTAAACTATTTCAAAATGATTTTAGA
GCCTTTTGAAAACTCTTTTAAACACTTTTTAAACTCTATTAAAACTAATAAGATAACTTG
AAATAATTTTCATGTCAAATACATTAACTGTTTAATGTTTAAATGCCAGATGAAAAATGT
AAAGCTATCAAGAATTCACCCAGATAGGAGTATCTTCATAGCATGTTTTTCCCTGCTTAT
TTTCCAGTGATCACATTATTTTGCTACCATGGTTATTTTATACAATTATCTGAAAAAAT
TAGTTATGAAGATTAAAAGAGAAGAAAATATTAAACATAAGAGATTCAGTCTTTCATGTT

FIGURE 17 (cont.)

```
GAACTGCTTGGTTAACAGTGAAGTTAGTTTTAAAAAAAAAAAAAAACTATTTCTGTTATCA
GCTGACTTCTCCCTATCTGTTGACTTCTCCCAGCAAAAGATTCTTATTTTACATTTTAAC
TACTGCTCTCCCACCCAACGGGTGGAATCCCCCAGAGGGGGATTTCCAAGAGGCCACCTG
GCAGTTGCTGAGGGTCAGAAGTGAAGCTAGCCACTTCCTCTTAGGCAGGTGGCCAAGATT
ACAGTTGACCTCTCCTGGTATGGCTGAAAATTGCTGCATATGGTTACAGGCCTTGAGGCC
TTTGGGAGGGCTTAGAGAGTTGCTGGAACAGTCAGAAGGTGGAGGGGCTGACACCACCCA
GGCGCAGAGGCAGGGCTCAGGGCCTGCTCTGCAGGGAGGTTTTAGCCCAGCCCAGCCAAA
GTAACCCCCGGGAGCCTGTTATCCCAGCACAGTCCTGGAAGAGGCACAGGGGAAATAAAA
GCGGACGGAGGCTTTCCTTGACTCAGCCGCTGCCTGGTCTTCTTCAGACCTGTTCTGAAT
TCTAAACTCTGAGGGGTCGGATGACGTGGCCATTCTTTGCCTAAAGCATTGAGTTTACT
GCAAGGTCAGAAAAGCATGCAAAGCCCTCAGAATGGCTGCAAAGAGCTCCAACAAAACAA
TTTAGAACTTTATTAAGGAATAGGGGGAAGCTAGGAAGAAACTCAAAACATCAAGATTTT
AAATACGCTTCTTGGTCTCCTTGCTATAATTATCTGGGATAAGCATGCTGTTTTCTGTCT
GTCCCTAACATGCCCTGTGATTATCCGCAAACAACACACCCAAGGGCAGAACTTTGTTAC
TTAAACACCATCCTGTTTGCTTCTTTCCTCAGGAACTGTGGCTGCACCATCTGTCTTCAT
CTTCCCGCCATCTGATGAGCAGTTGAAATCTGGAACTGCCTCTGTTGTGTGCCTGCTGAA
TAACTTCTATCCCAGAGAGGCCAAAGTACAGTGGAAGGTGGATAACGCCCTCCAATCGGG
TAACTCCCAGGAGAGTGTCACAGAGCAGGACAGCAAGGACAGCACCTACAGCCTCAGCAG
CACCCTGACGCTGAGCAAAGCAGACTACGAGAACACAAAGTCTACGCCTGCGAAGTCAC
CCATCAGGGCCTGAGCTCGCCCGTCACAAAGAGCTTCAACAGGGGAGAGTGTTAG
```

FIGURE 18

(SEQ ID NO: 163), light chain, variable region underlined

<u>EVKLEESGGGLVQPGGSMKLSCVASGFIFSNHWMNWVRQSPEKGLEWVAEIRSKSINSAT
HYAESVKGRFTISRDDSKSAVYLQMTDLRTEDTGVYYCSRNYYGSTYDYWGQGTTLTVSS</u>
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFFLYSKLTVDKSRW
QQGNVFSCSVMHEALHNHYTQKSLSLSPGK

FIGURE 19

(SEQ ID NO: 164), heavy chain constant region

ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFFLYSKLTVDKSRW
QQGNVFSCSVMHEALHNHYTQKSLSLSPGK

FIGURE 20

(SEQ ID NO: 165), light chain constant region

TVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

SEQUENCE LISTING

```
<160> NUMBER OF SEQ ID NOS: 165

<210> SEQ ID NO 1
<211> LENGTH: 120
<212> TYPE: PRT
<213> ORGANISM: mus musculus

<400> SEQUENCE: 1

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn His
             20                  25                  30

Trp Met Asn Trp Val Arg Gln Ser Pro Glu Lys Gly Leu Glu Trp Val
         35                  40                  45

Ala Glu Ile Arg Ser Lys Ser Ile Asn Ser Ala Thr His Tyr Ala Glu
     50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser
        115                 120

<210> SEQ ID NO 2
<211> LENGTH: 120
<212> TYPE: PRT
<213> ORGANISM: mus musculus

<400> SEQUENCE: 2

Glu Val Lys Leu Glu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn His
             20                  25                  30

Trp Met Asn Trp Val Arg Gln Ser Pro Glu Lys Gly Leu Glu Trp Val
         35                  40                  45
```

```
Ala Glu Ile Arg Ser Lys Ser Ile Asn Ser Ala Thr His Tyr Ala Glu
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Gly Val Tyr
                85                  90                  95

Tyr Cys Ser Arg Asn Tyr Tyr Gly Ser Thr Tyr Asp Tyr Trp Gly Gln
                100                 105                 110

Gly Thr Thr Val Thr Val Ser Ser
            115                 120

<210> SEQ ID NO 3
<211> LENGTH: 120
<212> TYPE: PRT
<213> ORGANISM: mus musculus

<400> SEQUENCE: 3

Glu Val Lys Leu Glu Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
                20                  25                  30

Trp Met Asn Trp Val Arg Gln Ser Pro Glu Lys Gly Leu Glu Trp Val
            35                  40                  45

Ala Glu Thr Arg Ser Lys Ser Thr Asn Ser Ala Thr His Tyr Ala Glu
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Gly Val Tyr
                85                  90                  95

Tyr Cys Ser Arg Asn Tyr Tyr Gly Ser Thr Tyr Asp Tyr Trp Gly Gln
                100                 105                 110

Gly Thr Thr Val Thr Val Ser Ser
            115                 120

<210> SEQ ID NO 4
<211> LENGTH: 120
<212> TYPE: PRT
<213> ORGANISM: mus musculus

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
                20                  25                  30

Trp Met Asn Trp Val Arg Gln Ser Pro Glu Lys Gly Leu Glu Trp Val
            35                  40                  45

Ala Glu Thr Arg Ser Lys Ser Thr Asn Ser Ala Thr His Tyr Ala Asp
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ser Arg Asn Tyr Tyr Gly Ser Thr Tyr Asp Tyr Trp Gly Gln
                100                 105                 110

Gly Thr Leu Val Thr Val Ser Ser
            115                 120
```

<210> SEQ ID NO 5
<211> LENGTH: 108
<212> TYPE: PRT
<213> ORGANISM: mus musculus

<400> SEQUENCE: 5

Asp Ile Gln Leu Thr Gln Ser Pro Asp Thr Ser Ser Ala Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Phe
                85                  90                  95

Thr Phe Gly Ser Gly Thr Asn Val Glu Val Lys Arg
            100                 105

<210> SEQ ID NO 6
<211> LENGTH: 108
<212> TYPE: PRT
<213> ORGANISM: mus musculus

<400> SEQUENCE: 6

Asp Ile Gln Leu Thr Gln Ser Pro Asp Thr Ser Ser Ala Ser Pro Gly
1               5                   10                  15

Glu Arg Ala Ser Phe Ser Cys Arg Ala Ser Gln Phe Val Gly Ser Ser
            20                  25                  30

Ile His Trp Tyr Gln His Thr Thr Asn Gly Ser Pro Arg Leu Leu Ile
        35                  40                  45

Lys Tyr Ala Ser Glu Ser Met Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser His Ser Trp Pro Phe
                85                  90                  95

Thr Phe Gly Ser Gly Thr Asn Leu Glu Val Lys Arg
            100                 105

<210> SEQ ID NO 7
<211> LENGTH: 108
<212> TYPE: PRT
<213> ORGANISM: mus musculus

<400> SEQUENCE: 7

Asp Ile Gln Leu Thr Gln Ser Pro Asp Thr Ser Ser Ala Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Val Pro Ser Arg Phe Ser Gly
    50                  55                  60

```
Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Ser His Ser Trp Pro Phe
                 85                  90                  95

Thr Phe Gly Gly Gly Thr Lys Val Glu Ile Lys Arg
            100                 105
```

<210> SEQ ID NO 8
<211> LENGTH: 108
<212> TYPE: PRT
<213> ORGANISM: mus musculus

<400> SEQUENCE: 8

```
Asp Ile Gln Leu Thr Gln Ser Pro Asp Thr Ser Ala Ser Pro Gly
 1               5                  10                  15

Glu Arg Ala Ser Phe Ser Cys Arg Ala Ser Gln Phe Val Gly Ser Ser
                 20                  25                  30

Ile His Trp Tyr Gln His Thr Thr Asn Gly Ser Pro Arg Leu Leu Ile
             35                  40                  45

Lys Tyr Ala Ser Glu Ser Met Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Ser His Ser Trp Pro Phe
                 85                  90                  95

Thr Phe Gly Gly Gly Thr Lys Val Glu Ile Lys Arg
            100                 105
```

<210> SEQ ID NO 9
<211> LENGTH: 120
<212> TYPE: PRT
<213> ORGANISM: mus musculus

<400> SEQUENCE: 9

```
Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Ile Phe Ser Asn His
                 20                  25                  30

Trp Met Asn Trp Val Arg Gln Ser Pro Glu Lys Gly Leu Glu Trp Val
             35                  40                  45

Ala Glu Ile Arg Ser Lys Ser Ile Asn Ser Ala Thr His Tyr Ala Glu
 50                  55                  60

Ser Val Lys Gly Arg Phe Thr Ile Ser Arg Asp Asp Ser Lys Ser Ala
 65                  70                  75                  80

Val Tyr Leu Gln Met Thr Asp Leu Arg Thr Glu Asp Thr Gly Val Tyr
                 85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser
        115                 120
```

<210> SEQ ID NO 10
<211> LENGTH: 109
<212> TYPE: PRT
<213> ORGANISM: mus musculus

<400> SEQUENCE: 10

```
Asp Ile Leu Leu Thr Gln Ser Pro Ala Ile Leu Ser Val Ser Pro Gly
```

```
                        1               5                  10                 15
Glu Arg Val Ser Phe Ser Cys Arg Ala Ser Gln Phe Val Gly Ser Ser
                    20                 25                 30

Ile His Trp Tyr Gln Gln Arg Thr Asn Gly Ser Pro Arg Leu Leu Ile
                    35                 40                 45

Lys Tyr Ala Ser Glu Ser Met Ser Gly Ile Pro Ser Arg Phe Ser Gly
                    50                 55                 60

Ser Gly Ser Gly Thr Asp Phe Thr Leu Ser Ile Asn Thr Val Glu Ser
 65                 70                 75                 80

Glu Asp Ile Ala Asp Tyr Tyr Cys Gln Gln Ser His Ser Trp Pro Phe
                    85                 90                 95

Thr Phe Gly Ser Gly Thr Asn Leu Glu Val Lys Arg Glu
                   100                105

<210> SEQ ID NO 11
<211> LENGTH: 132
<212> TYPE: PRT
<213> ORGANISM: Artificial Sequence
<220> FEATURE:
<223> OTHER INFORMATION: Modified antibody variable region

<400> SEQUENCE: 11

Glu Val Lys Leu Glu Glu Ser Gly Gly Gly Leu Val Gln Pro Gly Gly
 1               5                  10                 15

Ser Met Lys Leu Ser Cys Val Ala Ser Gly Phe Ile Phe Ser Asn His
                    20                 25                 30

Trp Met Asn Trp Val Arg Gln Ser Pro Glu Lys Gly Leu Glu Trp Val
                    35                 40                 45

Ala Glu Ile Arg Ser Lys Ser Ile Asn Ser Ala Thr His Tyr Ala Glu
                    50                 55                 60

Ser Val Lys Gly Arg Phe Thr Ile Ser Arg Asp Asp Ser Lys Ser Ala
 65                 70                 75                 80

Val Tyr Leu Gln Met Thr Asp Leu Arg Thr Glu Asp Thr Gly Val Tyr
                    85                 90                 95

Tyr Cys Ser Arg Asn Tyr Tyr Gly Ser Thr Tyr Asp Tyr Trp Gly Gln
                   100                105                110

Gly Thr Thr Leu Thr Val Ser Ser Ala Ser Thr Lys Gly Pro Ser Val
                   115                120                125

Phe Pro Leu Ala
           130

<210> SEQ ID NO 12
<211> LENGTH: 117
<212> TYPE: PRT
<213> ORGANISM: Artificial Sequence
<220> FEATURE:
<223> OTHER INFORMATION: Modified antibody variable region

<400> SEQUENCE: 12

Asp Ile Leu Leu Thr Gln Ser Pro Ala Ile Leu Ser Val Ser Pro Gly
 1               5                  10                 15

Glu Arg Val Ser Phe Ser Cys Arg Ala Ser Gln Phe Val Gly Ser Ser
                    20                 25                 30

Ile His Trp Tyr Gln Gln Arg Thr Asn Gly Ser Pro Arg Leu Leu Ile
                    35                 40                 45

Lys Tyr Ala Ser Glu Ser Met Ser Gly Ile Pro Ser Arg Phe Ser Gly
                    50                 55                 60
```

```
Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys Arg Thr Val Ala Ala
            100                 105                 110

Pro Ser Val Phe Ile
        115

<210> SEQ ID NO 13
<211> LENGTH: 16
<212> TYPE: PRT
<213> ORGANISM: mus musculus

<400> SEQUENCE: 13

Gly Leu Val Gln Pro Gly Gly Ser Met Lys Leu Ser Cys Val Ala Ser
 1               5                  10                  15

<210> SEQ ID NO 14
<211> LENGTH: 13
<212> TYPE: PRT
<213> ORGANISM: mus musculus

<400> SEQUENCE: 14

Trp Val Ala Glu Ile Arg Ser Lys Ser Ile Asn Ser Ala
 1               5                  10

<210> SEQ ID NO 15
<211> LENGTH: 18
<212> TYPE: PRT
<213> ORGANISM: mus musculus

<400> SEQUENCE: 15

Ser Arg Asp Asp Ser Lys Ser Ala Val Tyr Leu Gln Met Thr Asp Leu
 1               5                  10                  15

Arg Thr

<210> SEQ ID NO 16
<211> LENGTH: 21
<212> TYPE: PRT
<213> ORGANISM: mus musculus

<400> SEQUENCE: 16

Arg Asn Tyr Tyr Gly Ser Thr Tyr Asp Tyr Trp Gly Gln Gly Thr Thr
 1               5                  10                  15

Leu Thr Val Ser Ser
            20

<210> SEQ ID NO 17
<211> LENGTH: 21
<212> TYPE: PRT
<213> ORGANISM: mus musculus

<400> SEQUENCE: 17

Asp Ile Leu Leu Thr Gln Ser Pro Ala Ile Leu Ser Val Ser Pro Gly
 1               5                  10                  15

Glu Arg Val Ser Phe
            20

<210> SEQ ID NO 18
<211> LENGTH: 12
<212> TYPE: PRT
```

```
<213> ORGANISM: mus musculus

<400> SEQUENCE: 18

His Trp Tyr Gln Gln Arg Thr Asn Gly Ser Pro Arg
 1               5                   10

<210> SEQ ID NO 19
<211> LENGTH: 14
<212> TYPE: PRT
<213> ORGANISM: mus musculus

<400> SEQUENCE: 19

Leu Ile Lys Tyr Ala Ser Glu Ser Met Ser Gly Ile Pro Ser
 1               5                   10

<210> SEQ ID NO 20
<211> LENGTH: 21
<212> TYPE: PRT
<213> ORGANISM: mus musculus

<400> SEQUENCE: 20

Asp Phe Thr Leu Ser Ile Asn Thr Val Glu Ser Glu Asp Ile Ala Asp
 1               5                   10                  15

Tyr Tyr Cys Gln Gln
             20

<210> SEQ ID NO 21
<211> LENGTH: 13
<212> TYPE: PRT
<213> ORGANISM: Artificial Sequence
<220> FEATURE:
<223> OTHER INFORMATION: Immunogenic peptide

<400> SEQUENCE: 21

Pro Lys Tyr Val Lys Gln Asn Thr Leu Lys Leu Ala Thr
 1               5                   10

<210> SEQ ID NO 22
<211> LENGTH: 16
<212> TYPE: PRT
<213> ORGANISM: Artificial Sequence
<220> FEATURE:
<223> OTHER INFORMATION: Immunogenic peptide

<400> SEQUENCE: 22

Lys Val Val Asp Gln Ile Lys Lys Ile Ser Lys Pro Val Gln His His
 1               5                   10                  15

<210> SEQ ID NO 23
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 23
gaagtgaagc tggaggagtc tggaggcggc ttggtgcaac                            40

<210> SEQ ID NO 24
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 24
```

```
ctggaggctc catgaaactc tcctgtgttg cctctggatt                         40

<210> SEQ ID NO 25
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 25
cattttcagt aaccactgga tgaactgggt ccgccagtct                         40

<210> SEQ ID NO 26
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 26
ccagagaagg ggcttgagtg ggttgctgaa attagatcaa                         40

<210> SEQ ID NO 27
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 27
aatcgattaa ttctgcaaca cattatgcgg agtctgtgaa                         40

<210> SEQ ID NO 28
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 28
agggaggttc accatctcaa gagatgattc caaaagtgct                         40

<210> SEQ ID NO 29
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 29
gtgtacctgc aaatgaccga cctgagaact gaagacactg                         40

<210> SEQ ID NO 30
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 30
gcgtttatta ctgttccagg aattactacg gtagtaccta                         40

<210> SEQ ID NO 31
<211> LENGTH: 42
<212> TYPE: DNA
```

```
<213> ORGANISM: Artificial Sequence
<220> FEATURE:
<223> OTHER INFORMATION: synthetic polynucleotide

<400> SEQUENCE: 31
cgactactgg ggccaaggca ccactctcac agtgtcctca gg                          42

<210> SEQ ID NO 32
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 32
cctgaggaca ctgtgagagt gg                                                22

<210> SEQ ID NO 33
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 33
tgccttggcc ccagtagtcg taggtactac cgtagtaatt                             40

<210> SEQ ID NO 34
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 34
cctggaacag taataaacgc cagtgtcttc agttctcagg                             40

<210> SEQ ID NO 35
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 35
tcggtcattt gcaggtacac agcacttttg gaatcatctc                             40

<210> SEQ ID NO 36
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 36
ttgagatggt gaacctccct ttcacagact ccgcataatg                             40

<210> SEQ ID NO 37
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 37
tgttgcagaa ttaatcgatt ttgatctaat ttcagcaacc                             40
```

```
<210> SEQ ID NO 38
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 38
cactcaagcc ccttctctgg agactggcgg acccagttca                              40

<210> SEQ ID NO 39
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 39
tccagtggtt actgaaaatg aatccagagg caacacagga                              40

<210> SEQ ID NO 40
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 40
gagtttcatg gagcctccag gttgcaccaa gccgcctcca                              40

<210> SEQ ID NO 41
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 41
gactcctcca gcttcacttc                                                    20

<210> SEQ ID NO 42
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 42
agactcctcc agcttcactt cggagtggac acctgtggag ag                           42

<210> SEQ ID NO 43
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 43
accactctca cagtgtcctc aggtgagtcc ttacaacctc tc                           42

<210> SEQ ID NO 44
<211> LENGTH: 24
<212> TYPE: DNA
<213> ORGANISM: Artificial Sequence
<220> FEATURE:
```

<223> OTHER INFORMATION: synthetic polynucleotide

<400> SEQUENCE: 44
ttgggatcct ataaatctct ggcc                                          24

<210> SEQ ID NO 45
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 45
gacatcttgc tgactcagtc tccagccatc ctgtctgtga                         40

<210> SEQ ID NO 46
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 46
gtccaggaga aagagtcagt ttctcctgca gggccagtca                         40

<210> SEQ ID NO 47
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 47
gttcgttggc tcaagcatcc actggtatca gcaaagaaca                         40

<210> SEQ ID NO 48
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 48
aatggttctc caaggcttct cataaagtat gcttctgagt                         40

<210> SEQ ID NO 49
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 49
ctatgtctgg catcccttct agatttagtg gcagtggatc                         40

<210> SEQ ID NO 50
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 50
agggacagat tttactctta gcatcaacac tgtggagtct                         40

<210> SEQ ID NO 51
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 51
gaagatattg cagattatta ctgtcaacaa agtcatagct                         40

<210> SEQ ID NO 52
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 52
ggccattcac gttcggctcg gggacaaatt tggaagtaaa                         40

<210> SEQ ID NO 53
<211> LENGTH: 50
<212> TYPE: DNA
<213> ORGANISM: Artificial Sequence
<220> FEATURE:
<223> OTHER INFORMATION: synthetic polynucleotide

<400> SEQUENCE: 53
acgtgagtag aatttaaact ttgcttcctc agttggatcc tggcagagtc              50

<210> SEQ ID NO 54
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 54
gactctgcca ggatccaact gaggaagcaa                                    30

<210> SEQ ID NO 55
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 55
agtttaaatt ctactcacgt tttacttcca aatttgtccc                         40

<210> SEQ ID NO 56
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 56
cgagccgaac gtgaatggcc agctatgact ttgttgacag                         40

<210> SEQ ID NO 57
<211> LENGTH: 40
<212> TYPE: DNA
<213> ORGANISM: Artificial Sequence
<220> FEATURE:
<223> OTHER INFORMATION: synthetic polynucleotide
<210> SEQ ID NO 57
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 57
taataatctg caatatcttc agactccaca gtgttgatgc                    40

<210> SEQ ID NO 58
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 58
taagagtaaa atctgtccct gatccactgc cactaaatct                    40

<210> SEQ ID NO 59
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 59
agaagggatg ccagacatag actcagaagc atactttatg                    40

<210> SEQ ID NO 60
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 60
agaagccttg gagaaccatt tgttctttgc tgataccagt                    40

<210> SEQ ID NO 61
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 61
ggatgcttga gccaacgaac tgactggccc tgcaggagaa                    40

<210> SEQ ID NO 62
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 62
actgactctt tctcctggac tcacagacag gatggctgga                    40

<210> SEQ ID NO 63
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 63
gactgagtca gcaagatgtc                                          20

<210> SEQ ID NO 64
<211> LENGTH: 29

```
<212> TYPE: DNA
<213> ORGANISM: Artificial Sequence
<220> FEATURE:
<223> OTHER INFORMATION: synthetic polynucleotide

<400> SEQUENCE: 64
ttacgccaag cttatgaata tgcaaatcc                                          29

<210> SEQ ID NO 65
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 65
agactgagtc agcaagatgt cggagtggac acctgtggag ag                           42

<210> SEQ ID NO 66
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 66
gacatccagc tgactcagtc tccagacacc tcctctgcca                              40

<210> SEQ ID NO 67
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 67
ctatgtctgg cgtgccttct agatttagtg gcagtggatc                              40

<210> SEQ ID NO 68
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 68
agggacagat tttactctta ccatcaactc cctggaggcc                              40

<210> SEQ ID NO 69
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 69
gaagatgccg caacctatta ctgtcaacaa agtcatagct                              40

<210> SEQ ID NO 70
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 70
```
ggccattcac gttcggctcg gggacaaatg tggaagtaaa          40

<210> SEQ ID NO 71
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 71
agtttaaatt ctactcacgt tttacttcca catttgtccc          40

<210> SEQ ID NO 72
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 72
taataggttg cggcatcttc ggcctccagg gagttgatgg          40

<210> SEQ ID NO 73
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 73
agaaggcacg ccagacatag actcagaagc atactttatg          40

<210> SEQ ID NO 74
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 74
actgactctt tctcctggac tggcagagga ggtgtctgga          40

<210> SEQ ID NO 75
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 75
gactgagtca gctggatgtc          20

<210> SEQ ID NO 76
<211> LENGTH: 42
<212> TYPE: DNA
<213> ORGANISM: Artificial Sequence
<220> FEATURE:
<223> OTHER INFORMATION: synthetic polynucleotide

<400> SEQUENCE: 76
agactgagtc agctggatgt cggagtggac acctgtggag ag          42

<210> SEQ ID NO 77
<211> LENGTH: 80
<212> TYPE: DNA
<213> ORGANISM: Artificial Sequence

```
<220> FEATURE:
<223> OTHER INFORMATION: synthetic polynucleotide

<400> SEQUENCE: 77
ggatccaact gaggaagcaa agtttaaatt ctactcacgt tgatttccca cctttgtccc    60
gccgccgaac gtgaatggcc                                                80

<210> SEQ ID NO 78
<211> LENGTH: 33
<212> TYPE: DNA
<213> ORGANISM: Artificial Sequence
<220> FEATURE:
<223> OTHER INFORMATION: synthetic polynucleotide

<400> SEQUENCE: 78
agtccaggag aaagagccag tttctcctgc agg                                 33

<210> SEQ ID NO 79
<211> LENGTH: 33
<212> TYPE: DNA
<213> ORGANISM: Artificial Sequence
<220> FEATURE:
<223> OTHER INFORMATION: synthetic polynucleotide

<400> SEQUENCE: 79
cctgcaggag aaactggctc tttctcctgg act                                 33

<210> SEQ ID NO 80
<211> LENGTH: 35
<212> TYPE: DNA
<213> ORGANISM: Artificial Sequence
<220> FEATURE:
<223> OTHER INFORMATION: synthetic polynucleotide

<400> SEQUENCE: 80
ccactggtat cagcacacaa caaatggttc tccaa                               35

<210> SEQ ID NO 81
<211> LENGTH: 35
<212> TYPE: DNA
<213> ORGANISM: Artificial Sequence
<220> FEATURE:
<223> OTHER INFORMATION: synthetic polynucleotide

<400> SEQUENCE: 81
ttggagaacc atttgttgtg tgctgatacc agtgg                               35

<210> SEQ ID NO 82
<211> LENGTH: 62
<212> TYPE: DNA
<213> ORGANISM: Artificial Sequence
<220> FEATURE:
<223> OTHER INFORMATION: synthetic polynucleotide

<400> SEQUENCE: 82
gtctcaggga gcctccaggt tgcaccaagc cgcctccaga ctccaccagc tgcacttcgg    60
ag                                                                   62

<210> SEQ ID NO 83
<211> LENGTH: 62
<212> TYPE: DNA
<213> ORGANISM: Artificial Sequence
<220> FEATURE:
<223> OTHER INFORMATION: synthetic polynucleotide
```

<400> SEQUENCE: 83
aacctggagg ctccctgaga ctctcctgtg ctgcctctgg attcactttc agtaaccact    60
gg    62

<210> SEQ ID NO 84
<211> LENGTH: 41
<212> TYPE: DNA
<213> ORGANISM: Artificial Sequence
<220> FEATURE:
<223> OTHER INFORMATION: synthetic polynucleotide

<400> SEQUENCE: 84
aggctgttca tttgcaggta cagagaattt ttggaatcat c    41

<210> SEQ ID NO 85
<211> LENGTH: 50
<212> TYPE: DNA
<213> ORGANISM: Artificial Sequence
<220> FEATURE:
<223> OTHER INFORMATION: synthetic polynucleotide

<400> SEQUENCE: 85
tacctgcaaa tgaacagcct gaaaactgaa gacactgccg tttattactg    50

<210> SEQ ID NO 86
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 86
gaaactagat caaaatcgac taattctgca    30

<210> SEQ ID NO 87
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 87
attagtcgat tttgatctag tttcagcaac    30

<210> SEQ ID NO 88
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 88
cacattatgc ggactctgtg aaaggg    26

<210> SEQ ID NO 89
<211> LENGTH: 26
<212> TYPE: DNA
<213> ORGANISM: Artificial Sequence
<220> FEATURE:
<223> OTHER INFORMATION: synthetic polynucleotide

<400> SEQUENCE: 89
ccctttcaca gagtccgcat aatgtg    26

<210> SEQ ID NO 90
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 90
ggccaaggca cccttgtcac agtgtcctca                30

<210> SEQ ID NO 91
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 91
tgaggacact gtgacaaggg tgccttggcc                30

<210> SEQ ID NO 92
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 92
gccaaggcac cactgtcaca gtgtcctcag g               31

<210> SEQ ID NO 93
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 93
cctgaggaca ctgtgacagt ggtgccttgg c               31

<210> SEQ ID NO 94
<211> LENGTH: 13
<212> TYPE: PRT
<213> ORGANISM: mus musculus

<400> SEQUENCE: 94

Val Lys Leu Glu Glu Ser Gly Gly Gly Leu Val Gln Pro
 1               5                  10

<210> SEQ ID NO 95
<211> LENGTH: 13
<212> TYPE: PRT
<213> ORGANISM: mus musculus

<400> SEQUENCE: 95

Gly Gly Leu Val Gln Pro Gly Gly Ser Met Lys Leu Ser
 1               5                  10

<210> SEQ ID NO 96
<211> LENGTH: 13
<212> TYPE: PRT
<213> ORGANISM: mus musculus

<400> SEQUENCE: 96

Gly Leu Val Gln Pro Gly Gly Ser Met Lys Leu Ser Cys
 1               5                  10

<210> SEQ ID NO 97
<211> LENGTH: 13
<212> TYPE: PRT
<213> ORGANISM: mus musculus

<400> SEQUENCE: 97

Gly Ser Met Lys Leu Ser Cys Val Ala Ser Gly Phe Ile
1               5                   10

<210> SEQ ID NO 98
<211> LENGTH: 13
<212> TYPE: PRT
<213> ORGANISM: mus musculus

<400> SEQUENCE: 98

Met Lys Leu Ser Cys Val Ala Ser Gly Phe Ile Phe Ser
1               5                   10

<210> SEQ ID NO 99
<211> LENGTH: 13
<212> TYPE: PRT
<213> ORGANISM: mus musculus

<400> SEQUENCE: 99

Ser Cys Val Ala Ser Gly Phe Ile Phe Ser Asn His Trp
1               5                   10

<210> SEQ ID NO 100
<211> LENGTH: 13
<212> TYPE: PRT
<213> ORGANISM: mus musculus

<400> SEQUENCE: 100

Ser Gly Phe Ile Phe Ser Asn His Trp Met Asn Trp Val
1               5                   10

<210> SEQ ID NO 101
<211> LENGTH: 13
<212> TYPE: PRT
<213> ORGANISM: mus musculus

<400> SEQUENCE: 101

Gly Phe Ile Phe Ser Asn His Trp Met Asn Trp Val Arg
1               5                   10

<210> SEQ ID NO 102
<211> LENGTH: 13
<212> TYPE: PRT
<213> ORGANISM: mus musculus

<400> SEQUENCE: 102

Phe Ile Phe Ser Asn His Trp Met Asn Trp Val Arg Gln
1               5                   10

<210> SEQ ID NO 103
<211> LENGTH: 13
<212> TYPE: PRT
<213> ORGANISM: mus musculus

<400> SEQUENCE: 103

Asn His Trp Met Asn Trp Val Arg Gln Ser Pro Glu Lys
1               5                   10

<210> SEQ ID NO 104
<211> LENGTH: 13
<212> TYPE: PRT
<213> ORGANISM: mus musculus

<400> SEQUENCE: 104

His Trp Met Asn Trp Val Arg Gln Ser Pro Glu Lys Gly
1               5                   10

<210> SEQ ID NO 105
<211> LENGTH: 13
<212> TYPE: PRT
<213> ORGANISM: mus musculus

<400> SEQUENCE: 105

Met Asn Trp Val Arg Gln Ser Pro Glu Lys Gly Leu Glu
1               5                   10

<210> SEQ ID NO 106
<211> LENGTH: 13
<212> TYPE: PRT
<213> ORGANISM: mus musculus

<400> SEQUENCE: 106

Asn Trp Val Arg Gln Ser Pro Glu Lys Gly Leu Glu Trp
1               5                   10

<210> SEQ ID NO 107
<211> LENGTH: 13
<212> TYPE: PRT
<213> ORGANISM: mus musculus

<400> SEQUENCE: 107

Lys Gly Leu Glu Trp Val Ala Glu Ile Arg Ser Lys Ser
1               5                   10

<210> SEQ ID NO 108
<211> LENGTH: 13
<212> TYPE: PRT
<213> ORGANISM: mus musculus

<400> SEQUENCE: 108

Leu Glu Trp Val Ala Glu Ile Arg Ser Lys Ser Ile Asn
1               5                   10

<210> SEQ ID NO 109
<211> LENGTH: 13
<212> TYPE: PRT
<213> ORGANISM: mus musculus

<400> SEQUENCE: 109

Glu Trp Val Ala Glu Ile Arg Ser Lys Ser Ile Asn Ser
1               5                   10

<210> SEQ ID NO 110
<211> LENGTH: 13
<212> TYPE: PRT
<213> ORGANISM: mus musculus

<400> SEQUENCE: 110

Ala Glu Ile Arg Ser Lys Ser Ile Asn Ser Ala Thr His
1               5                   10

<210> SEQ ID NO 111
<211> LENGTH: 13

-continued

<212> TYPE: PRT
<213> ORGANISM: mus musculus

<400> SEQUENCE: 111

Lys Ser Ile Asn Ser Ala Thr His Tyr Ala Glu Ser Val
1               5                   10

<210> SEQ ID NO 112
<211> LENGTH: 13
<212> TYPE: PRT
<213> ORGANISM: mus musculus

<400> SEQUENCE: 112

Thr His Tyr Ala Glu Ser Val Lys Gly Arg Phe Thr Ile
1               5                   10

<210> SEQ ID NO 113
<211> LENGTH: 13
<212> TYPE: PRT
<213> ORGANISM: mus musculus

<400> SEQUENCE: 113

Glu Ser Val Lys Gly Arg Phe Thr Ile Ser Arg Asp Asp
1               5                   10

<210> SEQ ID NO 114
<211> LENGTH: 13
<212> TYPE: PRT
<213> ORGANISM: mus musculus

<400> SEQUENCE: 114

Gly Arg Phe Thr Ile Ser Arg Asp Asp Ser Lys Ser Ala
1               5                   10

<210> SEQ ID NO 115
<211> LENGTH: 13
<212> TYPE: PRT
<213> ORGANISM: mus musculus

<400> SEQUENCE: 115

Phe Thr Ile Ser Arg Asp Asp Ser Lys Ser Ala Val Tyr
1               5                   10

<210> SEQ ID NO 116
<211> LENGTH: 13
<212> TYPE: PRT
<213> ORGANISM: mus musculus

<400> SEQUENCE: 116

Ser Ala Val Tyr Leu Gln Met Thr Asp Leu Arg Thr Glu
1               5                   10

<210> SEQ ID NO 117
<211> LENGTH: 13
<212> TYPE: PRT
<213> ORGANISM: mus musculus

<400> SEQUENCE: 117

Ala Val Tyr Leu Gln Met Thr Asp Leu Arg Thr Glu Asp
1               5                   10

<210> SEQ ID NO 118
<211> LENGTH: 13
<212> TYPE: PRT
<213> ORGANISM: mus musculus

<400> SEQUENCE: 118

Val Tyr Leu Gln Met Thr Asp Leu Arg Thr Glu Asp Thr
1               5                   10

<210> SEQ ID NO 119
<211> LENGTH: 13
<212> TYPE: PRT
<213> ORGANISM: mus musculus

<400> SEQUENCE: 119

Leu Gln Met Thr Asp Leu Arg Thr Glu Asp Thr Gly Val
1               5                   10

<210> SEQ ID NO 120
<211> LENGTH: 13
<212> TYPE: PRT
<213> ORGANISM: mus musculus

<400> SEQUENCE: 120

Thr Asp Leu Arg Thr Glu Asp Thr Gly Val Tyr Tyr Cys
1               5                   10

<210> SEQ ID NO 121
<211> LENGTH: 13
<212> TYPE: PRT
<213> ORGANISM: mus musculus

<400> SEQUENCE: 121

Thr Gly Val Tyr Tyr Cys Ser Arg Asn Tyr Tyr Gly Ser
1               5                   10

<210> SEQ ID NO 122
<211> LENGTH: 13
<212> TYPE: PRT
<213> ORGANISM: mus musculus

<400> SEQUENCE: 122

Gly Val Tyr Tyr Cys Ser Arg Asn Tyr Tyr Gly Ser Thr
1               5                   10

<210> SEQ ID NO 123
<211> LENGTH: 13
<212> TYPE: PRT
<213> ORGANISM: mus musculus

<400> SEQUENCE: 123

Val Tyr Tyr Cys Ser Arg Asn Tyr Tyr Gly Ser Thr Tyr
1               5                   10

<210> SEQ ID NO 124
<211> LENGTH: 13
<212> TYPE: PRT
<213> ORGANISM: mus musculus

<400> SEQUENCE: 124

Arg Asn Tyr Tyr Gly Ser Thr Tyr Asp Tyr Trp Gly Gln
1               5                   10

<210> SEQ ID NO 125
<211> LENGTH: 13
<212> TYPE: PRT
<213> ORGANISM: mus musculus

<400> SEQUENCE: 125

Asn Tyr Tyr Gly Ser Thr Tyr Asp Tyr Trp Gly Gln Gly
 1               5                  10

<210> SEQ ID NO 126
<211> LENGTH: 13
<212> TYPE: PRT
<213> ORGANISM: mus musculus

<400> SEQUENCE: 126

Ser Thr Tyr Asp Tyr Trp Gly Gln Gly Thr Thr Leu Thr
 1               5                  10

<210> SEQ ID NO 127
<211> LENGTH: 13
<212> TYPE: PRT
<213> ORGANISM: mus musculus

<400> SEQUENCE: 127

Tyr Asp Tyr Trp Gly Gln Gly Thr Thr Leu Thr Val Ser
 1               5                  10

<210> SEQ ID NO 128
<211> LENGTH: 13
<212> TYPE: PRT
<213> ORGANISM: mus musculus

<400> SEQUENCE: 128

Asp Ile Leu Leu Thr Gln Ser Pro Ala Ile Leu Ser Val
 1               5                  10

<210> SEQ ID NO 129
<211> LENGTH: 13
<212> TYPE: PRT
<213> ORGANISM: mus musculus

<400> SEQUENCE: 129

Ile Leu Leu Thr Gln Ser Pro Ala Ile Leu Ser Val Ser
 1               5                  10

<210> SEQ ID NO 130
<211> LENGTH: 13
<212> TYPE: PRT
<213> ORGANISM: mus musculus

<400> SEQUENCE: 130

Pro Ala Ile Leu Ser Val Ser Pro Gly Glu Arg Val Ser
 1               5                  10

<210> SEQ ID NO 131
<211> LENGTH: 13
<212> TYPE: PRT
<213> ORGANISM: mus musculus

<400> SEQUENCE: 131

Ala Ile Leu Ser Val Ser Pro Gly Glu Arg Val Ser Phe
 1               5                  10

<210> SEQ ID NO 132
<211> LENGTH: 13
<212> TYPE: PRT
<213> ORGANISM: mus musculus

<400> SEQUENCE: 132

Leu Ser Val Ser Pro Gly Glu Arg Val Ser Phe Ser Cys

<210> SEQ ID NO 133
<211> LENGTH: 13
<212> TYPE: PRT
<213> ORGANISM: mus musculus

<400> SEQUENCE: 133

Glu Arg Val Ser Phe Ser Cys Arg Ala Ser Gln Phe Val
1               5                   10

<210> SEQ ID NO 134
<211> LENGTH: 13
<212> TYPE: PRT
<213> ORGANISM: mus musculus

<400> SEQUENCE: 134

Val Ser Phe Ser Cys Arg Ala Ser Gln Phe Val Gly Ser
1               5                   10

<210> SEQ ID NO 135
<211> LENGTH: 13
<212> TYPE: PRT
<213> ORGANISM: mus musculus

<400> SEQUENCE: 135

Ser Gln Phe Val Gly Ser Ser Ile His Trp Tyr Gln Gln
1               5                   10

<210> SEQ ID NO 136
<211> LENGTH: 13
<212> TYPE: PRT
<213> ORGANISM: mus musculus

<400> SEQUENCE: 136

Gln Phe Val Gly Ser Ser Ile His Trp Tyr Gln Gln Arg
1               5                   10

<210> SEQ ID NO 137
<211> LENGTH: 13
<212> TYPE: PRT
<213> ORGANISM: mus musculus

<400> SEQUENCE: 137

Ser Ser Ile His Trp Tyr Gln Gln Arg Thr Asn Gly Ser
1               5                   10

<210> SEQ ID NO 138
<211> LENGTH: 13
<212> TYPE: PRT
<213> ORGANISM: mus musculus

<400> SEQUENCE: 138

Ile His Trp Tyr Gln Gln Arg Thr Asn Gly Ser Pro Arg
1               5                   10

<210> SEQ ID NO 139
<211> LENGTH: 13
<212> TYPE: PRT
<213> ORGANISM: mus musculus

<400> SEQUENCE: 139

His Trp Tyr Gln Gln Arg Thr Asn Gly Ser Pro Arg Leu
1               5                   10

```
<210> SEQ ID NO 140
<211> LENGTH: 13
<212> TYPE: PRT
<213> ORGANISM: mus musculus

<400> SEQUENCE: 140

Pro Arg Leu Leu Ile Lys Tyr Ala Ser Glu Ser Met Ser
1               5                   10

<210> SEQ ID NO 141
<211> LENGTH: 13
<212> TYPE: PRT
<213> ORGANISM: mus musculus

<400> SEQUENCE: 141

Arg Leu Leu Ile Lys Tyr Ala Ser Glu Ser Met Ser Gly
1               5                   10

<210> SEQ ID NO 142
<211> LENGTH: 13
<212> TYPE: PRT
<213> ORGANISM: mus musculus

<400> SEQUENCE: 142

Leu Leu Ile Lys Tyr Ala Ser Glu Ser Met Ser Gly Ile
1               5                   10

<210> SEQ ID NO 143
<211> LENGTH: 13
<212> TYPE: PRT
<213> ORGANISM: mus musculus

<400> SEQUENCE: 143

Ile Lys Tyr Ala Ser Glu Ser Met Ser Gly Ile Pro Ser
1               5                   10

<210> SEQ ID NO 144
<211> LENGTH: 13
<212> TYPE: PRT
<213> ORGANISM: mus musculus

<400> SEQUENCE: 144

Glu Ser Met Ser Gly Ile Pro Ser Arg Phe Ser Gly Ser
1               5                   10

<210> SEQ ID NO 145
<211> LENGTH: 13
<212> TYPE: PRT
<213> ORGANISM: mus musculus

<400> SEQUENCE: 145

Ser Gly Ile Pro Ser Arg Phe Ser Gly Ser Gly Ser Gly
1               5                   10

<210> SEQ ID NO 146
<211> LENGTH: 13
<212> TYPE: PRT
<213> ORGANISM: mus musculus

<400> SEQUENCE: 146

Ser Arg Phe Ser Gly Ser Gly Ser Gly Thr Asp Phe Thr
1               5                   10

<210> SEQ ID NO 147
```

```
<211> LENGTH: 13
<212> TYPE: PRT
<213> ORGANISM: mus musculus

<400> SEQUENCE: 147

Thr Asp Phe Thr Leu Ser Ile Asn Thr Val Glu Ser Glu
1               5                   10

<210> SEQ ID NO 148
<211> LENGTH: 13
<212> TYPE: PRT
<213> ORGANISM: mus musculus

<400> SEQUENCE: 148

Phe Thr Leu Ser Ile Asn Thr Val Glu Ser Glu Asp Ile
1               5                   10

<210> SEQ ID NO 149
<211> LENGTH: 13
<212> TYPE: PRT
<213> ORGANISM: mus musculus

<400> SEQUENCE: 149

Leu Ser Ile Asn Thr Val Glu Ser Glu Asp Ile Ala Asp
1               5                   10

<210> SEQ ID NO 150
<211> LENGTH: 13
<212> TYPE: PRT
<213> ORGANISM: mus musculus

<400> SEQUENCE: 150

Asn Thr Val Glu Ser Glu Asp Ile Ala Asp Tyr Tyr Cys
1               5                   10

<210> SEQ ID NO 151
<211> LENGTH: 13
<212> TYPE: PRT
<213> ORGANISM: mus musculus

<400> SEQUENCE: 151

Glu Asp Ile Ala Asp Tyr Tyr Cys Gln Gln Ser His Ser
1               5                   10

<210> SEQ ID NO 152
<211> LENGTH: 13
<212> TYPE: PRT
<213> ORGANISM: mus musculus

<400> SEQUENCE: 152

Ala Asp Tyr Tyr Cys Gln Gln Ser His Ser Trp Pro Phe
1               5                   10

<210> SEQ ID NO 153
<211> LENGTH: 13
<212> TYPE: PRT
<213> ORGANISM: mus musculus

<400> SEQUENCE: 153

Asp Tyr Tyr Cys Gln Gln Ser His Ser Trp Pro Phe Thr
1               5                   10

<210> SEQ ID NO 154
<211> LENGTH: 13
<212> TYPE: PRT
```

<213> ORGANISM: mus musculus

<400> SEQUENCE: 154

His Ser Trp Pro Phe Thr Phe Gly Ser Gly Thr Asn Leu
 1               5                   10

<210> SEQ ID NO 155
<211> LENGTH: 13
<212> TYPE: PRT
<213> ORGANISM: mus musculus

<400> SEQUENCE: 155

Trp Pro Phe Thr Phe Gly Ser Gly Thr Asn Leu Glu Val
 1               5                   10

<210> SEQ ID NO 156
<211> LENGTH: 362
<212> TYPE: DNA
<213> ORGANISM: Artificial Sequence
<220> FEATURE:
<223> OTHER INFORMATION: Modified antibody variable region

<400> SEQUENCE: 156

```
gaagtgaagc tggaggagtc tggaggcggc ttggtgcaac ctggaggctc catgaaactc      60
tcctgtgttg cctctggatt cattttcagt aaccactgga tgaactgggt ccgccagtct     120
ccagagaagg ggcttgagtg ggttgctgaa attagatcaa atcgattaa ttctgcaaca      180
cattatgcgg agtctgtgaa agggaggttc accatctcaa gagatgattc caaaagtgct     240
gtgtacctgc aaatgaccga cctgagaact gaagacactg gcgtttatta ctgttccagg     300
aattactacg gtagtaccta cgactactgg ggccaaggca ccactctcac agtgtcctca     360
gg                                                                    362
```

<210> SEQ ID NO 157
<211> LENGTH: 362
<212> TYPE: DNA
<213> ORGANISM: Artificial Sequence
<220> FEATURE:
<223> OTHER INFORMATION: Modified antibody variable region

<400> SEQUENCE: 157

```
cctgaggaca ctgtgagagt ggtgccttgg ccccagtagt cgtaggtact accgtagtaa      60
ttcctggaac agtaataaac gccagtgtct tcagttctca ggtcggtcat ttgcaggtac     120
acagcacttt tggaatcatc tcttgagatg gtgaacctcc ctttcacaga ctccgcataa     180
tgtgttgcag aattaatcga ttttgatcta atttcagcaa cccactcaag ccccttctct     240
ggagactggc ggacccagtt catccagtgg ttactgaaaa tgaatccaga ggcaacacag     300
gagagtttca tggagcctcc aggttgcacc aagccgcctc cagactcctc cagcttcact     360
tc                                                                    362
```

<210> SEQ ID NO 158
<211> LENGTH: 340
<212> TYPE: DNA
<213> ORGANISM: Artificial Sequence
<220> FEATURE:
<223> OTHER INFORMATION: Modified antibody variable region

<400> SEQUENCE: 158

```
gacatcttgc tgactcagtc tccagccatc ctgtctgtga gtccaggaga aagagtcagt      60
ttctcctgca gggccagtca gttcgttggc tcaagcatcc actggtatca gcaaagaaca     120
```

| aatggttctc caaggcttct cataaagtat gcttctgagt ctatgtctgg catcccttct | 180 |
| agatttagtg gcagtggatc agggacagat tttactctta gcatcaacac tgtggagtct | 240 |
| gaagatattg cagattatta ctgtcaacaa agtcatagct ggccattcac gttcggctcg | 300 |
| gggacaaatt tggaagtaaa acgtgagtag aatttaaact | 340 |

<210> SEQ ID NO 159
<211> LENGTH: 340
<212> TYPE: DNA
<213> ORGANISM: Artificial Sequence
<220> FEATURE:
<223> OTHER INFORMATION: Modified antibody variable region

<400> SEQUENCE: 159

| agtttaaatt ctactcacgt tttacttcca aatttgtccc cgagccgaac gtgaatggcc | 60 |
| agctatgact ttgttgacag taataatctg caatatcttc agactccaca gtgttgatgc | 120 |
| taagagtaaa atgtctccct gatccactgc cactaaatct agaagggatg ccagacatga | 180 |
| actcagaagc atactttatg agaagccttg gagaaccatt tgttctttgc tgataccagt | 240 |
| ggatgcttga gccaacgaac tgactggccc tgcaggagaa actgactctt tctcctggac | 300 |
| tcacagacag gatggctgga gactgagtca gcaagatgtc | 340 |

<210> SEQ ID NO 160
<211> LENGTH: 3354
<212> TYPE: DNA
<213> ORGANISM: Artificial Sequence
<220> FEATURE:
<223> OTHER INFORMATION: anti-TNF alpha chimeric antibody heavy chain

<400> SEQUENCE: 160

| gaattctaaa tacattttag aagtcgataa acttaagttt ggggaaacta gaactactca | 60 |
| agctaaaatt aaaaggttga actcaataag ttaaaagagg acctctccag tttcggctga | 120 |
| atcctcaact tattttagaa atgcaaatta cccaggtggt gttttgctca gcctggactt | 180 |
| tcggtttggt ggggctggac agagtgtttc aaaaccactt cttcaaacca cagctacaag | 240 |
| tttacctagt ggttttattt tcccttcccc aaatagcctt gccacatgac ctgcttcctg | 300 |
| ccagctgctg caggtgttcc ggttctgatc ggcatcttg actcaactca acattgctca | 360 |
| attcatttaa aaatatttta aacttaattt attattgtta aaagtcagtt ctgaataggg | 420 |
| tatgagagag cctcactccc attcctcggt taaactttaa gtaatgtcag ttctacacaa | 480 |
| acaagacctc aaattgattg mcaaaaattt tggacattta aaaaaatgag kacttgaaaa | 540 |
| ccctctcaca ttttaaagtc mcagtattta actattttc ctaggaacca acttaagagt | 600 |
| aaagcaacat cttctaatat tccatacaca tacttctgtg ttcctttgaa agctggactt | 660 |
| ttgcaggctc caccagacct ctctagggaa ttctcatgtt tgacagctta tcatcgataa | 720 |
| gcttatgaat atgcaaatcc tctgaatcta catggtaaat ataggtttgt ctataccaca | 780 |
| aacagaaaaa catgagatca cagttctctc tacagttact gagcacacag gacctcacca | 840 |
| tgggatggag ctgtatcatc ctcttcttgg tagcaacagc tacaggtaag gggctcacag | 900 |
| tagcaggctt gaggtctgga catatatatg ggtgacaatg acatccactt tgcctttctc | 960 |
| tccacaggtg tccactccga agtgaagctg gaggagtctg gaggcggctt ggtgcaacct | 1020 |
| ggaggctcca tgaaactctc ctgtgttgcc tctggattca ttttcagtaa ccactggatg | 1080 |
| aactgggtcc gccagtctcc agagaagggg cttgagtggg ttgctgaaat tagatcaaaa | 1140 |

```
tcgattaatt ctgcaacaca ttatgcggag tctgtgaaag ggaggttcac catctcaaga   1200
gatgattcca aaagtgctgt gtacctgcaa atgaccgacc tgagaactga agacactggc   1260
gtttattact gttccaggaa ttactacggt agtacctacg actactgggg ccaaggcacc   1320
actctcacag tgtcctcagg tgagtcctta caacctctct cttctattca gcttaaatag   1380
attttactgc atttgttggg ggggaaatgt gtgtatctga atttcaggtc atgaaggact   1440
agggacacct tgggagtcag aaagggtcat tgggagcccg ggctgatgca gacagacatc   1500
ctcagctccc agacttcatg gccagagatt tataggatcc caagctagct ttctggggca   1560
ggccaggcct gaccttggct ttggggcagg aggggggcta aggtgaggca ggtggcgcca   1620
gccaggtgca cacccaatgc ccatgagccc agacactgga cgctgaacct cgcggacagt   1680
taagaaccca ggggcctctg cgccctgggc ccagctctgt cccacaccgc ggtcacatgg   1740
caccacctct cttgcagcct ccaccaaggg cccatcggtc ttccccctgg caccctcctc   1800
caagagcacc tctgggggca cagcggcccc gggctgcctg gtcaaggact acttccccga   1860
accggtgacg gtgtcgtgga actcaggcgc cctgaccagc ggcgtgcaca ccttccggc    1920 tgtcctacag tcctcaggac tctactccct cagcagcgtg gtgaccgtgc cctccagcag   1980
cttgggcacc cagacctaca tctgcaacgt gaatcacaag cccagcaaca ccaaggtgga   2040
caagaaagtt ggtgagaggc cagcacaggg agggaggggt tctgctggaa gccaggctca   2100
gcgctcctgc ctggacgcat cccggctatg cagccccagt ccagggcagc aaggcaggcc   2160
ccgtctgcct cttcacccgg aggcctctgc ccgccccact catgctcagg gagagggtct   2220
tctggctttt tccccaggct ctgggcaggc acaggctagg tgcccctaac ccaggccctg   2280
cacacaaagg ggcaggtgct gggctcagac ctgccaagag ccatatccgg gaggaccctg   2340
cccctgacct aagcccaccc caaaggccaa actctccact ccctcagctc ggacaccttc   2400
tctcctccca gattccagta actcccaatc ttctctctgc agagcccaaa tcttgtgaca   2460
aaactcacac atgcccaccg tgcccaggta agccagccca ggcctcgcct ccagctcaag   2520
gcgggacagg tgccctagag tagcctgcat ccagggacag gccccagccg ggtgctgaca   2580
cgtccacctc catctcttcc tcagcacctg aactcctggg gggaccgtca gtcttcctct   2640
tcccccaaaa acccaaggac accctcatga tctcccggac ccctgaggtc acatgcgtgg   2700
tggtggacgt gagccacgaa gaccctgagg tcaagttcaa ctggtacgtg gacggcgtgg   2760
aggtgcataa tgccaagaca aagccgcggg aggagcagta caacagcacg taccgtgtgg   2820
tcagcgtcct caccgtcctg caccaggact ggctgaatgg caaggagtac aagtgcaagg   2880
tctccaacaa agccctccca gcccccatcg agaaaaccat ctccaaagcc aaagtggga   2940 cccgtggggt gcgagggcca catggacaga ggccggctcg gcccaccctc tgccctgaga   3000
gtgaccgctg taccaacctc tgtccctaca gggcagcccc gagaaccaca ggtgtacacc   3060 ctgccccat cccgggatga gctgaccaag aaccaggtca gcctgacctg cctggtcaaa   3120
ggcttctatc ccagcgacat cgccgtggag tgggagagca atgggcagcc ggagaacaac   3180
tacaagacca cgcctcccgt gctggactcc gacggctcct tcttcctcta cagcaagctc   3240
accgtggaca agagcaggtg gcagcagggg aacgtcttct catgctccgt gatgcatgag   3300
gctctgcaca accactacac gcagaagagc ctctccctgt ctccgggtaa atga         3354
```

<210> SEQ ID NO 161
<211> LENGTH: 450
<212> TYPE: PRT
<213> ORGANISM: Artificial Sequence
<220> FEATURE:
<223> OTHER INFORMATION: anti-TNF alpha chimeric antibody heavy chain

<400> SEQUENCE: 161

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 162
<211> LENGTH: 3775
<212> TYPE: DNA
<213> ORGANISM: Artificial Sequence
<220> FEATURE:
<223> OTHER INFORMATION: anti-TNF alpha chimeric antibody light chain

<400> SEQUENCE: 162
gaattctaaa tacattttag aagtcgataa acttaagttt ggggaaacta gaactactca      60
agctaaaatt aaaaggttga actcaataag ttaaaagagg acctctccag tttcggctga     120
atcctcaact tattttagaa atgcaaatta cccaggtggt gttttgctca gcctggactt     180
tcggtttggt ggggctggac agagtgtttc aaaaccactt cttcaaacca cagctacaag     240
tttacctagt ggttttattt tcccttcccc aaatagcctt gccacatgac ctgcttcctg     300
ccagctgctg caggtgttcc ggttctgatc ggccatcttg actcaactca acattgctca     360
attcatttaa aaatatttta aacttaattt attattgtta aaagtcagtt ctgaataggg     420
tatgagagag cctcactccc attcctcggt taaactttaa gtaatgtcag ttctacacaa     480
acaagacctc aaattgattg acaaaaattt tggacatttt aaaaaatgag tacttgaaaa     540
ccctctcaca ttttaaagtc acagtattta actattttc ctaggaacca acttaagagt     600
aaaagcaaca tcttctaata ttccatacac atacttctgt gttcctttga aagctggact     660
tttgcaggct ccaccagacc tctctagagt cgacctgcag cccaagctta tgaatatgca     720
aatcctctga atctacatgg taaatatagg tttgtctata ccacaaacag aaaaacatga     780
gatcacagtt ctctctacag ttactgagca cacaggacct caccatggga tggagctgta     840
tcatcctctt cttggtagca acagctacag gtaaggggct cacagtagca ggcttgaggt     900
ctggacatat atatgggtga caatgacatc cactttgcct ttctctccac aggtgtccac     960
tccgacatct gctgactca gtctccagcc atcctgtctg tgagtccagg agaaagagtc    1020
agtttctcct gcagggccag tcagttcgtt ggctcaagca tccactggta tcagcaaaga    1080
acaaatggtt ctccaaggct tctcataaag tatgcttctg agtctatgtc tggcatccct    1140
tctagattta gtggcagtgg atcagggaca gattttactc ttagcatcaa cactgtggag    1200
tctgaagata ttgcagatta ttactgtcaa caaagtcata ctggccatt cacgttcggc    1260 tcggggacaa atttggaagt aaaacgtgag tagaatttaa actttgcttc ctcagttgga    1320
tcctggcaga gtctcacaga tgcttctgag acaacatttg ctttcaaaaa atgaaccaca    1380
cacatcctaa agatctcagc cacttcccat gtttcatttt atgttacagc aaacatcaca    1440
acaatcattc ctacagatca ccactgcatg tgatcaataa aatagttttt gcaacaatgg    1500
tacttatgat aatcatcttt tattgtttac aaatactgct ttacaatagt tattcggttg    1560
cactgttcat attagatttc caattagctc acttaggaac ataagtccct cgaacagctc    1620
agtcatcttt tcattcctg tttctatccc ctacatctct ttcctttgca gacgactatc    1680

```
tcctacactg aaacaggaaa gctagctttt tttttcagt gctatttaat tatttcaata    1740
tcctctcatc aaatgtattt aaataacaaa agctcaacca aaaagaaaga aatatgtaat    1800
tctttcagag taaaaatcac acccatgacc tggccactga gggcttgatc aattcacttt    1860
gaatttggca ttaaatacca ttaaggtata ttaactgatt ttaaaataag atatattcgt    1920
gaccatgttt ttaactttca aaaatgtagc tgccagtgtg tgattttatt tcagttgtac    1980
aaaatatcta aacctatagc aatgtgatta ataaaaactt aaacatattt tccagtacct    2040
taattctgtg ataggaaaat tttaatctga gtattttaat ttcataatct ctaaaatagt    2100
ttaatgattt gtcattgtgt tgctgtcgtt tacccagct gatctcaaaa gtgatatttta   2160 aggagattat tttggtctgc aacaacttga taggactatt ttagggcctt tttaaagctc    2220
tattaaaact aacttacaac gattcaaaac tgttttaaac tatttcaaaa tgattttaga    2280
gccttttgaa aactctttta aacactttt aaactctatt aaaactaata agataacttg     2340
aaataatttt catgtcaaat acattaactg tttaatgttt aaatgccaga tgaaaaatgt    2400
aaagctatca agaattcacc cagataggag tatcttcata gcatgttttt ccctgcttat    2460
tttccagtga tcacattatt ttgctaccat ggttatttta tacaattatc tgaaaaaaat    2520
tagttatgaa gattaaaaga aagaaaata ttaaacataa gagattcagt ctttcatgtt     2580
gaactgcttg gttaacagtg aagttagttt taaaaaaaaa aaaaactatt tctgttatca    2640
gctgacttct ccctatctgt tgacttctcc cagcaaaaga ttcttatttt acattttaac    2700
tactgctctc ccacccaacg ggtggaatcc cccagagggg gatttccaag aggccacctg    2760
gcagttgctg agggtcagaa gtgaagctag ccacttcctc ttaggcaggt ggccaagatt    2820
acagttgacc tctcctggta tggctgaaaa ttgctgcata tggttacagg ccttgaggcc    2880
tttgggaggg cttagagagt tgctggaaca gtcagaaggt ggaggggctg acaccaccca    2940
ggcgcagagg cagggctcag ggcctgctct gcagggaggt tttagcccag cccagccaaa    3000 gtaaccccg ggagcctgtt atcccagcac agtcctggaa gaggcacagg ggaaataaaa     3060
gcggacggag gctttccttg actcagccgc tgcctggtct tcttcagacc tgttctgaat    3120
tctaaactct gaggggggtcg gatgacgtgg ccattctttg cctaaagcat tgagtttact   3180
gcaaggtcag aaaagcatgc aaagccctca gaatggctgc aaagagctcc aacaaaacaa    3240
tttagaactt tattaaggaa taggggggaag ctaggaagaa actcaaaaca tcaagatttt   3300
aaatacgctt cttggtctcc ttgctataat tatctgggat aagcatgctg ttttctgtct    3360
gtccctaaca tgccctgtga ttatccgcaa acaacacacc caagggcaga actttgttac    3420
ttaaacacca tcctgtttgc ttctttcctc aggaactgtg gctgcaccat ctgtcttcat    3480
cttcccgcca tctgatgagc agttgaaatc tggaactgcc tctgttgtgt gcctgctgaa    3540
taacttctat cccagagagg ccaaagtaca gtggaaggtg gataacgccc tccaatcggg    3600
taactcccag gagagtgtca cagagcagga cagcaaggac agcacctaca gcctcagcag    3660
caccctgacg ctgagcaaag cagactacga gaacacaaaa gtctacgcct gcgaagtcac    3720
ccatcagggc ctgagctcgc ccgtcacaaa gagcttcaac aggggagagt gttag         3775
```

<210> SEQ ID NO 163  
<211> LENGTH: 214  
<212> TYPE: PRT  
<213> ORGANISM: Artificial Sequence  
<220> FEATURE:  
<223> OTHER INFORMATION: anti-TNF alpha chimeric antibody light chain

<400> SEQUENCE: 163

```
Asp Ile Leu Leu Thr Gln Ser Pro Ala Ile Leu Ser Val Ser Pro Gly
 1               5                  10                  15

Glu Arg Val Ser Phe Ser Cys Arg Ala Ser Gln Phe Val Gly Ser Ser
             20                  25                  30

Ile His Trp Tyr Gln Gln Arg Thr Asn Gly Ser Pro Arg Leu Leu Ile
         35                  40                  45

Lys Tyr Ala Ser Glu Ser Met Ser Gly Ile Pro Ser Arg Phe Ser Gly
 50                  55                  60

Ser Gly Ser Gly Thr Asp Phe Thr Leu Ser Ile Asn Thr Val Glu Ser
65                   70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 164
<211> LENGTH: 330
<212> TYPE: PRT
<213> ORGANISM: Artificial Sequence
<220> FEATURE:
<223> OTHER INFORMATION: anti-TNF alpha chimeric antibody heavy chain
      constant region

<400> SEQUENCE: 164

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                   70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
```

```
                130               135               140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 165
<211> LENGTH: 106
<212> TYPE: PRT
<213> ORGANISM: Artificial Sequence
<220> FEATURE:
<223> OTHER INFORMATION: anti-TNF alpha chimeric antibody light chain
      constant region

<400> SEQUENCE: 165

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
                35                  40                  45

Gly Asn Ser Gln Glu Ser Val Thr Glu Gln Asp Ser Lys Asp Ser Thr
50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105
```

TNF ALPHA-BINDING POLYPEPTIDE COMPOSITIONS AND METHODS

CROSS-REFERENCE TO RELATED APPLICATIONS

This application is a continuation-in-part of U.S. patent application Ser. No. 10/495,146, filed on May 10, 2004, which is the National Stage of International Application Serial No. PCT/EP2002/012566, filed on Nov. 11, 2002, which is incorporated herein by reference.

FIELD OF THE INVENTION

The present invention relates to polypeptide compositions. More particularly the invention relates to polypeptide compositions that bind to human tumor necrosis factor alpha (TNF alpha), such as antibodies, antibody fragments, and the like, and to methods of manufacturing the polypeptide compositions. The invention also relates to methods of utilizing the polypeptide compositions in therapeutic and diagnostic settings.

BACKGROUND OF THE INVENTION

There are many instances in which the efficacy of a therapeutic protein is limited by an unwanted immune reaction to the therapeutic protein. Several mouse monoclonal antibodies have shown promise as therapeutic agents in a number of human disease settings, but in certain cases have failed due to the induction of significant degrees of a human anti-murine antibody (HAMA) response (see e.g., Schroff, R. W. et al., (1985) *Cancer Res.* 45: 879-885; Shawler, D. L. et al., (1985) *J. Immunol.* 135: 1530-1535). For monoclonal antibodies, a number of techniques have been developed in attempt to reduce the HAMA response (see, e.g., WOA8909622; EPA0239400; EPA0438310; WOA9106667; EPA0699755). These recombinant DNA approaches have generally reduced the mouse genetic information in the final antibody construct while increasing the human genetic information in the final construct. These changes notwithstanding, the resultant "humanized" antibodies have, in several cases, still reportedly elicited an immune response in patients (see e.g., Issacs J. D., (1990) *Sem. Immunol.* 2: 449, 456; Rebello, P. R. et al., (1999) *Transplantation* 68: 1417-1420).

Non-human antibodies are not the only class of polypeptide molecule administered as a therapeutic agent against which an immune response may be mounted. Even proteins of human origin and with the same amino acid residue sequences as occur within humans can still induce an immune response in humans. Notable examples include therapeutic use of granulocyte-macrophage colony stimulating factor (Wadhwa, M. et al., (1999) *Clin. Cancer Res.* 5: 1353-1361) and interferon alpha 2 (Russo, D. et al., (1996) *Bri. J. Haem.* 94: 300-305; Stein, R., et al. (1988) *New Engl. J. Med.* 318: 1409-1413) among others.

Key to the induction of a human immune response is the presence within the protein of peptide segments that can stimulate the activity of T cells via presentation on MHC Class II molecules (so-called "T cell epitopes"). Such T cell epitopes are commonly defined as any amino acid residue sequence with the ability to bind to MHC Class II molecules. Implicitly, a "T cell epitope" means an epitope that, when bound to MHC molecules can be recognized by a T cell receptor (TCR), and which can cause the activation of these T cells by engaging a TCR to promote a T cell response.

MHC Class II molecules are a group of highly polymorphic proteins that play a central role in helper T cell selection and activation. The human leukocyte antigen group DR (HLA-DR) is the predominant isotype of this group of proteins; however, isotypes HLA-DQ and HLA-DP perform similar functions. The present invention is applicable to the detection of T cell epitopes presented within the context of DR, DP or DQ MHC Class II molecules. In the human population, individuals bear two to four DR alleles, two DQ and two DP alleles. The structures of a number of DR molecules have been solved. These molecules have open-ended peptide binding grooves with a number of hydrophobic pockets that can engage hydrophobic residues (pocket residues) of the peptide (see e.g., Brown et al., *Nature* (1993) 364: 33; Stern et al., (1994) *Nature* 368: 215). Polymorphism within the different allotypes of Class II molecules contributes to a wide diversity of different binding surfaces for peptides within the peptide binding groove and, at the population level, ensures maximal flexibility with regard to the ability to recognize foreign proteins and mount an immune response to pathogenic organisms.

An immune response to a therapeutic protein proceeds via the MHC Class II peptide presentation pathway. Exogenous proteins are engulfed and processed for presentation in association with MHC Class II molecules of the DR, DQ or DP type. MHC Class II molecules are expressed by dedicated antigen presenting cells (APCs), such as macrophages and dendritic cells. Engagement of a MHC Class II peptide complex by a cognate T cell receptor on the surface of the T cell, together with the cross-binding of certain other co-receptors such as the CD4 molecule, can activate the T cell. Activation leads to the release of cytokines, which further activate other lymphocytes, such as B cells (to produce antibodies) and T killer cells, as a full cellular immune response.

T cell epitope identification is an important prerequisite for eliminating epitopes and reducing antigenicity; however, there are few clear cases in the art where epitope identification and epitope removal are integrated into a single scheme. International Application Publications No. WO98/52976 and No. WO00/34317 each disclose computational threading approaches to identifying polypeptide sequences with the potential to bind a sub-set of human MHC Class II DR allotypes. The predicted T cell epitopes reportedly are eliminated by incorporation of amino acid substitutions within the protein of interest. However, with this scheme and other computationally based procedures for epitope identification (see e.g., Godkin, A. J. et al., (1998) *J. Immunol.* 161: 850-858; Sturniolo, T. et al., (1999) *Nat. Biotechnol.* 17: 555-561), peptides that are predicted to be capable of binding MHC Class II molecules may not function as T cell epitopes in all situations, (particularly in vivo) due to processing pathways or other phenomena. In addition, computational approaches to T cell epitope prediction generally have not been capable of predicting epitopes with DP or DQ restriction.

In addition to computational techniques, in vitro methods have been reported for measuring the ability of synthetic peptides to bind MHC Class II molecules. An exemplary method uses B-cell lines of defined MHC allotype as a source of MHC Class II binding surface and may be used for MHC Class II ligand identification (see e.g., Marshall K. W. et al., (1994) *J. Immunol.* 152:4946-4956; O'Sullivan et al., (1990) *J. Immunol.* 145: 1799-1808; Robadey C. et al., (1997) *J. Immunol* 159: 3238-3246). However, such techniques are not adapted for screening multiple potential epitopes to a wide diversity of MHC allotypes, nor can the technique confirm the ability of a binding peptide to function as a T cell epitope.

Recently, techniques exploiting soluble complexes of recombinant MHC molecules in combination with synthetic peptides have come into use (see e.g., Kern, F. et al., (1998) *Nature Medicine* 4:975-978; Kwok, W. W. et al., (2001) *TRENDS in Immunol.* 22:583-588). These procedures are used to identify the presence of T cell clones in peripheral blood samples from human or experimental animal subjects, which are able to bind particular MHC-peptide complexes, but are not adapted for the screening multiple potential epitopes to a wide diversity of MHC allotypes.

Biological assays of T cell activation can provide a practical alternative for assessing the ability of a peptide/protein sequence to evoke an immune response. Examples of this kind of approach include the work of Petra et al., using T cell proliferation assays to the bacterial protein staphylokinase, followed by epitope mapping using synthetic peptides to stimulate T cell lines (Petra, A. M. et al., (2002) *J. Immunol.* 168: 155-161). Similarly, T cell proliferation assays using synthetic peptides of the tetanus toxin protein reportedly have been used to identify immunodominant epitope regions of the tetanus toxin (Reece J. C. et al., (1993) *J. Immunol.* 151: 6175-6184). WO99/53038 discloses an approach in which T cell epitopes in a test protein may be determined using isolated sub-sets of human immune cells, promoting their in vitro differentiation, culture of the cells in the presence of synthetic peptides of interest, and measurement of any induced proliferation in the cultured T cells. The same technique is also described by Stickler et al., (2000) *J. Immunotherapy* 23:654-660 where, in both instances, the method is applied to the detection of T cell epitopes within bacterial subtilisin. Such a technique requires careful application of cell isolation techniques, and culturing the cells with multiple cytokine supplements to obtain the desired immune cell sub-sets (dendritic cells, CD4$^+$ and or CD8$^+$ T cells) and are not conducive to rapid through-put screening using multiple donor samples.

Chimeric versions of the murine antibody commonly known as A2 are described in U.S. Pat. No. 6,284,471, U.S. Pat. No. 5,919,425, and U.S. Pat. No. 5,656,272, the relevant disclosures of which are incorporated herein by reference. The clinical use of a chimeric A2 (cA2) treating TNF alpha mediated disease is described by Le et al., (U.S. Pat. No. 5,919,425). Similarly, Feldmen et al., (U.S. Pat. No. 6,270,766) describe use of the same antibody in combination therapy with a myeloablative agent methotrexate for the treatment of arthritis and Crohn's disease. Large clinical trials have now been conducted using this antibody, which has received the compound name "infliximab" (available from Schering-Plough, Ltd., UK), and is marketed in some countries as REMICADE® antibody. This antibody has demonstrated therapeutic efficacy in the treatment of rheumatoid arthritis and Crohn's disease, and has received regulatory approval for its use in treating Crohn's disease in the USA and in Europe. The antibody is produced by recombinant techniques and, as noted above, the antibody is "chimeric", meaning that the constant region of the antibody is comprised of sequence derived from human constant region genes and the contribution of mouse derived protein sequence is therefore reduced. Despite its chimeric nature, up to 13% of patients treated for Crohn's disease with cA2 exhibited an immune response to the therapeutic antibody (see e.g., Mani R. N. et al., (1998) *Arthritis Rheum.* 41:1552-1563; Elliot M. J. et al., (1994) *Lancet* 344: 1105-1110; Targan S. R. et al., (1997) *N. Engl. J Med.* 337: 1029-1035; Present D. H. et al., (1999) *N. Engl. J Med.* 340: 1398-1405).

A variety of antibodies having specificity toward TNF alpha, as that is similar to the specificity of A2, are known in the art. Examples include the anti-TNF alpha preparations disclosed in EP0212489, EP0218868, EP0288088 and WO91/02078. Further examples of rodent or murine monoclonal antibodies specific for recombinant human TNF alpha have been described in the literature (see e.g., Liang, et al., (1986) *Biochem. Biophys. Res. Comm.* 137: 847-854; Meager, et al., (1987), *Hybridoma* 6: 305-311; Fendlym et al., (1987), *Hybridoma* 6: 359-369; Bringman, et al., (1987), *Hybridoma* 6: 489-507; Hirai, et al., (1987) *J. Immunol. Meth.* 96: 57-62 and Moller, et al., (1990), *Cytokine* 2: 162-169). Some of these antibodies are able to neutralize the effect of TNF alpha in vitro and have been used to develop immunoassays for TNF alpha or are used in the purification of recombinant TNF alpha. In general, and in contrast with chimeric versions of A2, such as infliximab, these other antibodies have not been developed for in vivo diagnostic or therapeutic uses in humans.

Clinical studies have been conducted using a murine anti-TNF alpha monoclonal antibody in human subjects. In fourteen patients with severe septic shock who received a single dose of a murine anti-TNF alpha monoclonal antibody, seven reportedly developed a human anti-murine antibody response to the treatment, due to the immunogenicity of the therapeutic murine antibody. (Exley, A. R. et al., (1990), *Lancet* 335: 1275-1277). Such immunogenicity can render treatment ineffective in patients undergoing diagnostic or therapeutic administration of murine anti-TNF alpha monoclonal antibodies.

In this regard, Adair et al. (EP0927758) described recombinant antibody molecules, including antibodies with human constant region sequences and versions in which the complementarity determining regions (CDRs) have been engrafted onto modified human antibody framework sequences. Such antibodies and humanized antibodies are claimed to retain specificity to human TNF alpha and to be useful in diagnosis and therapy.

There is an ongoing need for techniques to identify and to eliminate, or at least to reduce, the antigenicity of T cell epitopes present in a given therapeutically valuable polypeptide composition. One such therapeutically valuable polypeptide composition is a monoclonal antibody having binding specificity for tumor necrosis factor alpha (TNF alpha), preferably a chimeric form of the antibody A2 as described in U.S. Pat. No. 6,284,471.

Accordingly, there is an ongoing need for improved anti-TNF alpha antibodies or related polypeptide compositions that exhibit low levels of immunogenicity toward human patients in comparison to chimeric A2 antibody and to murine anti-TNF alpha monoclonal antibodies. Such improved polypeptide compositions would display an increased circulation time within the patient and would be of particular benefit in chronic or recurring disease settings associated with TNF alpha expression. The present invention provides TNF alpha binding polypeptide compositions having reduced immunogenicity in vivo relative to currently available anti-TNF alpha antibodies such as infliximab.

SUMMARY OF THE INVENTION

The present invention provides TNF alpha-binding polypeptide compositions, which include modified forms of anti-TNF alpha monoclonal antibody heavy chain and/or light chain variable region (V-region) polypeptides, such as modified forms of the A2 heavy chain and light chain variable regions. Such modified heavy chain and light chain variable region polypeptides ("modified variable regions") have binding specificity for human TNF alpha, but are less immunogenic, when administered to a human patient, than the native non-human anti-TNF alpha monoclonal antibody variable regions. The modified variable regions include at least one fewer T cell epitope than the corresponding native non-human monoclonal variable regions.

TNF alpha is involved in the mediation of a number of pathological conditions including Crohn's disease, rheumatoid arthritis and endotoxic or cardiovascular shock. Thus, the TNF alpha-binding polypeptide compositions of the present invention have therapeutic utility against these pathological conditions as well as other diseases in which TNF alpha is a significant component of the pathophysiology.

A TNF alpha-binding polypeptide composition of the invention comprises at least one polypeptide selected from the group consisting of a modified heavy chain variable region polypeptide and a modified light chain variable region polypeptide. The modified heavy chain variable region polypeptide and the modified light chain variable region polypeptide each are homologous to respective heavy chain and light chain variable regions of a non-human monoclonal antibody that specifically binds to human TNF alpha. The amino acid residue sequences of the modified heavy chain variable region polypeptide and the modified light chain variable region polypeptide differ from the amino acid residue sequences of their respective non-human monoclonal antibody heavy chain variable region and light chain variable region by at least one amino acid residue substitution, deletion, or addition. The TNF alpha-binding polypeptide compositions of the present invention are less immunogenic to a human than an antibody comprising the native heavy chain and light chain variable regions of the non-human monoclonal antibody.

The TNF alpha-binding polypeptide compositions of the present invention can be, for example, chimeric antibodies, antibody fragments such as Fv and Fab' fragments, antibody fusion proteins in which an immune effector protein, such as a cytokine, is bound to the C-terminus of the antibody heavy chain, as well as fusion proteins of modified antibody variable region proteins, or fragments thereof, with an immune effector protein.

In one embodiment, the present invention provides a chimeric anti-TNF alpha antibody comprising human heavy chain constant regions, human light chain constant regions and variable regions selected from a modified heavy chain variable region, a modified light chain variable region, and a combination thereof. All of the constant and variable regions are operably connected to one another in the form of a functional antibody that is capable of specifically binding to human TNF alpha. The modified heavy chain variable regions and the modified light chain variable regions each are homologous to respective heavy chain and light chain variable regions of a non-human monoclonal antibody that specifically binds to human TNF alpha. The amino acid residue sequence of the modified heavy chain variable region and the modified light chain variable region differ from the amino acid residue sequences of their respective non-human monoclonal antibody heavy chain variable region and light chain variable region counterparts by at least one amino acid residue substitution, deletion or addition in a region of their amino acid residue sequence that is an epitope in the counterpart non-human monoclonal antibody. Preferably the non-human monoclonal antibody is a murine antibody.

The chimeric anti-TNF alpha antibodies of the present invention are less immunogenic to a human than an antibody comprising the same human constant regions and having heavy chain and light chain variable regions identical to the respective heavy chain and light chain variable regions of the counterpart non-human monoclonal antibody.

In a preferred embodiment, the present invention provides a chimeric anti-TNF alpha antibody having reduced immunogenicity relative to chimeric A2 antibodies, such as infliximab, by virtue of having one or more fewer T cell epitopes in its variable regions than are present in the variable regions of A2.

Preferably, the chimeric antibody of the present invention comprises human constant regions and a combination of heavy and light chain V-regions selected from the combinations VH1/VL1, VH1/VL5, VH1/VL8, VH5/VL12, VH8/VL5, as described hereinbelow. More preferably the chimeric antibody includes the heavy chain variable region designated herein as VH5 and the light chain variable region designated herein as VL12.

The chimeric anti-TNF alpha antibodies of the present invention preferably include a human IgG heavy chain constant domain and a human kappa light chain constant domain. More preferably, the IgG heavy chain constant domain comprises an IgG1 domain.

BRIEF DESCRIPTION OF THE DRAWINGS

FIGS. 1A-1J collectively illustrate the relationship of synthetic oligonucleotides used in the construction of a wild-type chimeric A2 (WT cA2) heavy chain variable region (VH) gene and the WT cA2 light chain variable region gene (VL). In particular, FIG. 1A shows the sequences of forward strand oligonucleotides utilized in the construction of the WT cA2 VH gene (solid arrow indicates 5'-3' orientation). FIG. 1B shows the sequences of reverse strand oligonucleotides utilized in the construction of the WT cA2 VH gene (broken arrow indicates 5'-3' orientation). FIG. 1C (top panel) shows the relationship between the forward (solid arrow) and reverse strand (broken arrow) oligonucleotides. The sequence of the double stranded DNA, formed by annealing and ligation of the oligonucleotides, is shown beneath the arrow (bottom panel). FIG. 1D shows the relationship between the double stranded DNA and the reading frame of the WT cA2 VH gene. FIG. 1E shows the protein sequence (SEQ ID NO: 9) encoded by the WT cA2 VH gene. FIG. 1F shows the sequences of forward strand oligonucleotides utilized in the construction of the WT cA2 VL gene (solid arrow indicates 5'-3' orientation). FIG. 1G shows the sequences of reverse strand oligonucleotides utilized in the construction of the WT cA2 VL gene (broken arrow indicates 5'-3' orientation). FIG. 1H (top panel) shows the relationship between the forward (solid arrow) and reverse strand (broken arrow) oligonucleotides. The sequence of the double stranded DNA, formed by annealing and ligation of the oligonucleotides, is shown beneath the arrow (bottom panel). FIG. 1I shows the relationship between the double stranded DNA and the reading frame of the gene for the WT cA2 VL gene. FIG. 1J shows the protein sequence (SEQ ID NO: 10) encoded by the WT cA2 VL gene.

FIG. 6 provides proliferative response recorded for each of the 13-mer peptides P1-P15 in an in vitro naive T cell proliferation assay. Panel A depicts responses in PBMC from donor (#2). Panel B depicts responses in PBMC from donor (#4). The results are shown for the peptides given at both 1 μM and 5 μM concentration. In both Panels, responses with an SI>2.0 are indicated as positive (+) and results with an SI<2.0 are indicated as negative (−).

FIG. 8 illustrates amino acid residue sequences of preferred polypeptides of the invention.

FIG. 11 illustrates a total of 40 synthetic peptides that were evaluated for antigenicity using T cell assays. The peptides span the entire VH region of the WT cA2 antibody of Example 3. The sequences and relative position of each peptide CA1-CA40 (15-mer segments of SEQ ID NO: 11) are shown in the figure (residue numbers of the segments relative to SEQ ID NO: 11 are shown in parentheses after each peptide sequence). Collectively the peptides provide a survey of the entire VH region and part of the human $C_H1$ domain of the WT cA2 of Example 3 (SEQ ID NO: 11). The boxes and arrows indicate the extent of the VH and $C_H1$ domain of the constant region within the sequence as spanned by the peptides.

FIG. 12 illustrates a total of 35 synthetic peptides that were evaluated for antigenicity using T cell assays. The peptides span the entire VL region of the WT cA2 antibody of Example 3. The sequences and relative position of each peptide CA41-CA75 (15-mer segments of SEQ ID NO: 12) are shown in the figure (residue numbers of the segments relative to SEQ ID NO: 12 are shown in parentheses after each peptide sequence). Collectively the peptides provide a survey of the entire VL region and part of the human $C_k$ domain of the WT cA2 antibody of Example 3 (SEQ ID NO: 12). The boxes and arrows indicate the extent of the VL and $C_k$ domains within the sequence spanned by the peptides.

FIG. 13 illustrates 13-mer segments of the heavy chain of the chimeric WT cA2 anti-TNF antibody of Example 3.

FIG. 14 illustrates 13-mer segments of the light chain of the chimeric WT cA2 anti-TNF antibody of Example 3.

FIG. 15 shows the DNA sequence (SEQ ID NO: 160) of the gene encoding the mature heavy chain of the WT cA2 antibody prepared in Example 3.

FIG. 16 shows the amino acid sequence (SEQ ID NO: 161) of the mature heavy chain of the WT cA2 antibody prepared in Example 3.

FIG. 17 shows the DNA sequence (SEQ ID NO: 162) of the gene encoding the mature light chain of the WT cA2 antibody prepared in Example 3.

FIG. 18 shows the amino acid sequence (SEQ ID NO: 163) of the mature light chain of the WT cA2 antibody prepared in Example 3.

FIG. 19 shows the amino acid residue sequence (SEQ ID NO: 164) of a preferred heavy chain constant region.

FIG. 20 shows the amino acid residue sequence (SEQ ID NO: 161) of the preferred light chain constant region.

DETAILED DESCRIPTION OF PREFERRED EMBODIMENTS

Figure 1A:
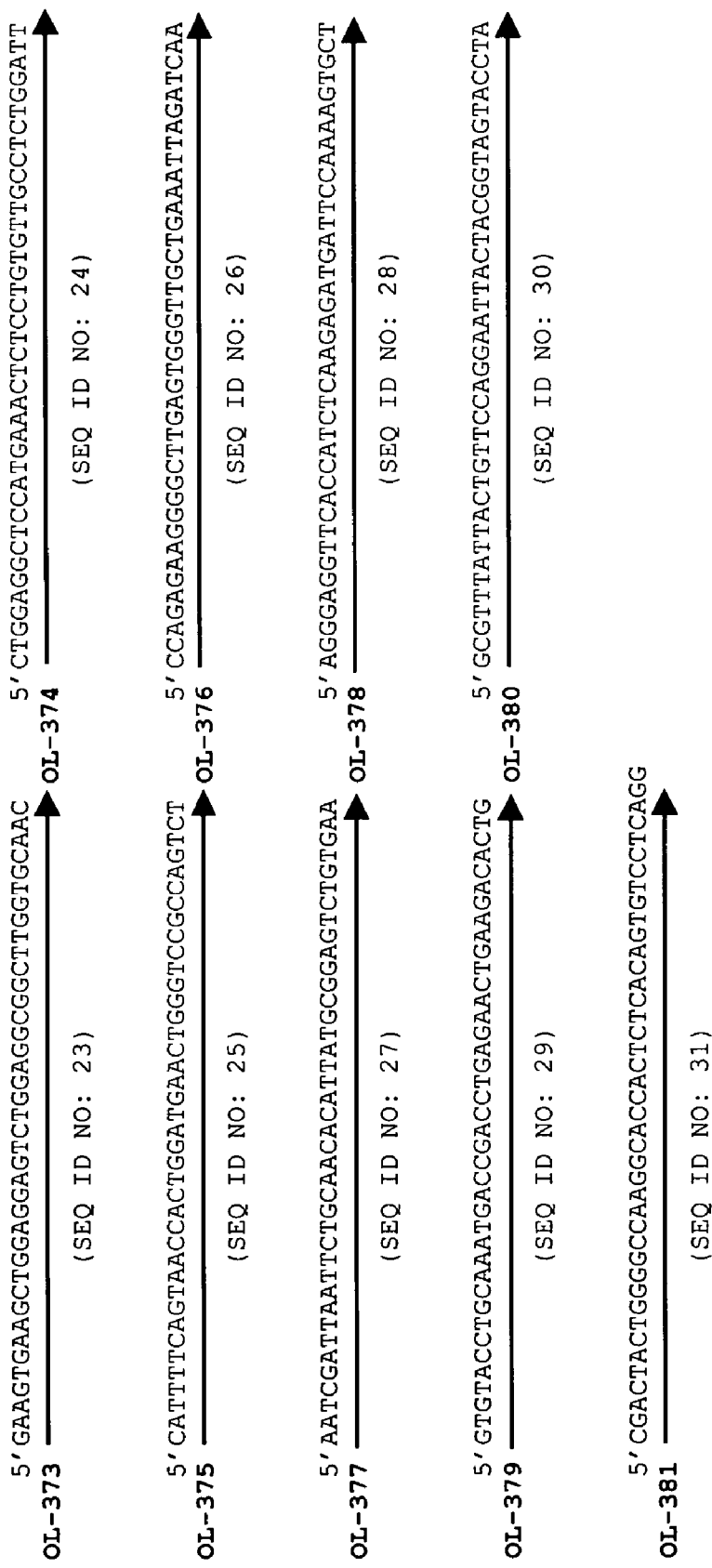
Figure 1C:
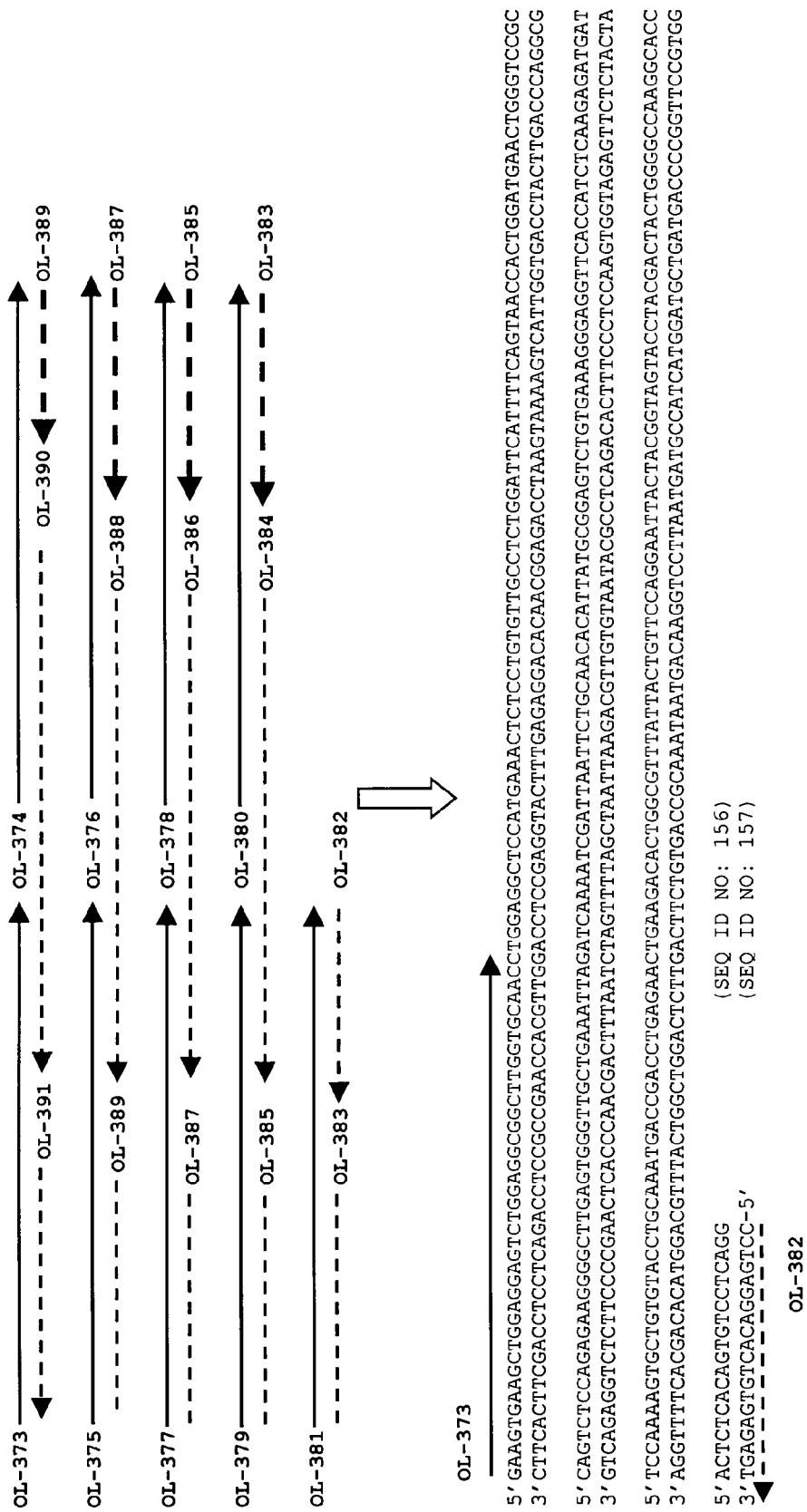

The terms "substantially non-immunogenic" and "reduced immunogenic potential" in reference to TNF alpha-binding polypeptide composition of the invention means that the polypeptide composition exhibits reduced immunogenicity compared to a counterpart non-human anti-TNF alpha monoclonal antibody.

The term "immunogenicity" refers to an ability of a polypeptide to provoke, induce or otherwise facilitate a humoral and or T cell-mediated response in a host animal, particularly in a human.

The term "antibody" refers to a protein of the immunoglobulin family that is capable of combining, interacting or otherwise associating with an antigen. The term "antigen" refers to a substance that is capable of interacting with an antibody and in the context of the present invention is tumor necrosis factor alpha (TNF alpha), preferably human TNF alpha or any TNF alpha representing an antigen for antibody A2. The TNF alpha may be soluble TNF alpha or membrane associated TNF alpha.

The term "immunoglobulin" is used herein to refer to a protein comprising of one or more polypeptides substantially encoded by immunoglobulin genes. The recognized immunoglobulin heavy chain constant region gene isotypes include IgG, (subtypes IgG1, IgG2, IgG3, and IgG4), IgM, IgA (subtypes IgA1 and IgA2), IgD, and IgE. Multiple immunoglobulin variable region genes are utilized in the production of natural antibodies. One natural form of immunoglobulin is a tetramer comprising two identical pairs in which each pair has one light chain and one heavy chain. In each pair the heavy and light chain variable regions together provide the binding surface capable of interacting with the antigen. The term VH is used herein to refer to the heavy chain variable region, and the term VL is used herein to refer to the light chain variable region.

In the TNF alpha-binding polypeptide compositions of the present invention, a VH region polypeptide is a polypeptide of about 110 to 125 amino acid residues in length, which is capable of binding to human TNF alpha preferably in combination with a VL region polypeptide. Similarly, a VL region is a polypeptide that is about 95-130 amino acid residues in length. Full-length immunoglobulin heavy chains are about 50 kDa molecular weight and are encoded by a VH gene at the N-terminus and one of the constant region genes (e.g., IgG1)

at the C-terminus. Similarly, full-length light chains are about 25 kDa molecular weight and are encoded by a V-region gene at the N-terminus and a constant region gene (preferably a kappa (κ) or lambda (λ) constant region gene) at the C-terminus.

The term "T cell epitope" refers to a peptide which is capable of binding MHC Class II, stimulating T cells, and/or binding to (without necessarily measurably activating) T cells in complex with MHC Class II. As used herein, this term is also used for convenience, to refer to the amino acid residue sequence of the epitope peptide.

The term "peptide" as used herein and in the appended claims, is a compound that includes two or more amino acids. The amino acids are linked together by a peptide bond (defined herein below). There are 20 different common naturally occurring amino acids involved in the biological production of peptides, and any number of them may be linked in any order to form a peptide chain or ring. The naturally occurring amino acids employed in the biological production of peptides all have the L-configuration, with the exception of glycine, which is not chiral. Synthetic peptides can be prepared employing conventional synthetic methods that are well known in the chemical art. Some peptides contain only a few amino acid units. Short peptides, e.g., having less than ten amino acid units, are sometimes referred to as "oligopeptides". Other peptides having a large number of amino acid residues, e.g. up to 100 or more, are often referred to as "polypeptides". By convention, a "polypeptide" may be considered as any peptide chain containing three or more amino acids, whereas a "oligopeptide" is usually considered as a particular type of "short" polypeptide. Thus, as used herein, it is understood that any reference to a "polypeptide" also includes an oligopeptide. Further, any reference to a "peptide" includes polypeptides, oligopeptides, and proteins. Each different arrangement of amino acids forms a different polypeptide or protein. The number of polypeptides, and hence the number of different proteins, that can be formed is practically unlimited.

An "alpha carbon" (Cα) is the carbon atom of the carbon-hydrogen (CH) component of an amino acid that is in the backbone chain of a peptide. The alpha carbon bears the amino and carboxylic acid moieties and the side chain of the amino acid. A "side chain" is a group that is pendant to alpha Cα, which can be a simple or complex group, and which has physical dimensions that can vary significantly compared to the dimensions of the peptide.

The terms "counterpart antibody" and "parental antibody" refer to an anti-TNF alpha antibody having the same human constant regions as a chimeric antibody of the invention, but having heavy chain and light chain variable regions that are identical to the non-human anti-TNF alpha monoclonal antibody to which the variable regions of the chimeric antibody are homologous. A preferred counterpart antibody is a chimeric A2 antibody, such as the WT cA2 antibody of Example 3, or the commercially available antibody known as infliximab. Each chimeric antibody of the present invention can be compared to its corresponding counterpart antibody and will have a lower immunogenic potential than its counterpart antibody.

As used herein in the appended claims, the term "polypeptide composition" and grammatical variations thereof refers to a single chain polypeptide, as well as a multiple chain polypeptide in which the polypeptide chains are chemically bound to each other, such as by one or more disulfide bonds between a cysteine residue in one chain and a cysteine residue on another chain, by an ester bond, an amide bond, or any other suitable linkage. TNF alpha binding polypeptide compositions include one or more polypeptide chain having a binding affinity for the TNF alpha antigen, preferably human TNF alpha antigen. TNF alpha binding polypeptide compositions of the invention include one or more TNF alpha binding polypeptide chains having a reduced number of human T cell epitopes as compared to the native heavy chain variable region (VH) and/or the native light chain variable region (VL) of monoclonal antibodies against human TNF alpha, such as A2. The term "polypeptide composition" also encompasses these polypeptides in a suitable carrier vehicle, which can be a liquid or a solid.

The present invention discloses amino acid residue sequences of potential T cell epitopes within the A2 variable region (V-region) of both the heavy chain (SEQ ID NO: 9) and light chain (SEQ ID NO: 10) of A2. The invention also discloses the major regions of the antibody V-region sequences from A2 that are immunogenic in man. When such immunogenic sequences are modified by substitution, deletion or addition of at least one amino acid residue, this results in reduction of the immunogenicity of the antibody in humans relative to a chimeric A2 antibody.

In one aspect, the invention provides a chimeric anti-TNF alpha antibody having a specificity for an antigen recognized by a non-human monoclonal anti-TNF alpha antibody. The chimeric antibody of the invention has human constant regions and has heavy chain and light chain variable regions that are homologous to the respective heavy chain and light chain variable regions of a non-human anti-TNF alpha monoclonal antibody, but including one or more amino acid residue substitutions, deletions or additions in the amino acid residue sequence of the variable region of the non-human monoclonal antibody. A chimeric antibody of the present invention has fewer MHC Class II recognition sites relative to its counterpart antibody, which affords a correspondingly lower level of immunogenicity in a human patients treated with the chimeric antibody.

A preferred chimeric anti-TNF alpha antibody of the invention has a specificity for an antigen recognized by the A2 antibody, but which is less immunogenic to humans than chimeric A2 having wild-type variable regions (i.e., the same variable regions as murine A2). This embodiment comprises human constant regions and includes modified heavy chain and light chain variable regions that are homologous the respective heavy chain and light chain variable regions of A2, but which includes one or more amino acid residue substitutions, deletions or additions in the amino acid residue sequence of the respective heavy chain and light chain variable regions of A2 antibody to reduce MHC Class II recognition of peptides derived from this region relative to a chimeric A2 having the wild-type variable regions.

In one specific embodiment, the present invention provides a TNF alpha-binding polypeptide composition including a modified heavy chain V-region selected from the group consisting of:

VH1, consisting of the amino acid residue sequence (SEQ ID NO: 1)
EVQLVESGGGLVQPGGSLRLSCAASGFTFSNHWMNWVRQSPEKGLEWVAE

IRSKSINSATHYAESVLGRFTISRDDSKNSLYLQMNSLKTEDTAVYYCSR

NYYGSTYDYWGQGTTLTVSS;

VH3, consisting of the amino acid residue sequence (SEQ ID NO: 2)
EVLLEESGGGLVQPGGSLRLSCAASGFTFSNHWMNWVRQSPEKGLEWVAE

IRSKSINSATHYAESVLGRFTISRDDSKNSLYLQMNSLKTEDTGVYYCSR

NYYGSTYDYWGQGTTVTVSS;

VH5, consisting of the amino acid residue sequence (SEQ ID NO: 3)
EVLLEESGGGLVQPGGSLRLSCAASGFTFSNHWMNWVRQSPEKGLEWVAE

TRSKSTNSATHYAESVLGRFTISRDDSKNSLYLQMNSLKTEDTGVYYCSR

NYYGSTYDYWGQGTTVTVSS; and

VH8, consisting of the amino acid residue sequence (SEQ ID NO: 4)
EVQLVESGGGLVQPGGSLRLSCAASGFTFSNHWMNWVRQSPEKGLEWVAE

TRSKSTNSATHYADSVLGRFTISRDDSKNSLYLQMNSLKTEDTAVYYCSR

NYYGSTYDYWGQGTLVTVSS.

In another embodiment, a TNF alpha-binding polypeptide composition of the present invention includes a modified light chain V-region selected from the group consisting of:

VL1, consisting of the amino acid residue sequence (SEQ ID NO: 5)
DIQLTQSPDTSSASPGERVSFSCRASQFVGSSIHWYQQRTNGSPRLLIKY

ASESMSGVPSRFSGSGSGTDFTLTINSLEAEDAATYYCQQSHSWPFTFGS

GTNVEVLR;

VL12, consisting of the amino acid residue sequence (SEQ ID NO: 6)
DIQLTQSPDTSSASPGERASFSCRASQFVGSSIHWYQHTTNGSPRLLIKY

SESMSGVPSRFSGSGSGTDFTLTINSLEAEDAATYYCQQSHSWPFTFGSG

TNLEVLR;

VL5, consisting of the amino acid residue sequence (SEQ ID NO: 7)
DIQLTQSPDTSSASPGERVSFSCRASQFVGSSIHWYQQRTNGSPRLLIKY

ASESMSGVPSRFSGSGSGTDFTLTINSLEAEDAATYYCQQSHSWPFTFGG

GTKVEIKR; and

VL8, consisting of the amino acid residue sequence (SEQ ID NO: 8)
DIQLTQSPDTSSASPGERASFSCRASQFVGSSIHWYQHTTNGSPRLLIKY

ASESMSGVPSRFSGSGSGTDFTLTINSLEAEDAATYYCQQSHSWPFTFGG

GTKVEIKR.

Other TNF alpha-binding polypeptide compositions of the present invention include a combination of a heavy chain variable region and a light chain variable region selected from the group consisting of: the heavy chain VH1 and the light chain VL1; the heavy chain VH1 and the light chain VL5; the heavy chain VH1 and the light chain VL8; the heavy chain VH5 and the light chain VL12; and the heavy chain VH8 and the light chain VL5.

Other preferred TNF alpha-binding polypeptide compositions of the present invention include a modified heavy chain variable region selected from the group consisting of:

a heavy chain V-region comprising the amino acid residue sequence of SEQ ID NO: 11, but which includes one or more substitutions selected from the group consisting of M18L, K19R, V23A, I28T, I51T, I56T, S79N, A80S, V81L, T86N, D87S, R89K, and L116V;

a heavy chain V-region comprising the amino acid residue sequence of SEQ ID NO: 11, but which includes one or more substitutions selected from the group consisting of K3Q, E5V, M18L, K19R, V23A, I28T, S79N, A80S, V81L, T86N, D87S, R89K, and G94A;

a heavy chain V-region comprising the amino acid residue sequence of SEQ ID NO: 11, but which includes one or more substitutions selected from the group consisting of M18L, K19R, V23A, I28T, S79N, A80S, V81L, T86N, D87S, R89K, and L116V; and a heavy chain V-region comprising the amino acid residue sequence of SEQ ID NO: 11, but which includes one or more substitutions selected from the group consisting of K3Q, E5V, M18L, K19R, V23A, I28T, I51T, I56T, E64D, S79N, A80S, V81L, T86N, D87S, R89K, G94A, T115L, and L116V.

In some embodiments, the TNF alpha-binding polypeptide composition of the invention includes a modified light chain variable region selected from the group consisting of:

a light chain V-region comprising the amino acid residue sequence of SEQ ID NO: 12, but which includes one or more substitutions selected from the group consisting of L3Q, A9D, I10T, L11S, V13A, V19A, Q38H, R39T, I58V, S74T, T77S, V78L, S80A, I83A, and D85T;

a V-region light chain comprising the amino acid residue sequence of SEQ ID NO: 12, but which includes one or more substitutions selected from the group consisting of L3Q, A9D, I10T, L11S, V13A, I58V, S74T, T77S, V78L, S80A, I83A, D85T, and L104V;

a V-region light chain comprising the amino acid residue sequence of SEQ ID NO: 12, but which includes one or more substitutions selected from the group consisting of L3Q, A9D, I10T, L11S, V13A, I58V, S74T, T77S, V78L, S80A, I83A, D85T, S100G, N103K, L104V, and V106I; and a V-region light chain comprising the amino acid residue sequence of SEQ ID NO: 12, but which includes one or more substitutions selected from the group consisting of L3Q, A9D, I10T, L11S, V13A, Q38H, R39T, I58V, S74T, T77S, V78L, S80A, I83A, D85T, S100G, N103K, L104V, and V106I.

Preferably, chimeric anti-TNF alpha antibody embodiments of the present invention comprise a human IgG1 constant region heavy chain domain and a human kappa constant region light chain domain in addition to a modified heavy chain variable region and/or a modified light chain variable region. A preferred heavy chain constant region has the amino acid sequence shown in SEQ ID NO: 164 in FIG. 19. A preferred light chain constant region has the amino acid sequence shown in SEQ ID NO: 165 in FIG. 20. The chimeric anti-TNF alpha antibodies of the present invention can bind to human TNF alpha and provide a protective effect to WEH1164 cells grown in otherwise lethal concentrations of TNF alpha in vitro. The antibodies of the present invention can also inhibit TNF alpha stimulated production of ICAM-1 in human endothelial cells in vitro; and can inhibit TNF alpha-stimulated production of IL-6 in human fibroblast cells in vitro.

In addition to a whole antibody (tetramer), TNF alpha-binding polypeptide compositions of the invention can exist in a number of other forms. These forms include for example Fv, Fab, Fab' and F(ab')$_2$ molecules. A further example includes a "bi-specific" antibody, i.e., an antibody comprising a first VH/VL combination of the present invention in combination with a second VH/VL combination having a different antigen specificity.

The ability of a polypeptide composition to stimulate an immune response in a human can be evaluated in vitro using an assay that measures the protein's effect on T cell activation and/or proliferation in a cell culture of human T cells, such as cultured human peripheral blood mononuclear cells (PBMC).

The proliferative affect of a polypeptide can be quantitatively assessed by any of a number of methods known in the art. One convenient method is a biological T cell assay such as described in Example 2. The assay involves testing overlapping peptides that are fragments of the heavy chain and/or light chain variable regions of a non-human anti-TNF alpha antibody, such as a peptide identified by calculation according to the method described in Example 1. Synthetic peptides are then prepared and evaluated for their ability to evoke a proliferative response in human T cells, such as PBMCs cultured in vitro.

A T cell proliferative response can be quantitatively measured by determination of $^3$H-thymidine incorporation. In this approach, naive human PBMCs taken from healthy donors are exposed to the peptides and a stimulation index (SI) is calculated. The SI is defined as the measured cell proliferation score (e.g. counts per minute, if using $^3$H-thymidine incorporation) for the test peptide, divided by the measured proliferation score in cells not contacted with a test peptide (see Example 11). A stimulation index equal to or greater than about 2 is a useful threshold value for determining the likelihood of the peptides to act as a T cell epitope. Accordingly, peptides having a stimulation index of less than 2, preferably less than about 1.8, are deemed to be less likely to elicit an in vivo immune response in a human than peptides having an SI of about 2 or greater. A TNF alpha-binding polypeptide composition of the present invention exhibits a smaller SI than its corresponding counterpart non-human anti TNF-alpha monoclonal antibody, as defined hereinabove.

In practice, a number of the TNF alpha-binding polypeptide compositions, such as chimeric anti TNF alpha antibodies, can be produced and tested for desirable immune and functional characteristics. It is particularly important, when altering the amino acid residue sequence of an antibody, that the sequence changes do not introduce new immunogenic epitopes. This can be avoided in practice by re-evaluating the contemplated modified amino acid residue sequence for the presence of epitopes and/or of MHC Class II ligands by any suitable means known in the art.

A particularly useful in vitro immunological assay is a recall assay involving PBMC preparations cultured in the presence of a priming quantity of test polypeptide composition (e.g., an antibody) followed by a re-challenge with either the same test protein, or in parallel, a modified version of the protein. Such an assay provides a convenient practical indication of whether an alteration of a potential epitope sequence will result in reduced immunogenic potential in a modified polypeptide, in the absence of a full-scale clinical trial. In most cases, the polypeptide variant will be produced by recombinant DNA techniques, although other procedures including chemical synthesis, can be used.

It is believed that TNF alpha-binding polypeptide compositions of the present invention exhibit a lower degree of immunogenicity due to the presence of fewer T cell epitopes in the modified variable region portions of the composition relative to the number of T cell epitopes in its corresponding counterpart antibody heavy chain and light chain variable regions. The lower level of immunogenicity is achieved by a reduction in numbers of epitopes or MHC allotypes able to bind peptides derived from the variable regions of the chimeric antibody relative to the number of epitopes in its counterpart antibody.

Another aspect of the present invention is an isolated polypeptide consisting of at least 9 consecutive amino acid residues and including an epitope region of a polypeptide selected from the group consisting of SEQ ID NO: 11 and SEQ ID NO: 12. FIG. 11 depicts a number of peptide sequences that are overlapping portions of SEQ ID NO: 11, which is the sequence of the heavy chain variable region and part of the heavy chain constant region of the WT cA2 antibody of Example 3. Each of the peptides CA1 through CA40 represents a contiguous segment of 15 amino acid residues from SEQ ID NO: 11. The amino acid residue sequence of each successively numbered peptide overlaps with the sequence of the previous peptide by 9 contiguous residues, advancing three residues for each sequentially numbered peptide. The sequences of peptides CA1-CA40 are segments of the heavy chain variable region and a portion of the IgG1 CH1 domain of the WT cA2 of Example 3 (SEQ ID NO: 11). The peptides were synthesized and tested for reactivity in a human T cell activation assay. The subset of peptides found to be positive in the assay represent potential T cell epitopes within the VH domain of A2.

In one preferred embodiment the isolated polypeptide is selected from the group of peptides CA1 through CA40, as depicted in FIG. 11, or a peptide consisting of at least 9 consecutive amino acid residues of any one of peptides CA1 through CA40. These peptides are useful as components of assay kits for determining the immunogenic potential of an anti-TNF alpha antibody and diagnostic kits for identifying subjects having immunological sensitivity to an anti-TNF alpha antibody such as the WT cA2 antibody of Example 3 or infliximab.

FIG. 12 depicts a number of peptide sequences that are overlapping portions of SEQ ID NO 12, which is the sequence of the light chain variable region and the kappa light chain constant region of the WT cA2 antibody of Example 3. Each of the peptides CA41 through CA75 represents a contiguous segment of 15 amino acid residues from SEQ ID NO: 12. The amino acid residue sequence of each successively numbered peptide overlaps with the sequence of the previous peptide by 9 contiguous residues, advancing three residues for each sequentially numbered peptide. The sequences of peptides CA41-CA75 are segments of the light chain variable region and a portion of the kappa constant region domain of WT cA2 (SEQ ID NO: 12). The peptides were synthesized and tested for reactivity in a human T cell activation assay. The subset of peptides found to be positive in the assay represent potential T cell epitopes within the VL domain of A2.

In another preferred embodiment, the isolated peptide is selected from the group of peptides CA41 through CA75, as depicted in FIG. 12, or a peptide consisting of at least 9 consecutive amino acid residues of any one of peptides CA41 through CA75. These peptides are useful as components of assay kits for determining the immunogenic potential of an anti-TNF alpha antibody and diagnostic kits for identifying subjects having immunological sensitivity to an anti-TNF alpha antibody such as the WT cA2 of Example 3 or infliximab.

In another preferred embodiment, the isolated peptide consists of at least 9 consecutive amino acid residues of a polypeptide selected from the group of peptides designated A-H, shown below, or a peptide having at least about 80% similarity, more preferably at least about 90% similarity to peptides A-H. Peptides A-D are epitope fragments of SEQ ID NO: 11. Peptides E-H are epitope fragments of SEQ ID NO: 12. These peptides are useful as components of an assay kit for determining the immunogenic potential of an anti-TNF alpha antibody, in diagnostic kits for identifying subjects having immunological sensitivity to an anti-TNF alpha antibody such as the WT cA2 of Example 3 or infliximab, and as therapeutic agents for inducing immunological tolerance to an anti-TNF alpha antibody prior to administering the antibody to a subject.

Peptides A-H have the following amino acid residue sequences:

| A. | GLVQPGGSMKLSCVAS; | (SEQ ID NO: 13) |
|---|---|---|
| B. | WVAEIRSKSINSA; | (SEQ ID NO: 14) |
| C. | SRDDSKSAVYLQMTDLRT; | (SEQ ID NO: 15) |
| D. | RNYYGSTYDYWGQGTTLTVSS. | (SEQ ID NO: 16) |
| E. | DILLTQSPAILSVSPGERVSF; | (SEQ ID NO: 17) |
| F. | HWYQQRTNGSPR; | (SEQ ID NO: 18) |
| G. | LIKYASESMSGIPS; | (SEQ ID NO: 19) |
| H. | DFTLSINTVESEDIADYYCQQ. | (SEQ ID NO: 20) |

The present invention also provides pharmaceutical compositions useful for treating TNF alpha-associated diseases and conditions such as Crohn's disease and arthritis. The pharmaceutical compositions comprise a TNF alpha-binding polypeptide composition of the invention, such as chimeric anti-TNF alpha antibody, together with a pharmaceutically acceptable carrier, diluent and/or excipient. Pharmaceutically acceptable carriers, diluents and excipients are well known in the pharmaceutical arts.

A TNF alpha-binding polypeptide composition having reduced immunogenicity to humans relative to its counterpart non-human anti TNF alpha monoclonal antibody can be prepared in the following manner. First, the amino acid residue sequence of the heavy chain and/or light chain variable regions (or a portion thereof) from a non-human anti-TNF alpha monoclonal antibody is determined. Second, one or more potential T cell epitopes within the amino acid residue sequence of the variable region of the non-human monoclonal antibody are identified by any suitable method, including, but not limited to, determination of the binding of the potential epitope peptides to MHC molecules using in vitro or in silico techniques or biological assays. Third, one or more modified variable region sequences are designed, which have one or more amino acid substitutions, deletions or additions within the identified potential T cell epitope sequence, so as to substantially reduce or eliminate the immunogenicity of the T cell epitope. The immunogenicity can be determined by the binding of the peptides to MHC molecules using in vitro or in silico techniques, or by biological assays. Next, peptides having the modified variable region sequence(s) are constructed by recombinant DNA techniques or chemical techniques, and the modified peptides are tested in an immunogenicity assay as described above. Optionally the peptides are tested in a TNF alpha binding assay. The assay results indicate whether the modified peptides have reduced immunogenic potential and suitable binding specificity for human TNF alpha. A TNF alpha-binding polypeptide composition, such as a chimeric antibody comprising human constant regions and the modified variable region(s) is then prepared by recombinant DNA techniques. The resulting chimeric antibody can be evaluated in the assay, as well. The foregoing steps can be repeated, as desired, until a chimeric antibody having a desirably low level of immunogenicity and high level of binding specificity is obtained.

Another aspect of the present invention is a method of manufacturing a chimeric anti-TNF alpha antibody comprising the steps of: (a) identifying one or more potential T cell epitope sequences in the amino acid residue sequence of at least one of the heavy chain variable region and the light chain variable region of a non-human monoclonal antibody that specifically binds to human TNF alpha; and (b) preparing a recombinant organism or cell line, such as a hybridoma, which expresses a chimeric anti-TNF alpha antibody that comprises a human heavy chain constant region, a human light chain constant region, and at least one heavy chain or light chain variable region that is homologous to the heavy chain or light chain variable region of said non-human monoclonal antibody, but which also includes an amino acid residue substitution, deletion, or addition in at least one potential T cell epitope identified in step (a). The identification of potential T cell epitopes according to step (a) can be carried out according to methods described in WO 98/59244; WO 98/52976; WO 00/34317, the relevant disclosures of which are incorporated herein by reference. Once a stable recombinant organism or cell line has been prepared, the antibody can be produced by culturing the recombinant organism or cell line in an appropriate culture medium and isolating chimeric anti-TNF alpha antibody that is expressed by the organism or cell line.

A significant feature of the chimeric antibody embodiments of the present invention is that they substantially retain the functional activities of their counterpart antibody. It is particularly desirable to produce a chimeric antibody that retains the therapeutic efficacy of the counterpart antibody, and which has a lower immunogenic potential than its counterpart antibody. The chimeric antibodies of the present invention have therapeutic efficacy in a number of important diseases and conditions in man, including rheumatoid arthritis, Crohn's disease, and a number of other clinical indications mediated by TNF alpha.

Preferably, the chimeric antibody of the present exhibits an affinity for its target antigen that is similar to the affinity exhibited by monoclonal antibody A2. The chimeric antibody of the invention recognizes TNF alpha and is capable of neutralizing TNF alpha activity in a range of in vitro assays. Such assays include cell cytotoxicity, mitogenesis, cytokine induction, and induction of adhesion molecule expression. In addition to neutralizing the biological activity of TNF alpha, the therapeutic efficacy of the antibody is believed also to be mediated by the ability of the antibody to induce antibody-dependent cell mediated cytotoxicity (ADCC) making it effective at killing cells that express cell surface bound forms of TNF alpha. The phenomenon of ADCC is mediated by the constant region domain of whole antibody molecules, and the chimeric antibodies of the present invention preferably include a constant region domain that is compatible with ADCC induction.

For the elimination of T cell epitopes, amino acid residue substitutions, deletions or additions are made at appropriate points within the amino acid residue sequence predicted by empirical or in silico techniques to achieve substantial reduction or elimination of the activity of the T cell epitope. Preferably, the T cell epitopes are eliminated by amino acid residue substitution. In practice an appropriate point within the variable region amino acid residue sequence will preferably equate to an amino acid residue that is involved in binding to one of the pockets within the MHC Class II binding groove.

It is most preferred to alter an amino acid residue of an epitope that participates in binding within the first pocket of the cleft at the so-called P1 or P1 anchor position of the peptide. The strength of binding interaction between the P1 anchor residue of an epitopic peptide and the first pocket of the MHC Class II binding groove is recognized as being a major determinant of overall binding affinity for the whole peptide. A particularly useful amino acid residue substitution is replacement of the anchor residue with a residue less readily accommodated within the pocket, for example, replacement of the anchor residue with to a relatively more hydrophilic amino acid residue. Amino acid residues in the peptide at positions directly involved in binding within other pocket regions of the MHC binding cleft are also suitable candidates for substitution.

Single amino acid residue substitutions within a given potential T cell epitope are the most preferred route by which the epitope may be eliminated. Combinations of more than one substitution within a single epitope can be used as well. Such multiple substitutions can be particularly appropriate where individually defined epitopes overlap with each other. Moreover, amino acid substitutions may be made even at positions not equating to the "pocket residues" of the MHC Class II binding groove, i.e., at any point within the peptide.

Another aspect of the present invention is a functional fragment of a chimeric anti-TNF alpha antibody of the invention, including, for example, an Fv, Fab, Fab' or F(ab')$_2$ fragment. Such fragments can be prepared by standard methods (for example, by the method of Coligan et al. *Current Protocols in Immunology*, John Wiley & Sons, 1991-1997). The antibody fragments comprise modified heavy chain and/or modified light chain variable regions as described hereinabove for the chimeric antibodies of the present invention. Such fragments include stabilized Fv fragments including single chain Fv forms (i.e., scFv) comprising a peptide linker joining the VH and VL domains, and an Fv stabilized by interchain disulphide linkage (i.e., dsFv) and which contain additional cysteine residues engineered to facilitate joining of the VH and VL domains. In addition, fragments such as "minibodies" and single variable domain antibodies "dAbs" can be used. The chimeric anti-TNF alpha antibodies of the invention also can include structures that increase the valency of the chimeric antibody V-region domain, such as multiple antigen binding sites, for example, by inclusion of dimerization domains (e.g. "leucine zippers") into the peptide or by other chemical modification strategies known in the art.

Example 1

Identification of Potential MHC Class II Ligands in Anti-TNF Alpha VH and VL Protein Sequence by Computational Means A preferred method for the analysis of peptide sequences with potential to act as MHC Class II binding ligands has been described in detail in WO 02/069232, the relevant disclosure of which is incorporated herein by reference. A software tool using this procedure has been developed and applied to the analysis of the anti-TNF alpha antibody V-region domains. The software includes a library of model MHC Class II molecules, encompassing a wide number of allotypic variants extant in the human population, and a library of peptide backbone structures, encompassing theoretical and known backbone conformations. Using these libraries, a large data set was generated based on the results of computationally docking each backbone conformation within each model MHC allotype binding groove. The data set includes the best side-chain conformation for all possible amino acids at the given backbone position. The interatomic distances between the peptide side-chains (in the optimum conformation) and the MHC protein are stored in this data set. A test amino acid residue sequence based on the protein of interest, but containing an amino acid residue substitution, addition, or deletion, is analyzed by adding its sequence of side-chains to all backbones and then retrieving the data sets for the optimum side-chain conformations, and then calculating a "peptide score" for each backbone. The best peptide score is selected for display and the process is repeated for each of the available MHC model structures.

The algorithm was applied to the analysis of the V-region domains of the anti-TNF alpha antibody A2. The analysis identified amino acid residue sequences of a number of 13 mer peptides, which are potential T cell epitopes due to their predicted ability to bind to one or more allotypes of MHC Class II ligands. The amino acid residue sequences of these peptides are shown in FIG. 13 (heavy-chain derived peptides) and FIG. 14 (light-chain derived peptides).

Example 2

Identification of T Cell Epitopes using Synthetic Peptides and Naive Human PBMC In Vitro Proliferation Assays The interaction between MHC, peptide and T cell receptor (TCR) provides the structural basis for the antigen specificity of T cell recognition. T cell proliferation assays evaluate the binding of peptides to MHC and the recognition of MHC/peptide complexes by the TCR. The in vitro T cell proliferation assays of the present example involve the stimulation of peripheral blood mononuclear cells (PBMCs), containing antigen presenting cells (APCs) and T cells. Stimulation is conducted in vitro using synthetic peptide antigens, and in some experiments whole protein antigen. Stimulated T cell proliferation is measured by determining the amount of $^3$H-thymidine ($^3$H-Thy) incorporated in the cells using scintillation counting of washed, fixed cells.

Buffy coats from human blood stored for less than 12 hours were obtained from the National Blood Service (Addenbrooks Hospital, Cambridge, UK). Ficoll-plaque was obtained from Amersham Pharmacia Biotech (Amersham, UK). Serum free AIM V media for the culture of primary human lymphocytes and containing L-glutamine, 50 µg/ml streptomycin, 10 µg/ml gentomycin and 0.1% human serum albumin was from Gibco-BRL (Paisley, UK). Synthetic peptides were obtained from Eurosequence (Groningen, The Netherlands) and Babraham Technix (Cambridge, UK).

Erythrocytes and leukocytes were separated from plasma and platelets by gentle centrifugation of buffy coats. The top phase (containing plasma and platelets) was removed and discarded. Erythrocytes and leukocytes were diluted 1:1 in phosphate buffered saline (PBS) before layering onto 15 ml ficoll-plaque (Amersham Pharmacia, Amersham UK). Centrifugation was performed according to the manufacturers recommended conditions and PBMCs were harvested from the serum+PBS/ficoll plaque interface. PBMCs were mixed with PBS (1:1) and collected by centrifugation. The supernatant was removed and discarded and the PBMC pellet resuspended in 50 ml PBS. The cells were repelleted by centrifugation and the PBS supernatant was discarded. The repelleted cells were resuspended using 50 ml AIM V media. At this point the cells were counted and the viability of the cells was assessed using trypan blue dye exclusion. Cells were again collected by centrifugation and the supernatant was discarded. Cells were resuspended for cryogenic storage at a density of about $3 \times 10^7$ cells per ml. The storage medium was 90% (v/v) heat inactivated AB human serum (Sigma, Poole, UK) and 10% (v/v) DMSO (Sigma, Poole, UK). Cells were transferred to a regulated freezing container (Sigma) and placed at about −70° C. overnight. When required for use, cells were thawed rapidly in a water bath at about 37° C. before transferring to 10 ml pre-warmed AIM V medium.

PBMC were stimulated with protein and peptide antigens in a 96-well flat bottom plate at a density of about $2 \times 10^5$ PBMC per well. PBMC were incubated for about 7 days at about 37° C. before pulsing with $^3$H-Thy (Amersham-Phamacia, Amersham, UK). For the present study, synthetic peptides (15 mers) spanning the entire V-region domains of both the heavy chain and light chain of the WT cA2 antibody of Example 3 were produced (See FIGS. 11 and 12). Each peptide overlapped each successive peptide in the sequence by 12 residues, i.e., each peptide incremented from the next in the sequence by 3 residues. Each peptide was screened individually against PBMC's isolated from 20 naive donors. Two control peptides C32 (PKYVLQNTLKLAT; SEQ ID NO: 21) and C49 (KVVDQIKKISKPVQH; SEQ ID NO: 22) that have previously been shown to be immunogenic and a potent non-recall antigen KLH were used in each donor assay. Peptides were dissolved in DMSO to a final concentration of 10 mM, these stock solutions were then diluted at about 1/500 in AIM V media (final concentration about 20 µM). Peptides were distributed in a flat bottom 96-well plate to afford final peptide concentrations of about 2 and about 10 µM in 100 µl. The viability of thawed PBMC's was assessed by trypan blue dye exclusion, cells were then resuspended at a density of about $2 \times 10^6$ cells/ml, and about 100 µl ($2 \times 10^5$ PBMC/well) was transferred to each well containing peptides. Triplicate well cultures were assayed at each peptide concentration. Plates were incubated for about 7 days in a humidified atmosphere of about 5% $CO_2$ at about 37° C. Cells were pulsed for about 18-21 hours with about 1 µCi of $^3$H-Thymidine per well before harvesting onto filter mats. Counts Per Minute (CPM) values were determined using a Wallac microplate beta top plate counter (Perkin Elmer). Results were expressed as stimulation indices (SI), where SI=CPM of the test peptide divided by the CPM of untreated control.

Mapping T cell epitopes in the WT cA2 V-region sequences using the naive T cell proliferation assay resulted in the identification of several immunogenic regions. Peptides with significant stimulation indices in individual donors include, for example, CA34 (SI=2.22) and CA52 (SI=2.09).

The map was refined in sequence regions surrounding the complementarity determining regions (CDRs) for the VH and the VL sequences using a further sub-set of 15 different 13-mer peptides (P1-P15) from the peptides shown in FIG. 13 and FIG. 14:

| | | |
|---|---|---|
| P1 = KGLEWVAEIRSKS, | (SEQ ID NO: 107) |
| P2 = EWVAEIRSKSINS, | (SEQ ID NO: 109) |
| P3 = AEIRSKSINSATH, | (SEQ ID NO: 110) |
| P4 = KSINSATHYAESV, | (SEQ ID NO: 111) |
| P5 = TGVYYCSRNYYGS, | (SEQ ID NO: 121) |
| P6 = STYDYWGQGTTLT, | (SEQ ID NO: 126) |
| P7 = SQFVGSSIHWYQQ, | (SEQ ID NO: 135) |
| P8 = QFVGSSIHWYQQR, | (SEQ ID NO: 136) |
| P9 = SSIHWYQQRTNGS, | (SEQ ID NO: 137) |
| P10 = HWYQQRTNGSPRL, | (SEQ ID NO: 139) |
| P11 = PRLLIKYASESMS, | (SEQ ID NO: 140) |
| P12 = RLLIKYASESMSG, | (SEQ ID NO: 141) |
| P13 = LLIKYASESMSGI, | (SEQ ID NO: 142) |
| P14 = IKYASESMSGIPS, | (SEQ ID NO: 143) |
| P15 = ESMSGIPSRFSGS. | (SEQ ID NO: 144) |

Figure 5:
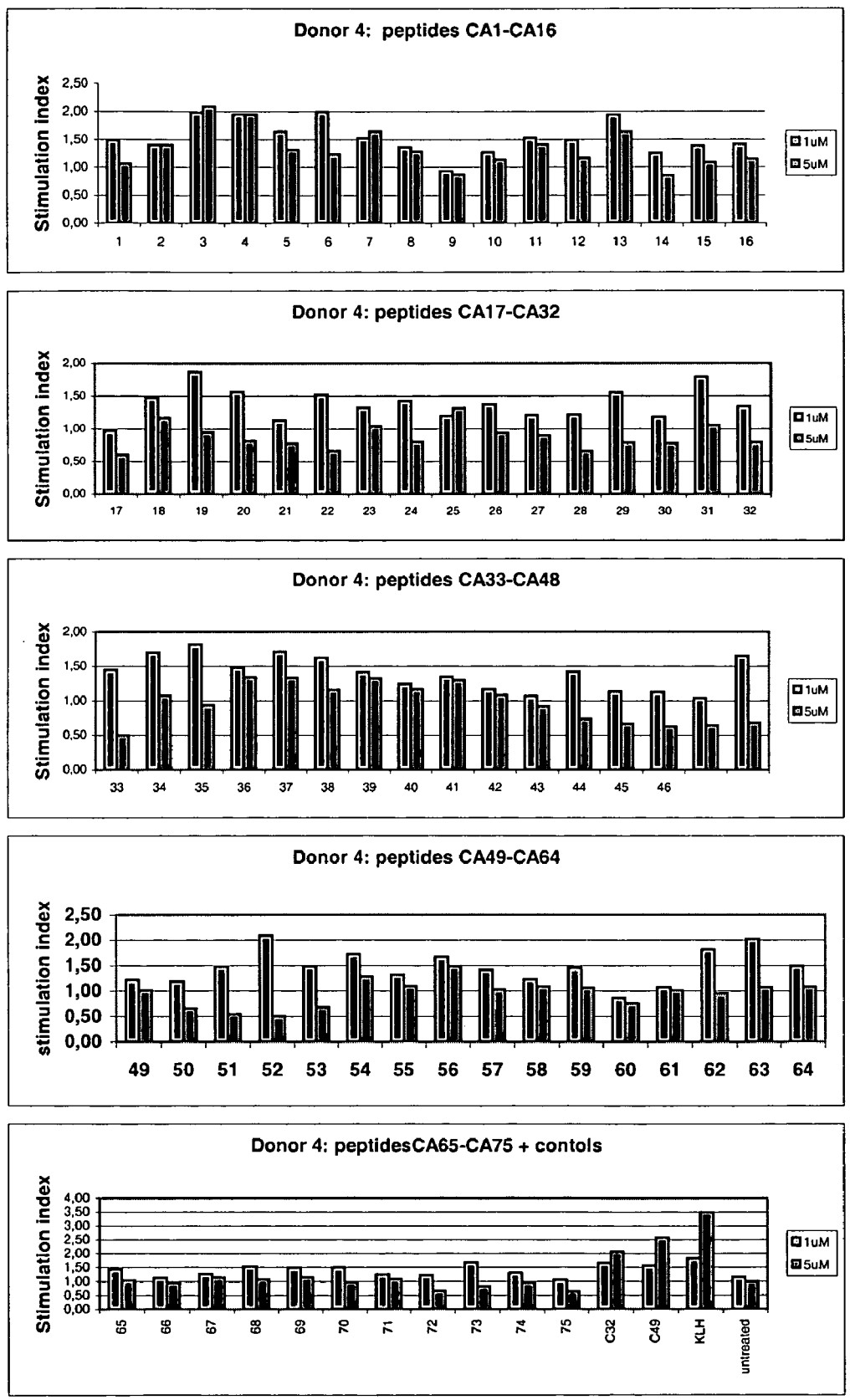
FIG. 5 provides a panel of histograms representing the proliferation response to synthetic peptides in an in vitro naive T cell proliferation assay. The data relate to the responses by peripheral blood mononuclear cells (PBMC) from an individual donor (#4) and are presented for each of peptides CA1-CA75 at both 1 μM and 5 μM concentration. The graphs each plot the Stimulation Index (SI) versus the peptide identification number. SI=CPM Test Peptide/CPM untreated control. Peptide sequences and methods are detailed in Example 2 and in FIGS. 11 and 12.

Peptides P1-P7 derive from the VH chain sequence and peptides P8-P15 derive from the VL chain sequence. Peptides P1-P15 were screened for their ability to evoke an in vitro proliferative response in a further panel of 10 naive PBMC preparations encompassing multiple different MHC allotypes as described above. The results of the naive T cell proliferation assay from both sets of synthetic peptides and donor panels can be taken together to produce an epitope map of the VH and VL chains of the antibody. An SI of greater than about 1.95 is taken as a significant (i.e., positive) response. Representative histograms showing the SI for each of peptides P1-P15 for one responsive donor are provided in FIG. 5. Exemplary assay results for the 13-mer peptides P1-P15 are provided in FIG. 6.

Example 3

Construction of Anti-TNF Alpha Antibody VH and VL Genes

The sequences of the A2 antibody variable regions were derived from U.S. Pat. No. 5,656,272 (see FIGS. 16a and 16b of U.S. Pat. No. 5,656,272). A gene (VH gene; SEQ ID NO: 160; FIG. 15) encoding the variable domain heavy chain of A2 (SEQ ID NO: 9) and a human IgG1 constant domain (SEQ ID NO: 164) was prepared by standard DNA synthesis techniques. The amino acid residue sequence encoded by the VH gene is shown in FIG. 16, SEQ ID NO: 161. A gene (VL gene; SEQ ID NO: 162; FIG. 17) encoding the variable domain light chain of A2 (SEQ ID NO: 10) and a human kappa constant domain (SEQ ID NO: 165) also was prepared by standard DNA synthesis techniques. The amino acid residue sequence encoded by the VL gene is shown in FIG. 18, SEQ ID NO: 163.

In preparing the genes, a panel of synthetic oligonucleotides were designed and synthesized, and the genes were assembled using a ligase chain reaction (LCR) in which oligonucleotides having complementary ends were annealed, and then amplified and filled-in using a polymerase chain reaction (PCR). The PCR was driven by addition of an increased concentration of the flanking oligonucleotides to act as primers. The PCR products were assembled into full-length antibody genes by further PCR from vectors containing 5' and 3' immunoglobulin gene flanking regions and sub-cloning the resulting polynucleotides into expression vectors for expression of whole antibody. The assembled VH and VL genes served as templates for mutagenesis and construction of multiple variant antibody sequences in which T cell epitopes had been removed but amino acid residue substitution.

Figure 1F:
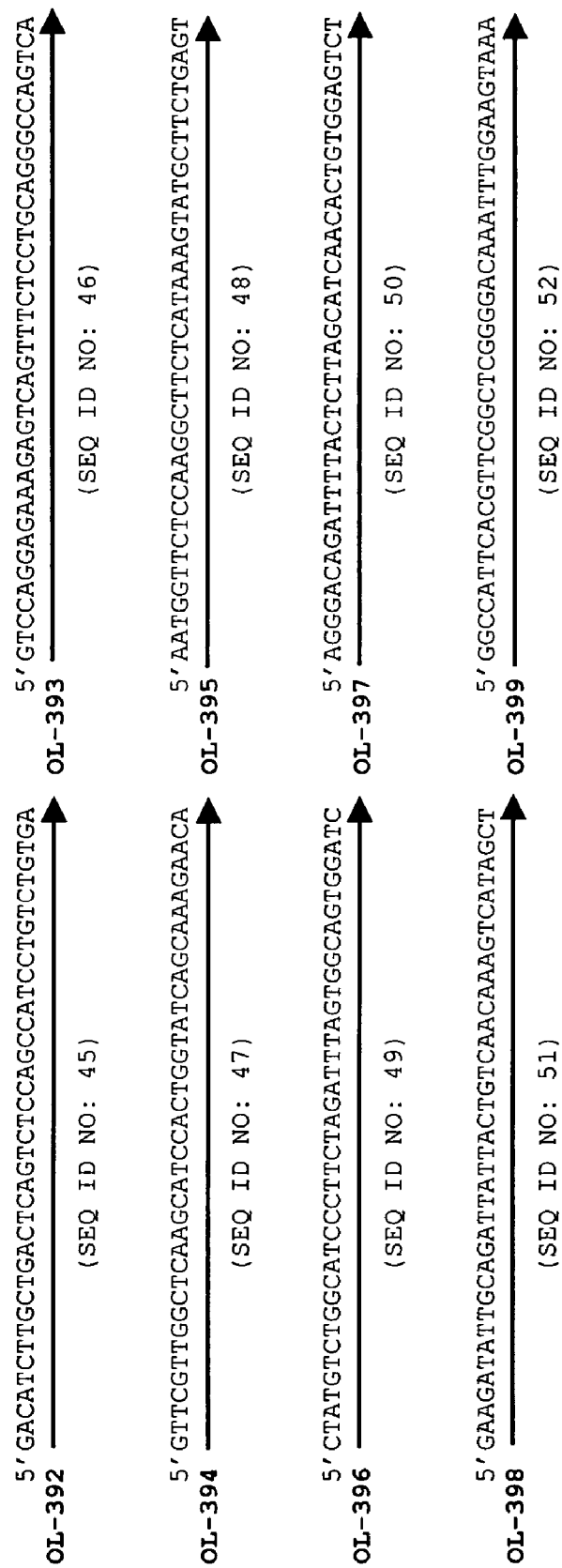
Figure 1G:
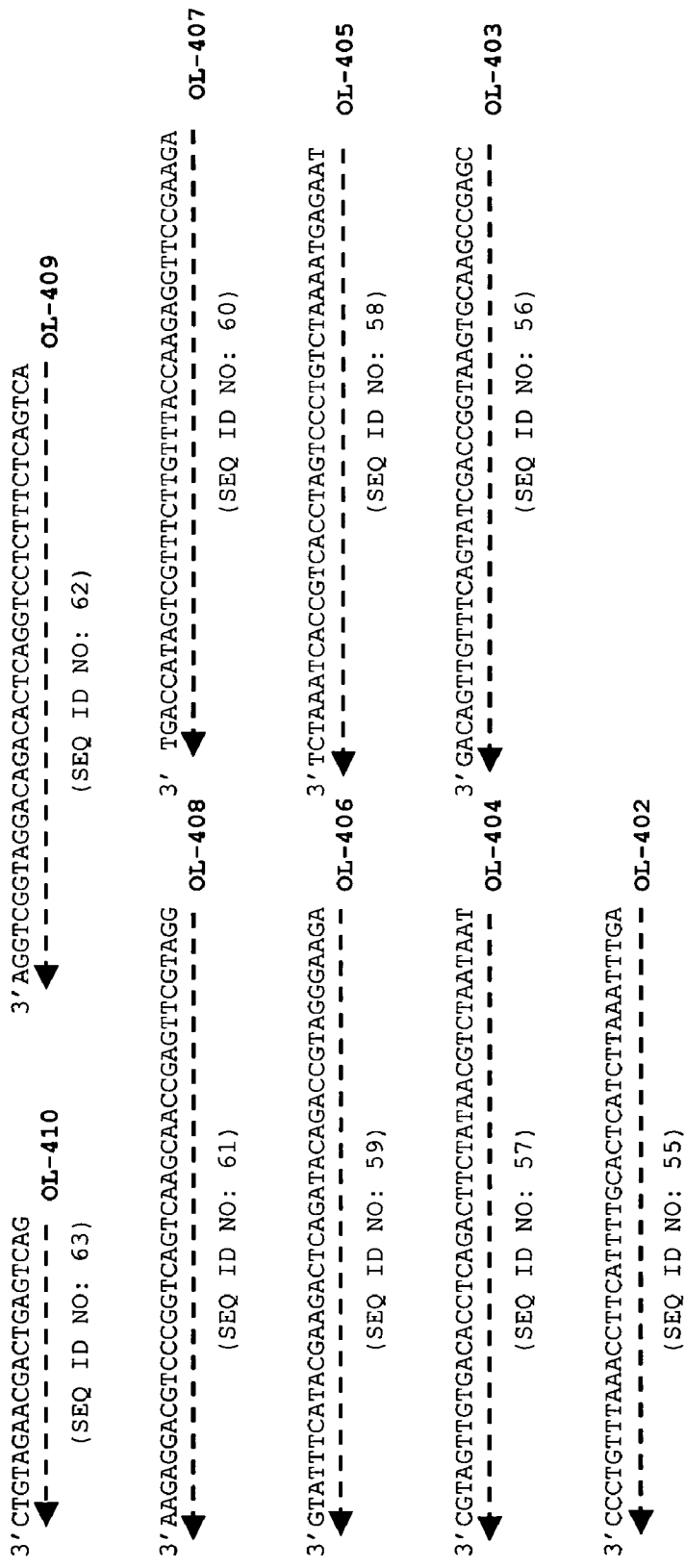
Figure 1H:
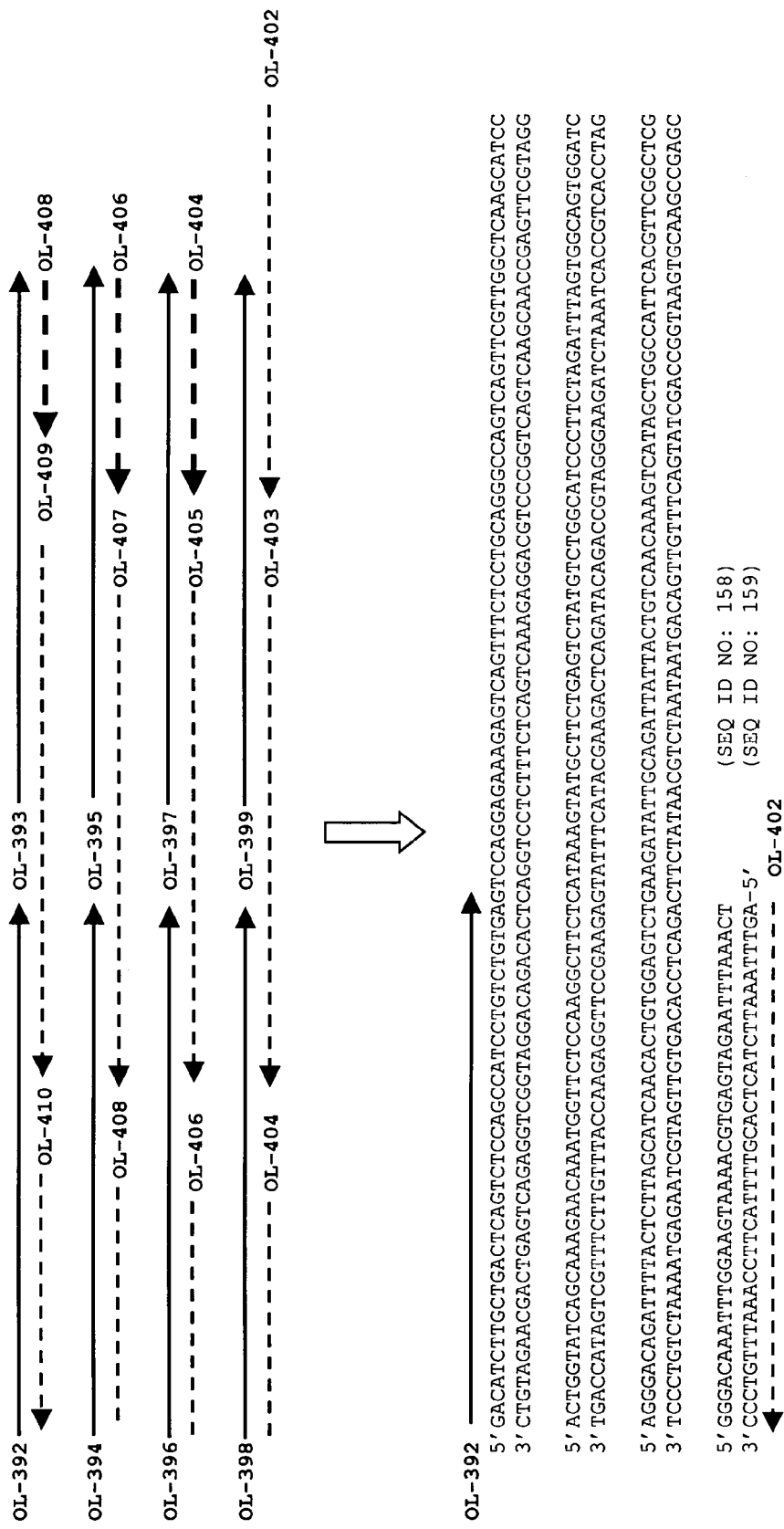
Figure 1I:
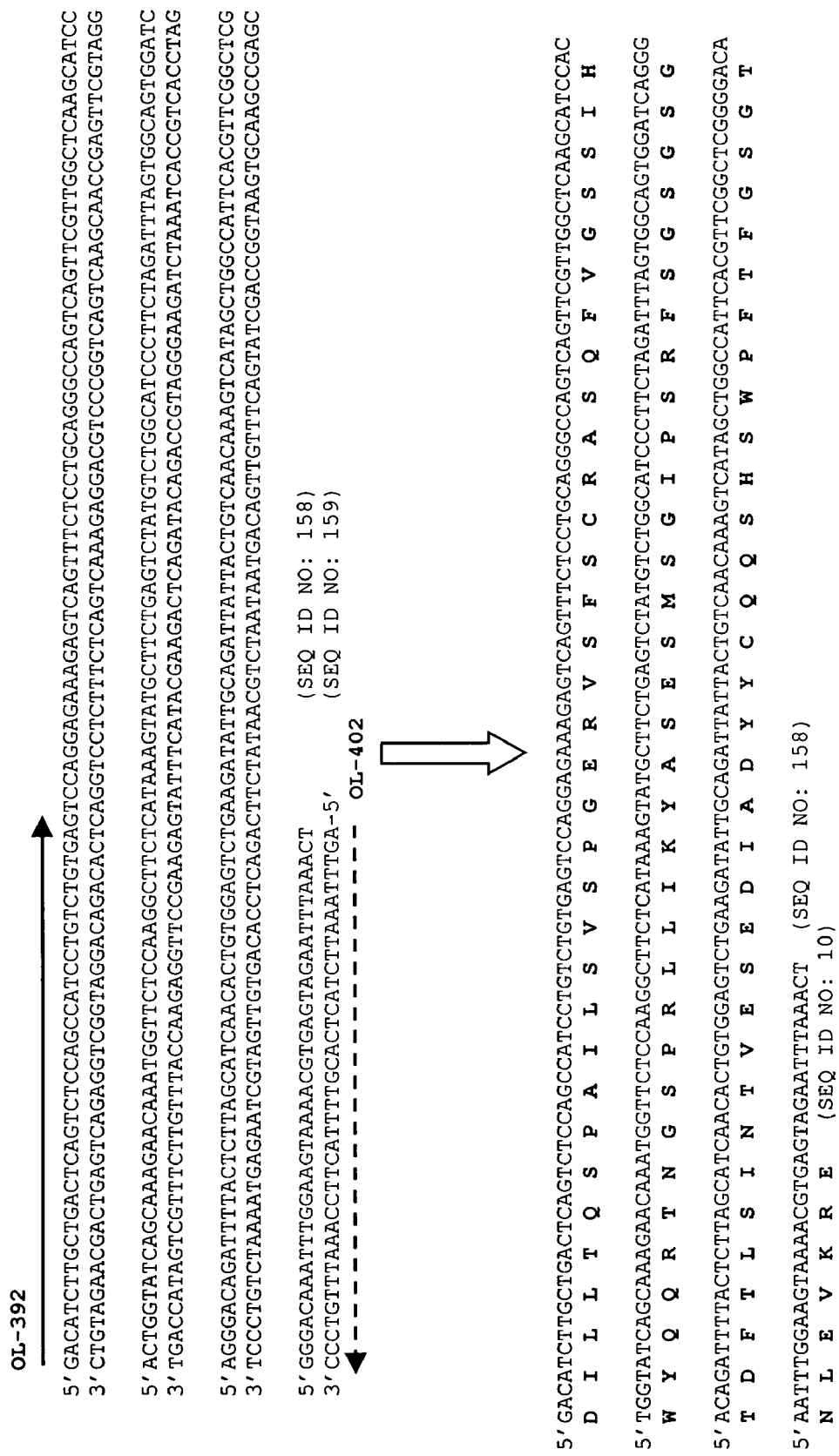

For assembly of the VH gene, oligonucleotides OL373-OL391, shown in Table 2 and FIGS. 1A and 1B, were used. For assembly of the VL gene oligonucleotides OL392-OL410 shown in Table 3 and FIGS. 1F and 1G were used. For both genes, the LCR was conducted by mixing about 20 μl of phosphorylated oligonucleotides with about 1 μl Pfu DNA ligase (Stratagene, Amsterdam, NL), about 10 μl of 10× reaction buffer (supplied with enzyme), and about 69 μl water. The reaction mix was placed in a thermal cycler for incubation at about 95° C. for about 2 minutes followed by 25 cycles of about 95° C. for about 30 seconds, followed by gradual cooling to about 60° C. then incubation at about 60° C. for about 20 minutes and a final incubation of about 3 hours at about 60° C. Typically, analysis of a sample of the LCR using 2% agarose gel electrophoresis gave a smear with a faint band of correct size just visible. The oligonucleotides in all cases were from were from MWG-Biotech (Ebersberg, Germany) and were phosphorylated in vitro using T4 DNA kinase (Roche, Lewes, UK), following the supplier's recommended protocol. Following LCR, 5 μL of the reaction was transferred to a PCR mixture to amplify the assembled fragment. Oligonucleotides OL373 and OL382 were used as primers to prepare the VH oligonucleotides and oligonucleotides OL392 and OL401 used as primers to prepare the VL oligonucleotide. PCR was conducted in a total volume of about 50 μl for 15 cycles using Taq DNA polymerase (Roche, Lewes, UK). The reaction mixture was separated on a 1% agarose gel and the desired band was removed and purified using a Qiagen (Crawley, UK) DNA extraction kit. The isolated DNA products from the bands were directly cloned into the pGemT-easy vector (Promega, Southampton, UK) for sequence analysis. Several clones were sequenced until correct clones were obtained.

Full-length immunoglobulin genes containing the variable region cassettes of the VH and VL regions produced above were assembled using overlapping PCR. DNA of the vectors M13-VHPCR1 and M13-VLPCR1 (Orlandi et al., (1989), PNAS, 89: 3833-7) were used as templates to produce two additional overlapping PCR fragments for each VH and VL chains including 5' flanking sequence with the murine heavy chain immunoglobulin promoter and encoding the leader signal peptide and 3' flanking sequence including a splice site and intron sequences. The DNA fragments so produced for each VH and VL were combined in a PCR reaction using flanking primers required to obtain full-length DNA sequences. The primer pairs used in these "linking" reactions were oligonucleotides OL411/OL413 and OL414/OL415 for the VH gene, whereas for the VL gene, the oligonucleotides OL411/OL412 and OL411/OL401 were used.

The heavy chain gene, complete with 5' and 3' flanking sequences, was cloned into the expression vector pSVgpt (Reichmann et al., (1988) Nature, 332: 323) which includes a segment encoding the human IgG1 constant region domain (Takahashi et al., (1982) Cell, 29: 671) and also contains the guanine phosphoribosyl transferase (gpt) gene for selection in mammalian cells. The light chain gene, complete with 5' and 3' flanking sequences, was cloned into the expression vector pSVHyg (Reichmann et al., ibid) in which the gpt gene is replaced by the gene for hygromycin resistance (hyg) and includes a human kappa constant region domain (Heiter et al., (1980) Cell, 22: 197). For both vectors, the fully assembled heavy chain or light chain genes were sub-cloned as HindIII/BamHI fragments purified by gel electrophoresis and handled using well known procedures and reagent systems.

TABLE 2

Synthetic oligonucleotides for VH

| Name | Sequence | SEQ ID NO: |
|---|---|---|
| OL 373 | GAAGTGAAGCTGGAGGAGTCTGGAGGCGGCTTGGTGCAAC | 23 |
| OL 374 | CTGGAGGCTCCATGAAACTCTCCTGTGTTGCCTCTGGATT | 24 |
| OL 375 | CATTTTCAGTAACCACTGGATGAACTGGGTCCGCCAGTCT | 25 |
| OL 376 | CCAGAGAAGGGGCTTGAGTGGGTTGCTGAAATTAGATCAA | 26 |
| OL 377 | AATCGATTAATTCTGCAACACATTATGCGGAGTCTGTGAA | 27 |
| OL 378 | AGGGAGGTTCACCATCTCAAGAGATGATTCCAAAAGTGCT | 28 |
| OL 379 | GTGTACCTGCAAATGACCGACCTGAGAACTGAAGACACTG | 29 |
| OL 380 | GCGTTTATTACTGTTCCAGGAATTACTACGGTAGTACCTA | 30 |
| OL 381 | CGACTACTGGGGCCAAGGCACCACTCTCACAGTGTCCTCAGG | 31 |
| OL 382 | CCTGAGGACACTGTGAGAGTGG | 32 |
| OL 383 | TGCCTTGGCCCCAGTAGTCGTAGGTACTACCGTAGTAATT | 33 |
| OL 384 | CCTGGAACAGTAATAAACGCCAGTGTCTTCAGTTCTCAGG | 34 |
| OL 385 | TCGGTCATTTGCAGGTACACAGCACTTTTGGAATCATCTC | 35 |
| OL 386 | TTGAGATGGTGAACCTCCCTTTCACAGACTCCGCATAATG | 36 |
| OL 387 | TGTTGCAGAATTAATCGATTTTGATCTAATTTCAGCAACC | 37 |
| OL 388 | CACTCAAGCCCCTTCTCTGGAGACTGGCGGACCCAGTTCA | 38 |
| OL 389 | TCCAGTGGTTACTGAAAATGAATCCAGAGGCAACACAGGA | 39 |
| OL 390 | GAGTTTCATGGAGCGTCCAGGTTGCACCAAGCCGCCTCCA | 40 |
| CL 391 | GACTCCTCCAGCTTCACTTC | 41 |
| CL 413 | AGACTCCTCCAGCTTCACTTCGGAGTGGACACCTGTGGAG AG | 42 |
| CL 414 | ACCACTCTCACAGTGTCCTCAGGTGAGTCCTTACAACCTC TC | 43 |
| CL 415 | TTGGGATCCTATAAATCTCTGGCC | 44 |

TABLE 3

Synthetic oligonucleotides for VL

| Name | Sequence | SEQ ID NO: |
|---|---|---|
| OL 392 | GACATCTTGCTGACTCAGTCTCCAGCCATCCTGTCTGTGA | 45 |
| OL 393 | GTCCAGGAGAAAGAGTCAGTTTCTCCTGCAGGGCCAGTCA | 46 |

TABLE 3-continued

Synthetic oligonucleotides for VL

| Name | Sequence | SEQ ID NO: |
|---|---|---|
| OL 394 | GTTCGTTGGCTCAAGCATCCACTGGTATCAGCAAAGAACA | 47 |
| OL 395 | AATGGTTCTCCAAGGCTTCTCATAAAGTATGCTTCTGAGT | 48 |
| OL 396 | CTATGTCTGGCATCCCTTCTAGATTTAGTGGCAGTGGATC | 49 |
| OL 397 | AGGGACAGATTTTACTCTTAGCATCAACACTGTGGAGTCT | 50 |
| OL 398 | GAAGATATTGCAGATTATTACTGTCAACAAAGTCATAGCT | 51 |
| OL 399 | GGCCATTCACGTTCGGCTCGGGGACAAATTTGGAAGTAAA | 52 |
| OL 400 | ACGTGAGTAGAATTTAAACTTTGCTTCCTCAGTTGGATCCT GGCAGAGTC | 53 |
| OL 401 | GACTCTGCCAGGATCCAACTGAGGAAGCAA | 54 |
| OL 402 | AGTTTAAATTCTACTCACGTTTTACTTCCAAATTTGTCCC | 55 |
| OL 403 | CGAGCCGAACGTGAATGGCCAGCTATGACTTTGTTGACAG | 56 |
| OL 404 | TAATAATCTGCAATATCTTCAGACTCCACAGTGTTGATGC | 57 |
| OL 405 | TAAGAGTAAAATCTGTCCCTGATCCACTGCCACTAAATCT | 58 |
| OL 406 | AGAAGGGATGCCAGACATAGACTCAGAAGCATACTTTATG | 59 |
| OL 407 | AGAAGCCTTGGAGAACCATTTGTTCTTTGCTGATACCAGT | 60 |
| OL 408 | GGATGCTTGAGCCAACGAACTGACTGGCCCTGCAGGAGAA | 61 |
| OL 409 | ACTGACTCTTTCTCCTGGACTCACAGACAGGATGGCTGGA | 62 |
| OL 410 | GACTGAGTCAGCAAGATGTC | 63 |
| OL 411 | TTACGCCAAGCTTATGAATATGCAAATCC | 64 |
| OL 412 | AGACTGAGTCAGCAAGATGTCGGAGTGGACACCTGTGGAG AG | 65 |

Example 4

Construction of Modified Antibody VH and VL Genes

A modified VL gene was prepared, which encodes a modified light chain variable region polypeptide termed VL1 (SEQ ID NO: 1). VL1 includes mutations L3Q, A9D, I10T, L11S, V13A, I58V, S74T, T77S, V78L, S80A, I83A, D85T and L104V in SEQ ID NO: 10. The gene encoding VL1 was constructed by gene synthesis techniques described in Example 3. Table 4 lists the oligonucleotides used in the assembly of the VL1 gene. These oligonucleotides were used, together with OL393, OL394, OL395, OL400, OL401, OL403, OL405, OL407 and OL408 as described in Example 3. The gene was cloned into the pGEM-T easy vector (Promega) and several clones were sequenced until a correct clone was obtained. Assembly of the full-length immunoglobulin gene and sub-cloning to the expression vector was also performed as in Example 3, with the exception that oligonucleotides OL411 and OL469 were used in the linking reaction for the VL gene.

Additional mutations were introduced in the VL gene to make further variant VL polypeptides. These variant VL polypeptides include substitutions: V19A, Q38H, R39T, S100G, N103K, V106I in SEQ ID NO: 10. The mutagenesis was conducted by PCR using the oligonucleotides listed in Table 5. OL768 and OL769, OL770 and OL771 were used in overlap PCR, in combination with OL411 and OL401 (as described above). OL648 was used in a single PCR in combination with OL411. The PCR products were cloned into pGEM-T Easy (Promega) and a correct clone was identified by sequencing.

Variant VH genes were also constructed from the wild-type sequence (SEQ ID NO: 10) using mutagenesis. Variant VH genes encoding the substitutions K3Q, E5V, M18L, K19R, V23A, I28T, I51 T, I56T, E64D, S79N, A80S, V81L, T86N, D87S, R89K, G94A, T115L and L116V in SEQ ID NO: 10 were constructed. These mutations were introduced using the oligonucleotides listed in Table 6. Each set of oligonucleotides was used in overlap PCR, in combination with OL411 and OL415. The PCR products were cloned into pGEM-T Easy (Promega) and a correct clone identified by sequencing.

The VH or VL domains were sub-cloned into the expression vectors as HindIII/BamHI fragments as previously and variant antibodies expressed according to the method of Example 5. Each of the heavy chains included a constant region having the amino acid sequence identified as SEQ ID NO: 164 in FIG. 19, which is the same sequence utilized in Example 3 for the WT cA2 heavy chain. Each of the light chains included a constant region having the amino acid sequence identified as SEQ ID NO: 165 in FIG. 20, which is the same sequence utilized in Example 3 for the WT cA2 light chain.

TABLE 4

Synthetic oligonucleotides for VL1 assembly

| Name | Sequence | SEQ ID NO: |
|---|---|---|
| OL 459 | GACATCCAGCTGACTCAGTCTCCAGACACCTCCTCTGCCA | 66 |
| OL 460 | CTATGTCTGGCGTGCCTTCTAGATTTAGTGGCAGTGGATC | 67 |
| OL 461 | AGGGACAGATTTTACTCTTACCATCAACTCCCTGGAGGCC | 68 |
| OL 462 | GAAGATGCCGCAACCTATTACTGTCAACAAAGTCATAGCT | 69 |
| OL 463 | GGCCATTCACGTTCGGCTCGGGGACAAATGTGGAAGTAAA | 70 |
| OL 464 | AGTTTAAATTCTACTCACGTTTTACTTCCACATTTGTCCC | 71 |
| OL 465 | TAATAGGTTGCGGCATCTTCGGCCTCCAGGGAGTTGATGG | 72 |
| OL 466 | AGAAGGCACGCCAGACATAGACTCAGAAGCATACTTTATG | 73 |
| OL 467 | ACTGACTCTTTCTCCTGGACTGGCAGAGGAGGTGTCTGGA | 74 |
| OL 468 | GACTGAGTCAGCTGGATGTC | 75 |
| OL 469 | AGACTGAGTCAGCTGGATGTCGGAGTGGACACCTGTGGAG AG | 76 |

TABLE 5

Synthetic oligonucleotides for VL mutageneis

| Name | Sequence | SEQ ID NO: |
|---|---|---|
| OL 648 | GGATCCAACTGAGGAAGCAAAGTTTAAATTCTACTCACG TTTGATTTCCACCTTTGTCCCGCCGCCGAACGTGAATGGCC | 77 |
| OL 768 | AGTCCAGGAGAAAGAGCCAGTTTCTCCTGCAGG | 78 |

TABLE 5-continued

Synthetic oligonucleotides for VL mutageneis

| Name | Sequence | SEQ ID NO: |
|---|---|---|
| OL 769 | CCTGCAGGAGAAACTGGCTCTTTCTCCTGGACT | 79 |
| OL 770 | CCACTGGTATCAGCACACAACAAATGGTTCTCCAA | 80 |
| OL 771 | TTGGAGAACCATTTGTTGTGTGCTGATACCAGTGG | 81 |

TABLE 6

Synthetic oligonucleotides for VH mutagenesis

| Name | Sequence | SEQ ID NO: |
|---|---|---|
| OL 642 | GTCTGAGGGAGCCTCCAGGTTGCACCAAGCCGCCTCCAGACTCCACCAGCTGCACTTCGGAG | 82 |
| OL 643 | AACCTGGAGGCTCCCTGAGACTCTCCTGTGCTGCCTCTGGATTCACTTTCAGTAACCACTGG | 83 |
| OL 644 | AGGCTGTTCATTTGCAGGTACAGAGAATTTTTGGAATCATC | 84 |
| OL 645 | TACCTGCAAATGAACAGCCTGAAAACTGAAGACACTGCCGTTTATTACTG | 85 |
| OL 654 | GAAACTAGATCAAAATCGACTAATTCTGCA | 86 |
| OL 655 | ATTAGTCGATTTTGATCTAGTTTCAGCAAC | 87 |
| OL 656 | CACATTATGCGGACTCTGTGAAAGGG | 88 |
| OL 657 | CCCTTTCACAGAGTCCGCATAATGTG | 89 |
| OL 658 | GGCCAAGGCACCCTTGTCACAGTGTCCTCA | 90 |
| OL 659 | TGAGGACACTGTGACAAGGGTGCCTTGGCC | 91 |
| OL 899 | GCCAAGGCACCACTGTCACAGTGTCCTCAGG | 92 |
| OL 900 | CCTGAGGACACTGTGACAGTGGTGCCTTGGC | 93 |

Example 5

Expression, Purification and Quantitation of Anti-TNF Alpha Antibodies

Various combinations of the heavy and light chain expression vectors prepared in Example 4 were co-transfected using electroporation into NS/0 cells, a non-immunoglobulin producing mouse myeloma cell line, obtained from the European Collection of Animal Cell Cultures (ECACC Acc #85110503). Colonies expressing the gpt gene were selected in Dulbecco's Modified Eagles Medium (DMEM) supplemented with 10% (v/v) fetal calf serum and antibiotics (all from Gibco, Paisley, UK) and with 0.8 µg/ml mycophenolic acid and 250 µg/ml xanthine (Sigma, Poole, UK).

Production of human antibody by transfected cell clones was measured by ELISA for human IgG (Tempest et al (1991) BioTechnology 9: 266). Cell lines that secreted the antibody were expanded and the antibody was purified by protein A affinity chromatography (Harlow, et al.; in Antibodies a Laboratory Manual, pp 309; Cold Spring Harbor Laboratory Press (1988), NY, USA).

The concentration of the purified antibody was determined using an ELISA detecting the human kappa constant region of the antibodies of interest. A standard concentration curve was determined for a commercial preparation of the therapeutic antibody infliximab (Schering-Plough Ltd., UK), and this standard was used to compute the concentration of the test antibody preparation. The assay was conducted in 96-well plates and all determinations were conducted in duplicate.

For the assay, plates (Dynatech Immulon 2) were coated using 100 µl per well of sheep anti-human Kappa antibody (The Binding Site, Birmingham, UK) diluted 1:250 in carbonate/bicarbonate coating buffer pH 9.6 (Sigma, Poole, UK). Coating was conducted for about 1 hour at about 37° C. and the wells were washed 3 times with PBS-T (PBS with 0.05% in Tween 20). The wells were filled with 100 µl of PBS-T and the dilutions for the control and test antibodies set out. The negative control uses PBS-T only, no antibody was added. The standard preparation of infliximab was diluted 1:1000 (v/v) and a doubling dilution series set out across the plate. Doubling dilution series were also set out for the test antibody preparations. The plate was incubated at room temperature for about 1 hour, and the wells were washed as previously described. Bound antibody was detected using a peroxidase conjugated sheep ant-human IgG (gamma chain specific reagent (The Binding Site, Birmingham, UK). This secondary antibody was diluted 1:1000 in PBS-T and 100 µl added to each well of the plate. The plate was incubated for a further 1 hour at room temperature and washed as previously. Detection was achieved using 100 µl per well of SIGMA-FAST® peroxidase substrate (Sigma, Poole, UK) and the color development stopped by addition of about 40 µl per well of 1M sulphuric acid. The optical density was read using a plate reader at 492 nm. A standard curve of antibody concentration versus absorption at 492 nm ($A_{492}$) was plotted was plotted for the control antibody and the concentration of the test antibody determined by comparison with the standard.

Example 6

Protection of TNF Alpha Sensitive Cells In Vitro by TNF Alpha Neutralization using Modified Antibodies The effectiveness of anti-TNF alpha antibodies to neutralize the lethal effect of TNF alpha on a cell line grown in vitro was evaluated using the method of Galloway (Galloway et al. 1991 J. Immunol. Meth. 140:37-43). The assay uses the murine fibrosarcoma cell line WEHI164, a line which is very sensitive to the lethal effect of TNF alpha.

For the assay, cells were grown overnight in the presence of a fixed, lethal concentration of TNF alpha and a range of different antibody concentrations. The next day, the metabolic activity of cells was measured as an indication of survival. Antibodies that neutralize TNF alpha confer a protective effect to the cells and thereby a greater metabolic activity is measured in the assay.

WEHI164 were obtained from the European Collection of Animal Cell Cultures (ECACC No. 8702250) and grown in DMEM medium with Glutamax, (Gibco, Paisley, UK), 10% fetal calf serum (Perbio, Chester, UK) and containing the antibiotic-mycotic (Gibco). On the day prior to assay, cells are sub-cultured to ensure active proliferation during the subsequent assay period. The assay was conducted in 96-well plates in duplicate for all treatments. Plates were prepared to contain dilutions of control antibody, test antibody and negative control with no antibody. Typically, doubling dilution series of the antibodies were arranged across a plate starting from a concentration of 10 μg/ml antibody in a volume of 50 μl. A stock solution of TNF alpha (PeproTech EC Ltd., London, UK) at 50 μg/ml in medium containing 4 μg/ml of actinomycin was prepared and added to the treatment wells. The TNF alpha solution was mixed by gently tapping the plate and the plate incubated for at least two hours at room temperature before the prepared solutions were transferred to the assay plate containing the cells.

Figure 2:
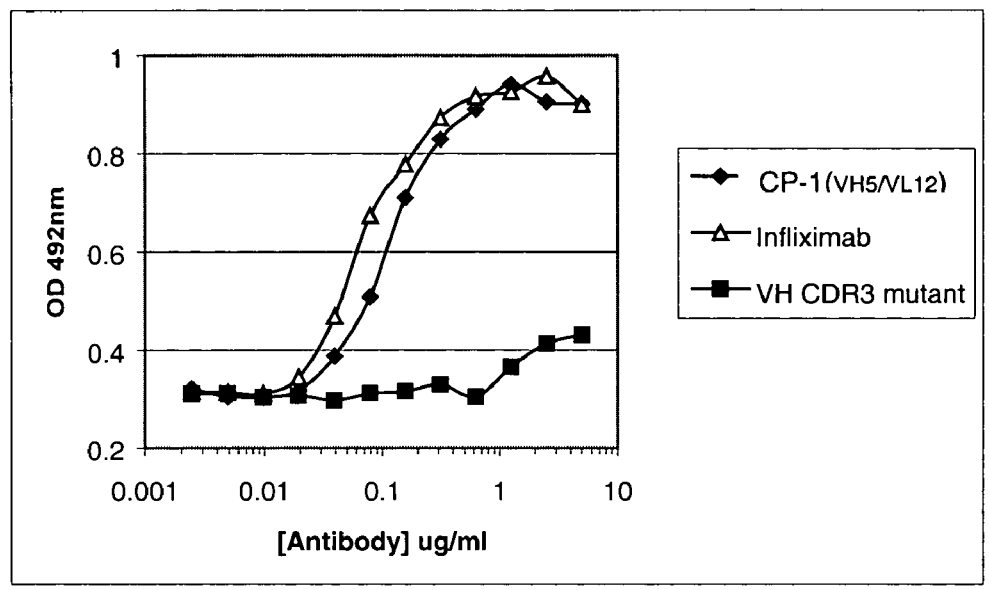
FIG. 2 graphically illustrates a reduction of TNF alpha induced killing of WEHI cells in vitro using a chimeric anti-TNF alpha composition of the invention (chimeric antibody CP-1, comprising the heavy chain/light chain variable region combination VH5/VL12 and human constant regions) relative to infliximab.

The assay plate was prepared by seeding about $2.5 \times 10^4$ cells in about 50 μl well and incubating for at least about 1 hour at 37° C., 5% $CO_2$. Following this, about 50 μL of the TNF alpha/antibody mixture or control preparation was transferred from the plate used to dilute out the various treatments. The cell and treatment mixtures were mixed by gently tapping the plate and the plate incubated overnight at about 37° C. in a humidified atmosphere containing 5% $CO_2$. On the following day, the metabolic activity of the cells in each well was assessed using a CELLTITER® 96 Aqueous One Solution Cell Proliferation Assay" (Promega, Southampton, UK). Following addition of the assay solution, the plates were incubated for a further 90 minutes and the absorbance of the solutions in each well was read using a plate reader at about 492 nm. The absorbance figures are plotted versus antibody concentration. In all assays the positive control preparation was a sample of the therapeutic antibody infliximab (Schering-Plough Ltd., UK), which in this assay consistently demonstrated significant TNF alpha neutralization at concentrations of less than about 0.1 μg/ml. Similarly the modified antibody of the present invention consistently demonstrated a protective effect in this assay equivalent to the positive control preparation. FIG. 2 shows an example plot from this assay.

Example 7

Neutralization of TNF Alpha Stimulated Production of ICAM-1 by Human Endothelial Cells In Vitro The ability of anti-TNF alpha antibodies to neutralize TNF alpha stimulated production in human umbilical vein endothelial (HUVE) cells of membrane bound ICAM-1, was tested in an in vitro assay. HUVE cells were grown in a 96-well plate in the presence of TNF alpha and varying concentrations of test or control antibody. The quantitative relative expression of membrane bound ICAM-1 was subsequently assessed by cell lysis and an enzyme linked immunoabsorbance assay (ELISA) using a commercially available ICAM-1 detection system.

For the assay, two parallel sets of 96-well plates are prepared. One set, termed the "assay plate", was seeded with cells, the other, termed the "preparation plate", was used to prepare the dilutions of TNF alpha and the test and control antibody solutions. The contents of the preparation plate were ultimately transferred to the assay plate. All assays were conducted in duplicate.

For the assay plate, HUVE cells (Cambrex Bio Science, Wokingham, UK) were seeded at a density of about $5 \times 10^4$ cells per well in a volume of about 50 μl. The cells were allowed to adhere to the plate by incubation at 37° C., 5% $CO_2$ for at least about 2 hours.

For the preparation plate, doubling dilution series of the test and positive control antibody were set out in duplicate across the plate. The starting concentration for the antibodies was 20 μg/ml in a final volume of 100 μl/well. The negative control received no antibody.

A solution of 40 ng/ml TNF alpha (PeproTech EC Ltd., London, UK) in medium was prepared and 100 μl per well added to each of the treatment wells on the preparation plate. The plate was mixed by gentle tapping and incubated for 45 minutes at room temperature. Following this incubation, about 50 μl from each well of the preparation plate was added to its corresponding well in the assay plate. The assay plate was incubated for about 23 hours at 37° C. in a humidified atmosphere containing 5% $Co_2$.

Next day, the medium from each wells was removed and the cells were washed once with phosphate buffered saline (PBS). The cells were lysed and each lysate was assayed for the presence of ICAM-1. Lysis was achieved by incubation at about 4° C. for about 45 minutes in about 80 μl of lysis buffer. The lysis buffer comprised about 8.7 g/l NaCl, about 6.05 g/l Tris 0.5% (v/v), NP40, at about pH 8. Lysis buffer also contained protease inhibitors PMSF, iodoacetamide, and benzamide, at about 100 mM concentration and pepsatin A and leupeptin at about 50 mM and 5 mM concentrations, respectively. These inhibitors were added fresh to the lysis buffer at time of use.

The well contents were mixed using a micropipette before removing the lysate to a fresh round-bottom 96-well plate. The plate was spun to clear precipitated cell debris and the cleared lysate was removed to another fresh 96-well plate for storage, (−20° C.) or immediate assay.

Figure 3:
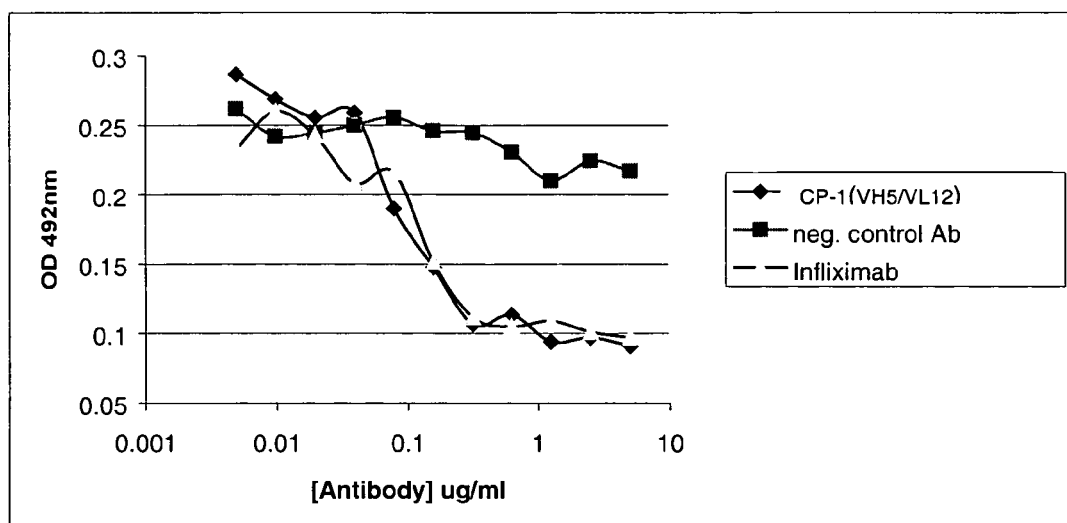
FIG. 3 graphically illustrates a reduction of TNF alpha stimulated ICAM-1 expression in human umbilical vein endothelial cells (HUVEC) in vitro using a chimeric anti-TNF alpha antibody of the invention (CP-1) relative to infliximab.

About 20 μl of cleared lysate from each cell was analyzed for the presence of solubilized ICAM-1 using a commercial ELISA system (sICAM-1 Module set; Bender Medsystems, Towcester, UK) and conditions recommended by the supplier. The absorbance of the solutions in each well was read using a plate reader at 492 nm. The absorbance figures ($A_{492}$) were plotted versus antibody concentration. In all assays, the positive control was a sample of the therapeutic antibody infliximab (Schering-Plough Ltd.), which in this assay consistently demonstrated significant TNF alpha neutralization at concentrations of less than about 1 μg/ml. Similarly the modified antibody of the present invention consistently demonstrated a concentration dependent inhibition of ICAM-1 expression equivalent to the positive control. FIG. 3 shows an example plot from this assay.

Example 8

Competition Assay of Modified Antibodies for Binding to TNF Alpha

The ability of the modified antibodies of the present invention to compete with the TNF alpha receptor (RII, p75) was measured in a competition ELISA, based on the method of Siegel et al. (Siegel et al., (1995) *Cytokine* 7(1):15-25). ELISA plates were coated with the receptor (TNF alpha RII-Fc) and incubated with a mixture of a fixed amount of biotinylated TNF alpha and a doubling dilution series of the antibody. Binding of TNF alpha to the receptor was measured by colorimetric assay using a Streptavidin-HRP conjugate.

The assay was conducted using Immulon 2HB 96-well plates, (Fisher, Loughborough, UK) prepared by coating overnight at 4° C. with 5 μg/ml TNF alpha RII-Fc (R&D Systems, Abingdon, UK) in carbonate coating buffer. A volume of 50 μl was applied to each well of the plate. The coated plates were washed at least five times with PBS-0.05% (v/v) in Tween 20, (PBS-T) and blocked by addition of a solution of 1% (v/v) BSA in PBS-T and further incubation at room temperature for at least one hour.

During this incubation, a dilution plate was set up in which the test antibody and control reagents were set out. Typically, a doubling dilution series starting at a concentration of about 50 μg/ml in a final volume of 50 μl were used for each test antibody. Controls included non-TNF alpha binding antibody as a negative control, and a preparation of clinical grade infliximab as the positive control. Control antibodies were of the same isotype as the test antibodies. Following addition of the antibodies, 50 µl per well of a solution of 50 ng/ml biotin-TNF alpha was added and the plate mixed by gentle tapping. The TNF alpha was the same as used above (Peprotech, London, UK) and biotinylated using EZ link Sulfo-NHS-biotin (Perbio, Tattenhall, UK), using the suppliers recommended protocol.

Figure 4:
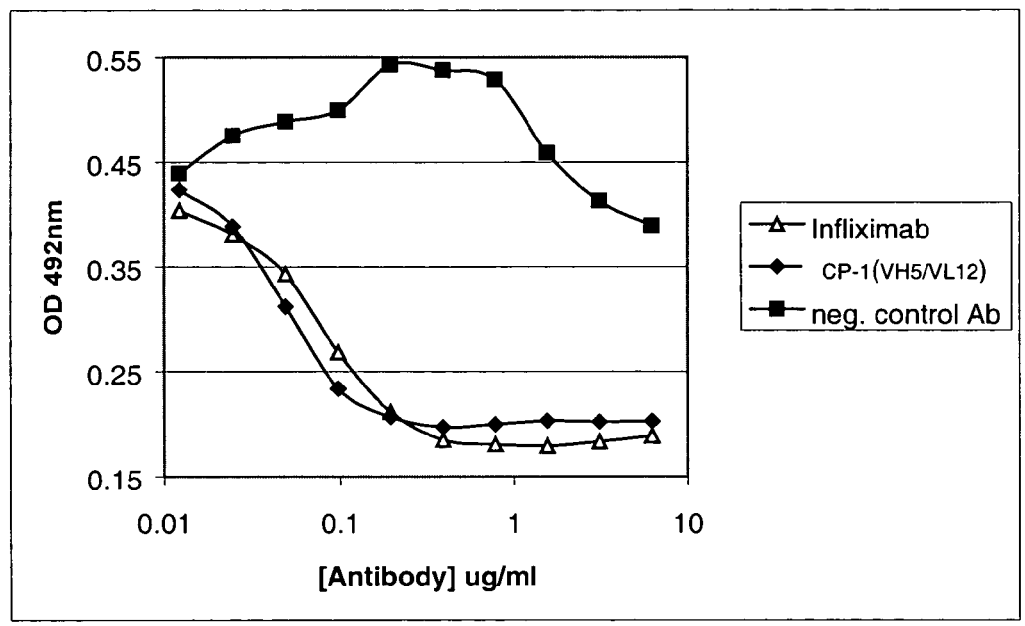
FIG. 4 graphically demonstrates the ability of a chimeric anti-TNF alpha antibody of the invention (CP-1) to compete for binding to TNF alpha with a positive control antibody (infliximab) in an in vitro assay.

The blocking solution was removed from the assay plate and the plate was washed with PBS-T as described above. About 50 µl from each well of the dilution plate was added to the corresponding well of the assay plate. Following mixing, the assay plate was incubated for at least one hour at room temperature. Following incubation, the plate was washed, and about 100 µl of a diluted Streptavidin-HRP (Sigma, Poole, UK) reagent was added to all wells of the plate. The plate was further incubated for at least one hour at room temperature and was washed with PBS-T as previously described. The assay was completed using about 100 µl/well of Sigma-fast OPD tablets (Sigma, Poole, UK), and the color reaction stopped by adding about 50 µl per well of 1M sulphuric acid. The plate was read and the results were plotted as antibody concentration versus absorbance at 492 nm. FIG. 4 shows an example plot from this assay. A preferred antibody of the present invention shows a concentration dependent competition curve for TNF alpha binding equivalent to that for the positive control antibody in this assay.

Example 9

Inhibition of TNF Alpha Induced Up-Regulation of IL-6 in Hs 27 Cells

Human foreskin fibroblast cells can be induced to produce IL-6 by exposure to TNF alpha. The ability of the modified antibodies of the present invention to block this up-regulation of expression was assessed by co-incubation of the cells with TNF alpha and the test antibodies, followed by a determination of the subsequent IL-6 levels secreted by the cells into the medium using a commercially available IL-6 detection system.

For the assay, two parallel sets of 96-well plates were prepared. One set, termed the "assay plate", was seeded with cells, the other, termed the "preparation plate," was used to prepare the dilutions of TNF alpha and the test and control antibody solutions. The contents of the preparation plate were ultimately transferred to the assay plate. All assays were conducted in duplicate.

For the assay plate, human foreskin fibroblast cells (Hs 27), obtained from the European Collection of Animal Cell Cultures (ECACC No. 94041901), were seeded at a density of about $2 \times 10^4$ cells per well and the cells were allowed to adhere to the plate by overnight incubation at 37° C. in a humidified atmosphere containing 5% $CO_2$. The culture medium throughout was DMEM+Glutamax (Gibco, Paisley, UK) containing 10% fetal calf serum (Perbio, Chester, UK) and a conventional antibiotic/mycotic preparation (Gibco).

For the preparation plate, doubling dilution series of the test and positive control antibody were set out in duplicate across the plate. The starting concentration for the antibodies was 1.25 µg/ml in a final volume of 100 µl/well. The negative control received no antibody. A solution of 3 ng/ml TNF alpha (PeproTech EC Ltd., London) was added to all antibody-containing wells, for the control wells with no antibody, an additional 100 µl/well of medium was added. The plate was mixed by gentle tapping and incubated at room temperature for at least 30 minutes.

Figure 9:
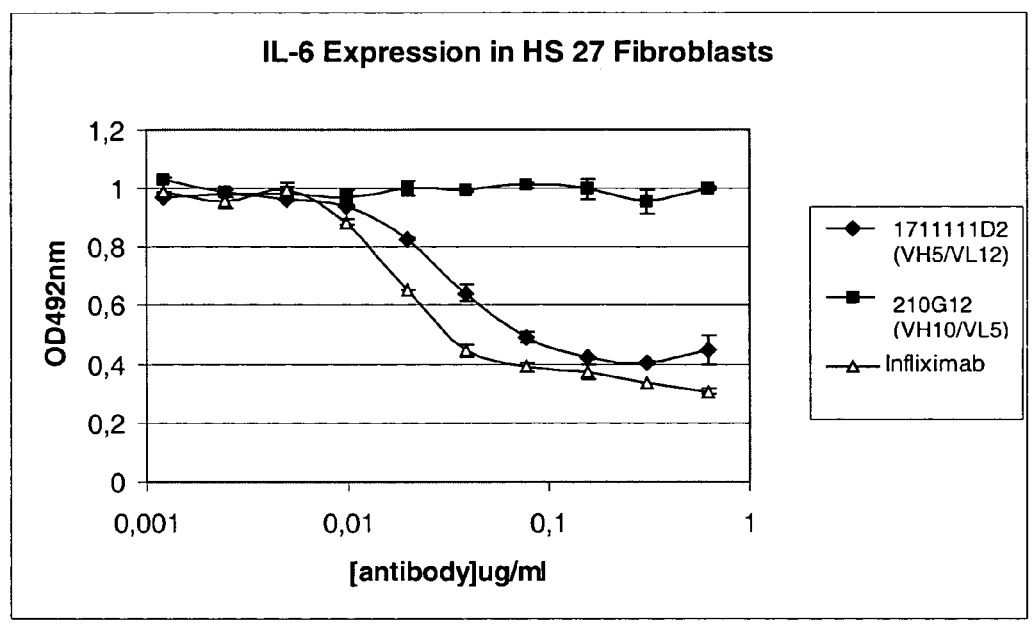
FIG. 9 provides a graph demonstrating the neutralization of TNF alpha stimulated production of IL-6 expression in human HS27 fibroblast cells in vitro using an anti-TNF alpha antibody of the invention (CP-1). The negative control (210G12) is a non-TNF alpha binding antibody and the positive control (infliximab) is TNF alpha neutralizing.

Medium was removed from each well of the assay plate containing the Hs 27 cells and about 100 µl from each well of the preparation plate was transferred to a corresponding well of the assay plate. The well contents were mixed by gently tapping the plate and incubated for at least 18 hours at 37° C. in a humidified atmosphere containing 5% $CO_2$. Following incubation, the medium was removed from each well to a fresh U-bottomed 96-well plate for storage at about −20° C. or immediate assay. The medium was analyzed for the presence of IL-6 using a commercial ELISA system (IL-6 Module set; Bender Medsystems, Towcester, UK) using conditions recommended by the supplier. About 50 µl of medium was diluted 1:15 (v/v) with buffer. The absorbance for the solution in each well was read using a plate reader at 492 nm. The absorbance figures were plotted versus antibody concentration. In all assays the positive control was a sample of the therapeutic antibody infliximab. A preferred modified antibody of the present invention consistently demonstrated a concentration dependent inhibition IL-6 expression. FIG. 9 shows an example plot from this assay.

Example 10

Detection of TNF Alpha

A simple plate ELISA was used to confirm the ability of the modified antibody of the present invention to bind to TNF alpha. The assay was conducted in comparison with a preparation of the therapeutic antibody infliximab (cA2) as positive control and a non-TNF alpha binding human IgG preparation (Sigma I2511) as a negative control. The assay was conducted using the method detailed below and demonstrated that a preferred antibody of the invention, CP-1, prepared in Example 5. CP-1 consists of a heavy chain having the amino acid residue sequence of SEQ ID NO: 161 (FIG. 16) and a light chain having the amino acid residue sequence of SEQ ID NO: 163 (FIG. 18). The gene encoding the heavy chain is shown in FIG. 15. The gene encoding the light chain is shown in FIG. 17. The heavy chain consists of variable region VH5 (SEQ ID NO: 3) and a constant region consisting of SEQ ID NO: 164. The light chain consists of variable region VL12 (SEQ ID NO: 6), and the constant region of SEQ ID NO: 165. CP-1 has about equal efficacy to the control antibody (infliximab) in this assay. A typical binding curve for the assay is depicted as FIG. 7.

Immulon 2HB 96-well plates, (Fisher, Loughborough, UK) were coated overnight at 4° C. with 2.5 µg/ml TNF alpha (PeproTech, London, UK) in carbonate coating buffer. A volume of 50 µl was applied to each well of the plate. The coated plates were washed three times with PBS-T.

Figure 7:
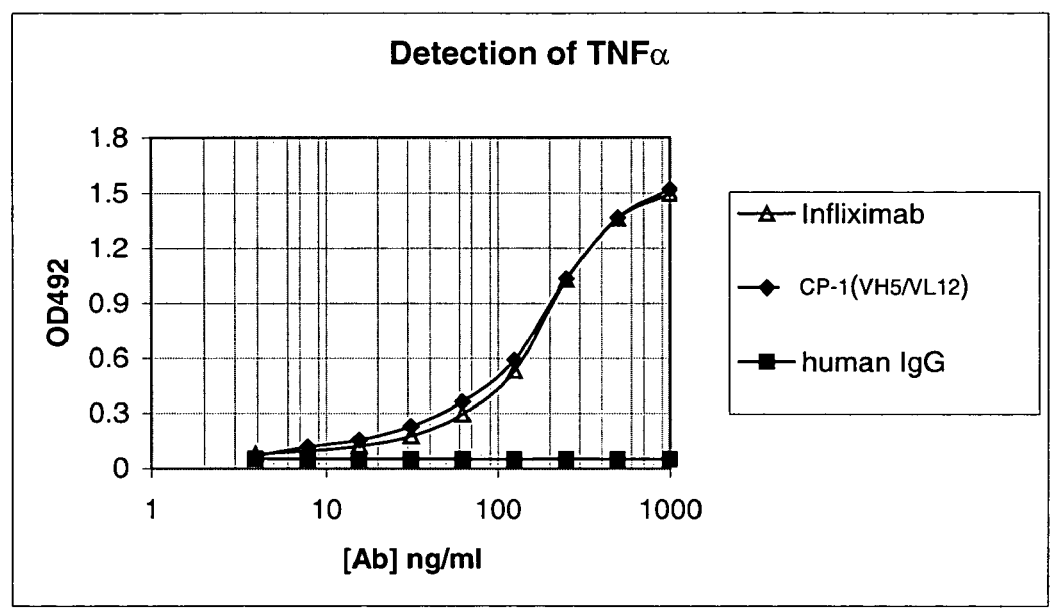
FIG. 7 shows results of a plate ELISA in which TNF alpha is detected by the modified antibody of the invention (CP-1). The binding curve is a plot of the antibody concentration versus optical density at 492 nm (OD492).

A doubling dilution series of each antibody was prepared and applied in a volume of 100 µl per well, each in duplicate. The highest antibody concentration was 1 µg/ml. Plates were incubated for about 1 hour at room temperature and were washed with PBS-T as previously described. To detect bound antibody, the plates were incubated with a Mouse-anti human IgG-HRP conjugate (Sigma, Poole, UK) diluted 1/1000 in PBS-T. Incubation was for at least 90 minutes at room temperature. The plates were again washed using PBS-T and the bound antibody was visualized using 100 µl/well of Sigma-Fast OPD. The color was allowed to develop for about 5 minutes and the reaction was stopped by addition of 40 µl/well of 1M $H_2SO_4$ The plates were read at 492 nm and the data plotted as concentration of antibody versus the optical density. FIG. 7 shows a representative binding curve indicating functional equivalence in this assay between a preferred modified antibody of the invention (CP-1) and the positive control.

Example 11

Demonstration of Reduced Immunogenic Potential in Modified Anti-TNF Alpha Antibody Using Human PBMC In Vitro Proliferation Assay For T cell proliferation assays, about $4 \times 10^6$ PBMC (per well) from healthy donors were incubated with control (infliximab) and modified antibody (CP-1) in 2 ml bulk cultures (in 24-well plates). Cells from each donor were treated with modified and control antibodies at 5 and 50 µg/ml concentrations. In addition, an untreated control bulk culture was maintained, enabling stimulation indexes to be determined. At days 5, 6, 7 and 8, cells from each bulk culture were gently agitated and 50 µl samples were removed in triplicate for determination of the proliferation index. The 50 µl sample aliquots were each transferred to 3 wells of a U-bottom 96-well plate. Fresh AIM V media (130 µl) was added to each of the 96-wells. Cells were pulsed (for 18-21 hours) with 1 µCi [$^3$H]Thymidine per well diluted in a total volume of 20 µl AIM V medium. The total volume for each culture was about 200 µl. CPM values were collected using a beta-plate reader and the stimulation index for each time point was determined as described in Example 2 above.

Figure 10:
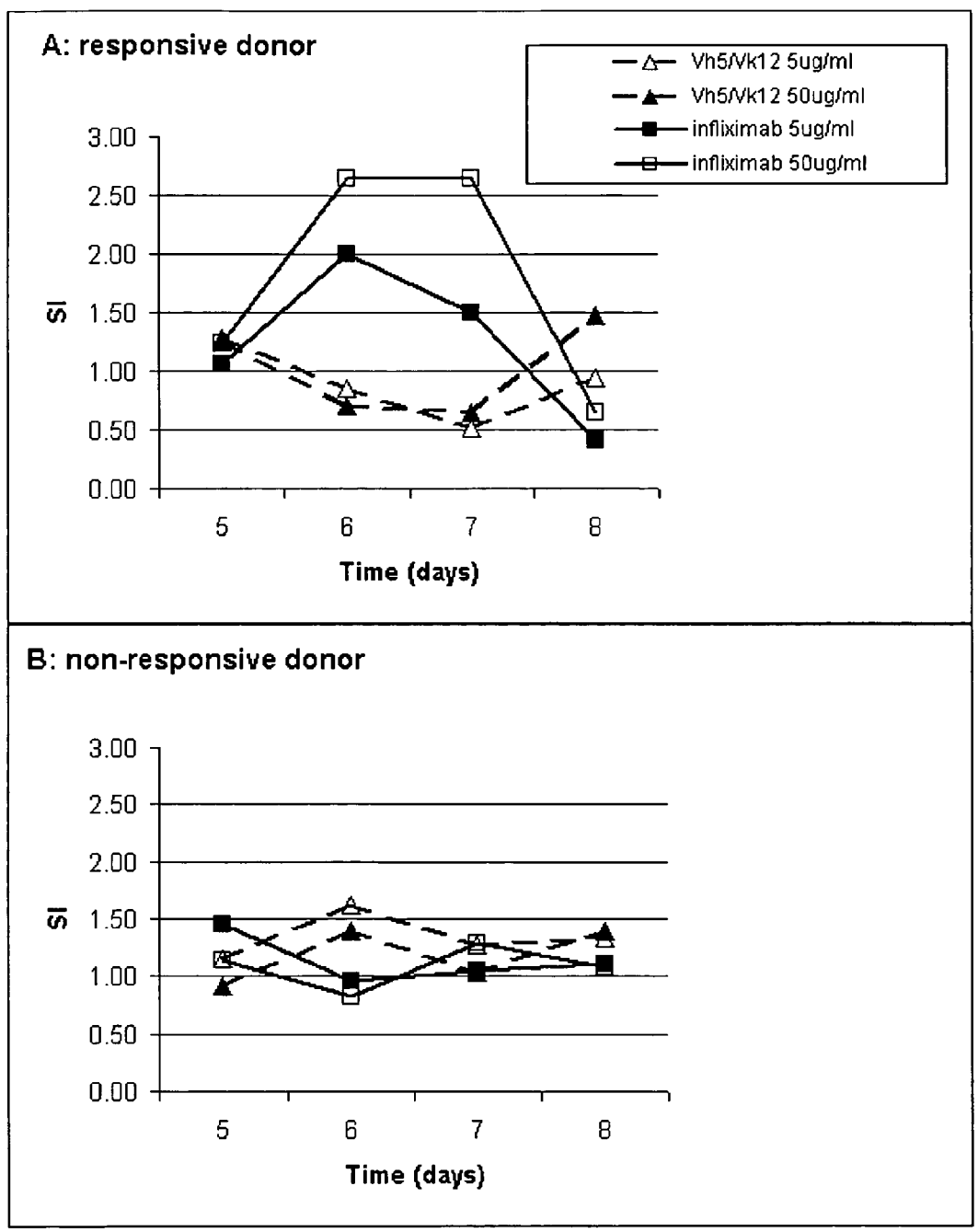
FIG. 10 provides plots depicting the results of an immunogenicity assay using naive human PBMC cultured in the presence of differing concentrations of modified antibody (CP-1) or immunogenic parental antibody (infliximab). The graphs show the results from a responsive donor PBMC (Panel A) and non-responsive donor PBMC (Panel B). SI=stimulation index.

The SI was plotted for each time point and antibody treatment. A significant SI was taken as a value greater than 2. In responsive donors, treatment with infliximab resulted in a significant proliferative response with a peak at day 7. In the same donors, treatment with an antibody of the invention (CP-1) did not result in a significant proliferative response. This result indicates a reduced immunogenic potential in the preferred antibody of the present invention compared with its counterpart control antibody (infliximab). A representative plot from this assay is provided in FIG. 10.

The foregoing disclosure is provided to illustrate the features of the present invention and is not meant to limit the appended claims.

---

We claim:

1. An isolated polypeptide consisting of residues 7-21 of SEQ ID NO: 11.

2. An isolated polypeptide consisting of residues 10-24 of SEQ ID NO: 11.

3. An isolated polypeptide consisting of SEQ ID NO: 142.

* * * * *